US012806253B2

(12) United States Patent
Zhan et al.

(10) Patent No.: US 12,806,253 B2
(45) Date of Patent: Nov. 24, 2026

(54) CST6, CELLS EXPRESSING CST6 AND METHODS OF USE

(71) Applicant: BioVentures, LLC, Little Rock, AR (US)

(72) Inventors: Fenghuang Zhan, Little Rock, AR (US); John D. Shaughnessy, Jr., Little Rock, AR (US); Jin-Ran Chen, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 854 days.

(21) Appl. No.: 18/019,052

(22) PCT Filed: Aug. 2, 2021

(86) PCT No.: PCT/US2021/044186
§ 371 (c)(1),
(2) Date: Jan. 31, 2023

(87) PCT Pub. No.: WO2022/026950
PCT Pub. Date: Feb. 3, 2022

(65) Prior Publication Data

US 2023/0293649 A1 Sep. 21, 2023

Related U.S. Application Data

(60) Provisional application No. 63/211,873, filed on Jun. 17, 2021, provisional application No. 63/059,740, filed on Jul. 31, 2020.

(51) Int. Cl.

| | |
|---|---|
| ***A61K 38/57*** | (2006.01) |
| ***A61K 35/17*** | (2025.01) |
| ***A61P 19/10*** | (2006.01) |

(52) U.S. Cl.
CPC .............. *A61K 38/57* (2013.01); *A61K 35/17* (2013.01); *A61P 19/10* (2018.01)

(58) Field of Classification Search
CPC ............................ A61K 38/57; C07K 14/8139
See application file for complete search history.

(56) References Cited

U.S. PATENT DOCUMENTS

| | | | | |
|---|---|---|---|---|
| 5,476,865 | A | 12/1995 | Panetta et al. | |
| 6,987,100 | B2 | 1/2006 | Tanaka et al. | |
| 2002/0052476 | A1* | 5/2002 | Ni ...................... | C07K 14/8139 435/325 |
| 2013/0210699 | A1 | 8/2013 | Srivatsan et al. | |

OTHER PUBLICATIONS

Jin et al., Cell Res., 2012, vol. 22(9):1356-1373.*
Tosi P., Scientifica, 2013, vol. 2013(1), Article ID 104546, 12 pages.*
Rivenbark et al., Exp. Mol. Pathol., 2007, vol. 83(2):188-197.*
Lee et al., J. Drug Deliv., 2012, vol. 2012, Article ID 915375, 17 pages.*
Abboud-Jarrous, G. et al. Cathepsin L is responsible for processing and activation of proheparanase through multiple cleavages of a linker segment. J Biol Chem. 2008 283(26):18167-76.
Abrahamson, M. et al. Cystatins. Biochem Soc Symp. 2003:(70):179-99.
Agnelli, L. et al. Molecular classification of multiple myeloma: a distinct transcriptional profile characterizes patients expressing CCND1 and negative for 14q32 translocations. J Clin Oncol. 2005. 23(29):7296-306.
Al, L. et al. Epigenetic silencing of the tumor suppressor cystatin M occurs during breast cancer progression. Cancer Res. 2006.66(16):7899-909.
Altschul, S.F. et al. Gapped BLAST and PSI-BLAST: a new generation of protein database search programs. Nucleic Acids Res. 1997.25(17):3389-402.
Alvarez-Fernandez, M. et al. Inhibition of legumain is due to a second reactive site in some cystatins. J Biol Chem. Jul. 2, 1999;274(27):19195-203.
Bartel, T.B. H et al. F18-fluorodeoxyglucose positron emission tomography in the context of other imaging techniques and prognostic factors in multiple myeloma. Blood. 2009.114(10):2068-76.
Bendre, M.S. et al. Expression of interleukin 8 and not parathyroid hormone-related protein by human breast cancer cells correlates with bone metastasis in vivo. Cancer Res. 2002.62(19):5571-9.
Benezeder, T. et al. Multigene methylation analysis of enriched circulating tumor cells associates with poor progression-free survival in metastatic breast cancer patients. Oncotarget. 2017. 8(54):92483-92496.
Bergsagel, P.L. et al. Cyclin D dysregulation: an early and unifying pathogenic event in multiple myeloma. Blood. 2005.106(1):296-303.
Boyce, B.F. et al. Bone Remodeling and the Role of TRAF3 in Osteoclastic Bone Resorption. Front Immunol. Front Immunol. 2018. 28:9:2263.
Briggs, J.J. et al. Cystatin E/M suppresses legumain activity and invasion of human melanoma. BMC Cancer. Jan. 15, 2010:10:17. doi: 10.1186/1471-2407-10-17.
Broyl, A. et al. Gene expression profiling for molecular classification of multiple myeloma in newly diagnosed patients. Blood. 2010. 116(14):2543-53.
Burden, R.E. et al. Recombinant cathepsin S propeptide attenuates cell invasion by inhibition of cathepsin L-like proteases in tumor microenvironment. Mol Cancer Ther. 2008. 7(3):538-47.
Cheng, T. et al. Cystatin M/E is a high affinity inhibitor of cathepsin V and cathepsin L by a reactive site that is distinct from the legumain-binding site. A novel clue for the role of cystatin M/E in epidermal cornification. J Biol Chem. 2006. 281(23):15893-9.
Cheng, T. et al. Colocalization of cystatin M/E and its target proteases suggests a role in terminal differentiation of human hair follicle and nail. Invest Dermatol. 2009. 129(5):1232-42.

(Continued)

*Primary Examiner* — Xiaozhen Xie
(74) *Attorney, Agent, or Firm* — Quarles & Brady, LLP

(57) ABSTRACT

The present invention provides methods of treating bone loss or cancer using CST6. In these methods, CST6 may be provided as a recombinant CST6 protein, a polynucleotide construct comprising CST6, or an immune cell expressing CST6 protein.

17 Claims, 58 Drawing Sheets

Specification includes a Sequence Listing.

(56) References Cited

OTHER PUBLICATIONS

Cheuiche, A.V. et al. Performance of Cystatin C-Based Equations for Estimation of Glomerular Filtration Rate in Diabetes Patients: A Prisma-Compliant Systematic Review and Meta-Analysis. Sci Rep. 2019; 9: 1418.
Colditz, J. et al. Postnatal Skeletal Deletion of Dickkopf-1 Increases Bone Formation and Bone Volume in Male and Female Mice, Despite Increased Sclerostin Expression. J Bone Miner Res. 2018. 33(9):1698-1707.
Coleman, R.E. et al. Metastasis and bone loss: advancing treatment and prevention. Cancer Treat Rev. 2010. 36(8):615-20.
Cox, J.L. Cystatins and cancer. Front Biosci (Landmark Ed). 2009. 14(2):463-74.
D'Costa, Z.C. et al. TBX2 represses CST6 resulting in uncontrolled legumain activity tosustain breast cancer proliferation: a novel cancer-selective target pathway with therapeutic opportunities. Oncotarget. 2014. 5(6):1609-20.
Drake, M.T. et al. Cathepsin K Inhibitors for Osteoporosis: Biology, Potential Clinical Utility, and Lessons Learned. Endocr Rev. 2017. 38(4):325-350.
Franqui-Machin, R. et al. Destabilizing NEK2 overcomes resistance to proteasome inhibition in multiple myeloma. J Clin Invest. 2018. 128(7):2877-2893.
Fried, L.F. et al. Association of kidney function with incident hip fracture in older adults. J Am Soc Nephrol. 2007. 18(1):282-6.
Gao, M. et al. Identification and Characterization of Tumor-Initiating Cells in Multiple Myeloma. J Natl Cancer Inst. 2020;112(5):507-515. doi:10.1093/jnci/djz159.
Garfall, A.L. et al. Chimeric Antigen Receptor T Cells against CD19 for Multiple Myeloma. N Engl J Med. 2015; 373(11): 1040-1047;doi:10.1056/NEJMoa1504542 (https://pubmed.ncbi.nlm.nih.gov/26352815/).
Gocheva, V. et al. Distinct roles for cysteine cathepsin genes in multistage tumorigenesis. Genes Dev. 2006. 20(5): 543-556.
Gooding, S. et al. Transcriptomic profiling of the myeloma bone-lining niche reveals BMP signalling inhibition to improve bone disease. Nat Commun. 2019. 10(1):4533.
Guay, J. et al. Potency and selectivity of inhibition of cathepsin K, L and S by their respective propeptides. Eur J Biochem (2000) 267(20):6311-6318.
Hay, S.B. et al. The Human Cell Atlas bone marrow single-cell interactive web portal. Exp Hematol. 2018. 68:51-61.
Hosokawa, M. et al. Over-expression of cysteine proteinase inhibitor cystatin 6 promotes pancreatic cancer growth. Cancer Sci. 2008. 99(8):1626-32.
Hou, A.J. et al. TGF-β-responsive CAR-T cells promote anti-tumor immune function. Bioeng Transl Med. 2018. 3(2):75-86. doi: 10.1002/btm2.10097.
CST6 cystatin E/M [*Homo sapiens* (human)] Gene ID: 1474 https://www.ncbi.nlm.nih.gov/gene/1474.
Jin, L. et al. Differential secretome analysis reveals CST6 as a suppressor of breast cancer bone metastasis. Cell Res. 2012;22(9):1356-1373. doi: 10.1038/cr.2012.90, https://pubmed.ncbi.nlm.nih.gov/22688893/.
Karlin, S. and Altschul, S.F. Methods for assessing the statistical significance of molecular sequence features by using general scoring schemes. 1990. Proc. Natl. Acad. Sci. USA 87(6):2267-2268.
Kioulafa, M. et al. Methylation of the CST6 promoter is tied to unfavorable outcomes in breast cancer. 2009. Int J Cancer. 125(12):2887-92. doi:10.1002/ijc.24686.
Lacroix, A.Z. et al. Cystatin-C, renal function, and incidence of hip fracture in postmenopausal women. 2008. J Am Geriatr Soc. 56(8):1434-41.
Li, X. et al. CST6 protein and peptides inhibit breast cancer bone metastasis by suppressing CTSB activity and osteoclastogenesis. Theranostics. Oct. 11, 2021;11(20):9821-9832. doi: 10.7150/thno.62187. PMID: 34815788; PMCID: PMC8581426.
Lin, H-J, et al. Breast cancer-associated fibroblasts confer AKT1-mediated epigenetic silencing of Cystatin M in epithelial cells. Cancer Res. 2008. 68(24): 10257-66. doi: 10.1158/0008-5472.CAN-08-0288.
Liu, C. et al. Overexpression of Legumain in Tumors Is Significant for Invasion/Metastasis and a Candidate Enzymatic Target for Prodrug Therapy. Cancer Res. 2003.63(11):2957-64.
Morris, M.R. et al. Identification of candidate tumour suppressor genes frequently methylated in renal cell carcinoma. Oncogene. 2010. 29(14):2104-17. doi: 10.1038/onc.2009.493. Epub Feb. 15, 2010.
Nandy, S.K. and Seal, A. Structural Dynamics Investigation of Human Family 1 & 2 Cystatin-Cathepsin L1 Interaction: A Comparison of Binding Modes. PLoS One. Oct. 20, 2016; 11(10):e0164970.
Ochieng, J. and Chaudhuri, G.C. Cystatin Superfamily. J Health Care Poor Underserved. Feb. 2010; 21(1 Suppl): 51-70. doi: 10.1353/hpu.0.0257.
Oortveld, M.A.W. et al. Cathepsin B as a potential cystatin M/E target in the mouse hair follicle. Faseb J. 2017; 31(10):4286-4294. doi: 10.1096/fj.201700267R. Epub Jun. 8, 2017.
Park, J.H. et al. CD19-targeted CAR T-cell therapeutics for hematologic malignancies: interpreting clinical outcomes to date. Blood 2016; 127(26): 3312-3320. doi: (https://doi.org/10.1182/blood-2016-02-629063).
Pennisi, A. et al. Inhibitor of DASH proteases affects expression of adhesion molecules in osteoclasts and reduces myeloma growth and bone disease. Br J Haematol. 2009. 145(6):775-87. doi: 10.1111/j.1365-2141.2009.07696.x.
Peters, I.A. et al. DNA methylation biomarkers predict progression-free andoverall survival of metastatic renal cell cancer (mRCC) treated with antiangiogenic therapies. PLoS One. 2014.9(3):e91440. doi: 10.1371/journal.pone.0091440.
Podgorski, I. et al. Bone marrow-derived cathepsin K cleaves SPARC in bone metastasis. Am J Pathol. Sep. 2009; 175(3):1255-69. doi:10.2353/ajpath.2009.080906. Epub Aug. 21, 2009.
Priceman, S.J. et al. Regional Delivery of Chimeric Antigen Receptor-Engineered T Cells Effectively Targets HER2+ Breast Cancer Metastasis to the Brain. Clin Cancer Res. 2018;24(1):95-105. doi: 10.1158/1078-0432.CCR-17-2041, https://pubmed.ncbi.nlm.nih.gov/29061641/.
Pulukuri, S.M. et al Frequent loss of cystatin E/M expression implicated in the progression of prostate cancer. Oncogene 2009;28(31):2829-38.
Qiang, Y-W et al. Myeloma-derived Dickkopf-1 disrupts Wnt-regulated osteoprotegerin and RANKL production by osteoblasts: a potential mechanism underlying osteolytic bone lesions in multiple myeloma. Blood 2008;112(1):196-207.
Qiu, J. et al. Invasion suppressor cystatin E/M (CST6): high-level cell type-specific expression in normal brain and epigenetic silencing in gliomas. Lab Invest 2008;88(9):910-25.
Radhakrishnan, S.V. et al. CD229 CAR T cells eliminate multiple myeloma and tumor propagating cells without fratricide. Nat Commun. 2020; 11(1):798.doi: 10.1038/s41467-020-14619-z.
Rajkumar, S.V. et al. International Myeloma Working Group updated criteria for the diagnosis of multiple myeloma. Lancet Oncol. 2014;15(12):e538-48. doi: 10.1016/S1470-2045(14)70442-5.
Redondo-Muñoz, J. et al. Molecular Players in Hematologic Tumor Cell Trafficking. Front Immunol. Feb. 6, 2019:10:156. doi: 10.3389/fimmu.2019.00156.
Schönemeyer, A et al. Modulation of human T cell responses and macrophage functions by onchocystatin, a secreted protein of the filarial nematode Onchocerca volvulus. J Immunol. 2001; 167(6):3207-15.
Shaughnessy, J.D., Jr. et al. Pharmacogenomics of bortezomib test-dosing identifies hyperexpression of proteasome genes, especially PSMD4, as novel high-risk feature in myeloma treated with Total Therapy 3. Blood 2011;118(113):3512-24.
Shaughnessy, J.D., Jr. et al. A validated gene expression model of high-risk multiple myeloma is defined by deregulated expression of genes mapping to chromosome 1. Blood. 2007; 109(6):2276-2284.
Soh, H. Cystatin E/M Suppresses Tumor Cell Growth through Cytoplasmic Retention of NF-κB. Mol Cell Biol. 2016. 36(12): 1776-1792.

(56) References Cited

OTHER PUBLICATIONS

Sotiropoulou, G. et al. Identification, cloning, and characterization of cystatin M, a novel cysteine proteinase inhibitor, down-regulated in breast cancer. J Biol Chem. 1997. 272(2):903-10. doi: 10.1074/jbc.272.2.903.

Spencer, G.J. et al. Wnt signalling in osteoblasts regulates expression of the receptor activator of NFκB ligand and inhibits osteoclastogenesis in vitro. J Cell Sci. 2006. 119(Pt 7):1283-96.

Terpos, E. Cystatin-C is an independent prognostic factor for survival in multiple myeloma and is reduced by bortezomib administration. Haematologica. 2009 94(3):372-379.

Tessema, M. et al. Genome-wide unmasking of epigenetically silenced genes in lung adenocarcinoma from smokers and never smokers. Carcinogenesis. 2014;35(6):1248-1257. doi: 10.1093/carcin/bgt494, https://pubmed.ncbi.nlm.nih.gov/24398667/.

Tian, E. et al. The role of the Wnt-signaling antagonist DKK1 in the development of osteolytic lesions in multiple myeloma. N Engl J Med. 2003. 349(26):2483-2494.

UniProtKB Submission No. Q15828, Cystatin-M CST6, Nov. 1, 1997 (online). Retrieved from the internet: http://www.uniprot.org/uniprot/Q15828.

Veena, M.S. et al. Inactivation of the cystatin E/M tumor suppressor gene in cervical cancer. Genes Chromosomes Cancer 2008;47:740-54.

Vincents, B. et al. The Human Protease Inhibitor Cystatin C Is an Activating Cofactor for the Streptococcal Cysteine Protease IdeS. Chemistry & Biology. 2008. 15(9):960-968.

Wallin, H. et al. Low-level internalization of cystatin E/M affects legumain activity and migration of melanoma cells. J Biol Chem. Sep. 1, 2017;292(35):14413-14424. doi: 10.1074/jbc.M117.776138. Epub Jun. 19, 2017. PMID: 28630039; PMCID: PMC5582836.

Wu, C. et al. Chimeric antigen receptor T cell therapies for multiple myeloma. J Hematol Oncol 12, 120 (2019) (https://doi.org/10.1186/s13045-019-0823-5).

Xiu, Y. et al. Chloroquine reduces osteoclastogenesis in murine osteoporosis by preventing TRAF3 degradation. J Clin Invest. 2014;124(1):297-310.

Xu, L. et al. Cell Adhesion Molecule CD166 Drives Malignant Progression and Osteolytic Disease in Multiple Myeloma. Cancer Res. 2016;76(23):6901-6910.

Yaccoby, S. et al. Primary myeloma cells growing in SCID-hu mice: a model for studying the biology and treatment of myeloma and its manifestations. Blood. Oct. 15, 1998;92(8):2908-13.

Yaccoby, S. and Epstein, J. The proliferative potential of myeloma plasma cells manifest in the SCID-hu host. Blood. Nov. 15, 1999;94(10):3576-82.

Yaccoby, S. et al. Inhibitory effects of osteoblasts and increased bone formation on myeloma in novel culture systems and a myelomatous mouse model. Haematologica. 2006. 91(2):192-199.

Yaccoby, S. et al. Antibody-based inhibition of DKK1 suppresses tumor-induced bone resorption and multiple myeloma growth in vivo. Blood (2007) 109(5):2106-2111.

Yao, Z. et al. NF-kappaB p100 limits TNF-induced bone resorption in mice by a TRAF3-dependent mechanism. The Journal of clinical investigation 2009; 119(10):3024-34.

Zeeuwen, P.L. et al. Cystatin M/E expression is restricted to differentiated epidermal keratinocytes and sweat glands: a new skin-specific proteinase inhibitor that is a target for cross-linking by transglutaminase. J Invest Dermatol. May 2001; 116(5):693-701.

Zeeuwen, P.L.J.M. et al. The biology of cystatin M/E and its cognate target proteases. J Invest Dermatol. Jun. 2009; 129(6):1327-38.

Zeeuwen, P.L.J.M. et al. Evidence that unrestricted legumain activity is involved in disturbed epidermal cornification in cystatin M/E deficient mice. Hum Mol Genet. 2004 13(10):1069-1079.

Zhan, F. et al. Global gene expression profiling of multiple myeloma, monoclonal gammopathy of undetermined significance, and normal bone marrow plasma cells. Blood. 2002 99(5):1745-1757.

Zhan, F. et al. The molecular classification of multiple myeloma. Blood. 2006; 108(6):2020-2028.

Zhang, C. et al. Engineering CAR-T cells. Biomark Res. 2017;5:22. Published Jun. 24, 2017. doi: 10.1186/ s40364-017-0102-y.

Zhang, J. Cystatin m: a novel candidate tumor suppressor gene for breast cancer. Cancer Res. Oct. 1, 2004;64(19):6957-64. doi: 10.1158/0008-5472.CAN-04-0819.

Zhou, Y. et al. Prediction of cytogenetic abnormalities with gene expression profiles. Blood 2012; 119(21):e148-50.

International Search Report and Written Opinion for International Patent Application No. PCT/US2021/044186, dated Jun. 22, 2023.

* cited by examiner

A

Cst6 BSAS vs protein

C

E

F

A

A

B

A

B

C

A

C

E

A

E

A

C

G

B

C

D

F

E

A

A

CST6, CELLS EXPRESSING CST6 AND METHODS OF USE

CROSS-REFERENCE TO RELATED APPLICATIONS

This application is a National Stage Entry of International Application Number PCT/US2021/044186, filed Aug. 2, 2021, which claims priority to U.S. Provisional Application No. 63/059,740 filed on Jul. 31, 2020 and U.S. Provisional Application No. 63/211,873 filed on Jun. 17, 2021, the contents of which are incorporated by reference in their entireties.

SEQUENCE LISTING

A Sequence Listing accompanies this application and is submitted as an ASCII text file of the sequence listing named "169852_00084_ST25.txt" which is 6,501 bytes in size and was created on Jul. 22, 2021. The sequence listing is electronically submitted via EFS-Web with the application and is incorporated herein by reference in its entirety.

BACKGROUND

Bone destruction is one of the main complications of cancers, especially myeloma. Healthy bone is constantly remodeled through bone destruction by osteoclasts and compensated for by new bone formation by osteoblasts. This remodeling keeps the bone strong. Myeloma cells have the tendency to form small or large clusters. The bone destruction in myeloma is seen where the large myeloma clusters are. In myeloma, increased bone destruction is caused by increased RANK-L and decreased osteoprotegerin (OPG), which is secreted by osteoblasts and acts as a soluble decoy receptor, capturing RANK-L. New bone formation in myeloma is almost non-existent because maturation from mesenchymal cells to osteoblasts is inhibited by DKK1, which binds to the LRP6 co-receptor and inhibits beta-catenin dependent Wnt signaling.

To prevent bone disease in myeloma, patients receive either bisphosphonate therapy (Aredia or Zometa) or denosumab, which is a monoclonal antibody that inhibits RANK-L. Although effective, both classes of drugs cause osteonecrosis of the jaw (ONJ), and they have no direct effect on myeloma cell growth. Thus, there is a need in the art for new therapies that can be used both to inhibit cancer growth and to prevent bone loss.

SUMMARY

In a first aspect, the present disclosure provides a method for inhibiting or reducing bone loss in a subject in need thereof. The method comprises administering an effective amount of CST6 to the subject to inhibit or reduce bone loss. In some embodiments, the subject is suffering from a bone disease, or has bone loss due to cancer or other diseases.

In a second aspect, the disclosure provides a method for treating bone disease that is characterized by decreased expression of CST6 and bone loss in a subject in need thereof. The method comprises administering an effective amount of CST6 to the subject to treat the bone disease and reduce bone loss.

In a third aspect, the disclosure provides a method for inhibiting cancer cell growth in a subject having cancer. The method comprises administering an effective amount of an immune cell expressing CST6 protein to the subject.

In a fourth aspect, the disclosure provides an immune cell comprising a chimeric antigen receptor and a heterologous polynucleotide encoding a CST6 protein.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

DETAILED DESCRIPTION OF THE INVENTION

Figure 1:
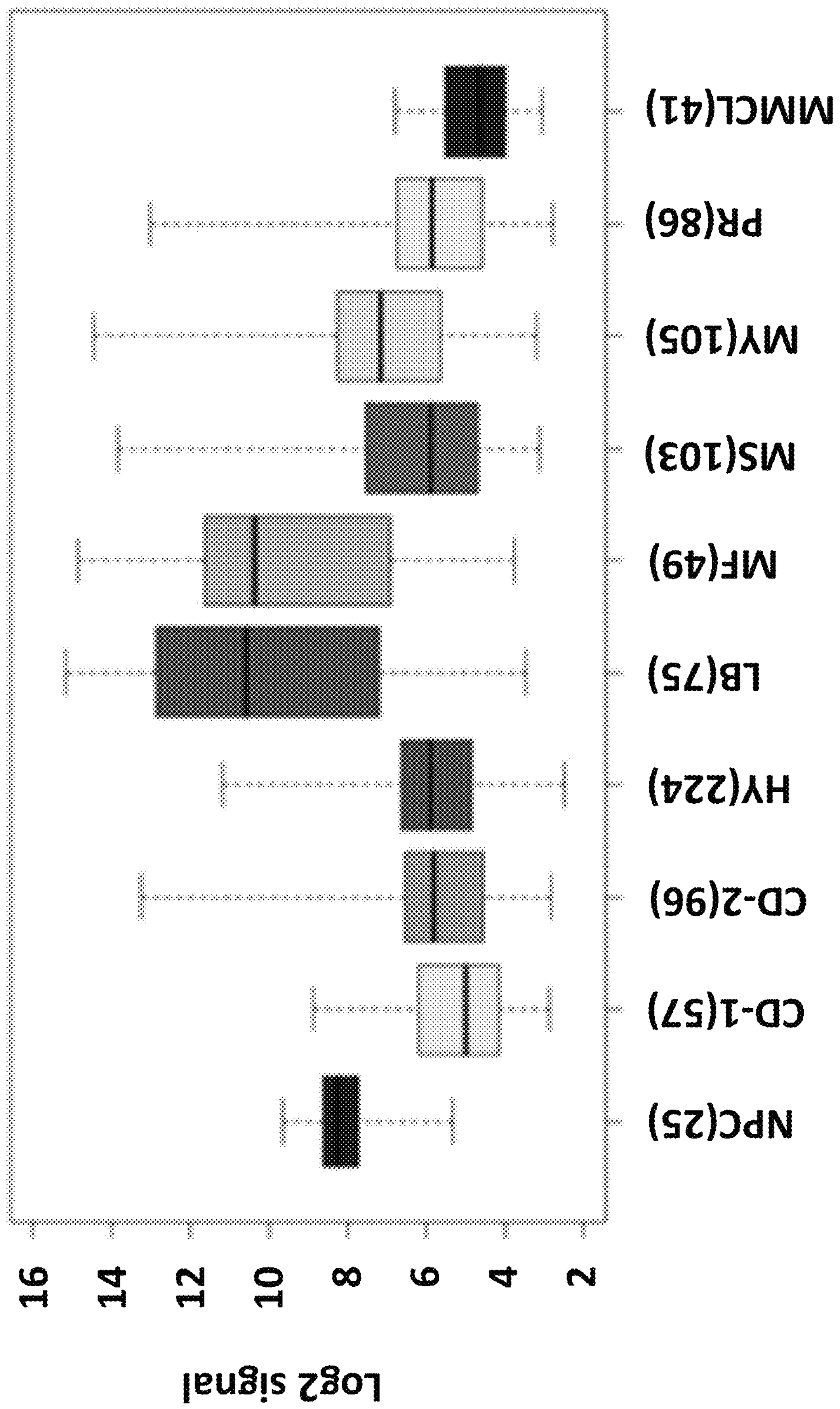
FIG. 1 shows that increased CST6 expression is negatively correlated with bone lytic lesions in myeloma. (A) Box charts of CST6 expression in myeloma subtypes from 351 newly diagnosed MM patients. The 8 MM subtypes CD-1, CD-2, HY, LB, MF, MS, MY, and PR are distributed along the x axis and the log 2-transformed CST6 Affymetrix Signal is plotted on the y axis. The percentage of MM patients with 3 or more bone lytic lesions detected by MRI is labelled in each subtype. The top, middle, and bottom middle lines of each box correspond to the 75th percentile (top quartile), 50th percentile (median), and 25th percentile (bottom quartile) of the log 2-transformed CST6 Affymetrix Signal, respectively. The whiskers extend from the 10th percentile (bottom decile) to the 90th percentile (top decile). The Kruskal-Wallis test was used to identify differences in CST6 expression across the groups. (B) The expression of CST6 and DKK1 at the mRNA level is mutually exclusive, which suggests that these genes are regulated by a common hierarchical mechanism. (C) Decreased bone lytic lesion in MM patients with high expression of CST6. The Affymetrix Signal of CST6 is indicated by the bar. Data from a total of 244 newly diagnosed MM samples that were subjected to both FDG-PET and CT tests is grouped into 3 classes on the x axis: samples without bone lytic lesion (n=72), samples with 1-2 bone lytic lesions (n=118), and samples with at least 3 bone lytic lesions (n=55). P values are analyzed by one-way ANOVA (three groups) or a student t test (two groups).
Figure 1:
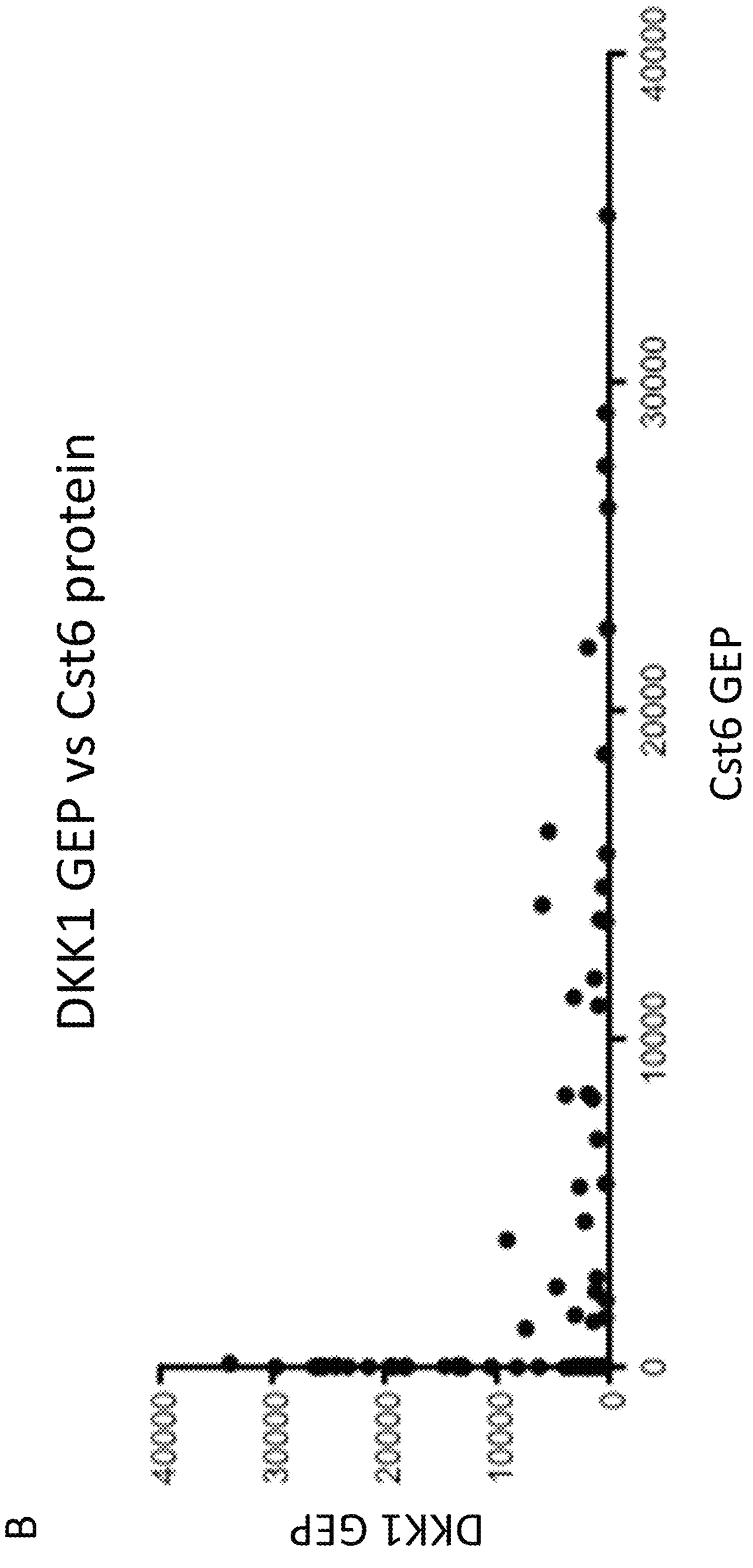
Figure 1:
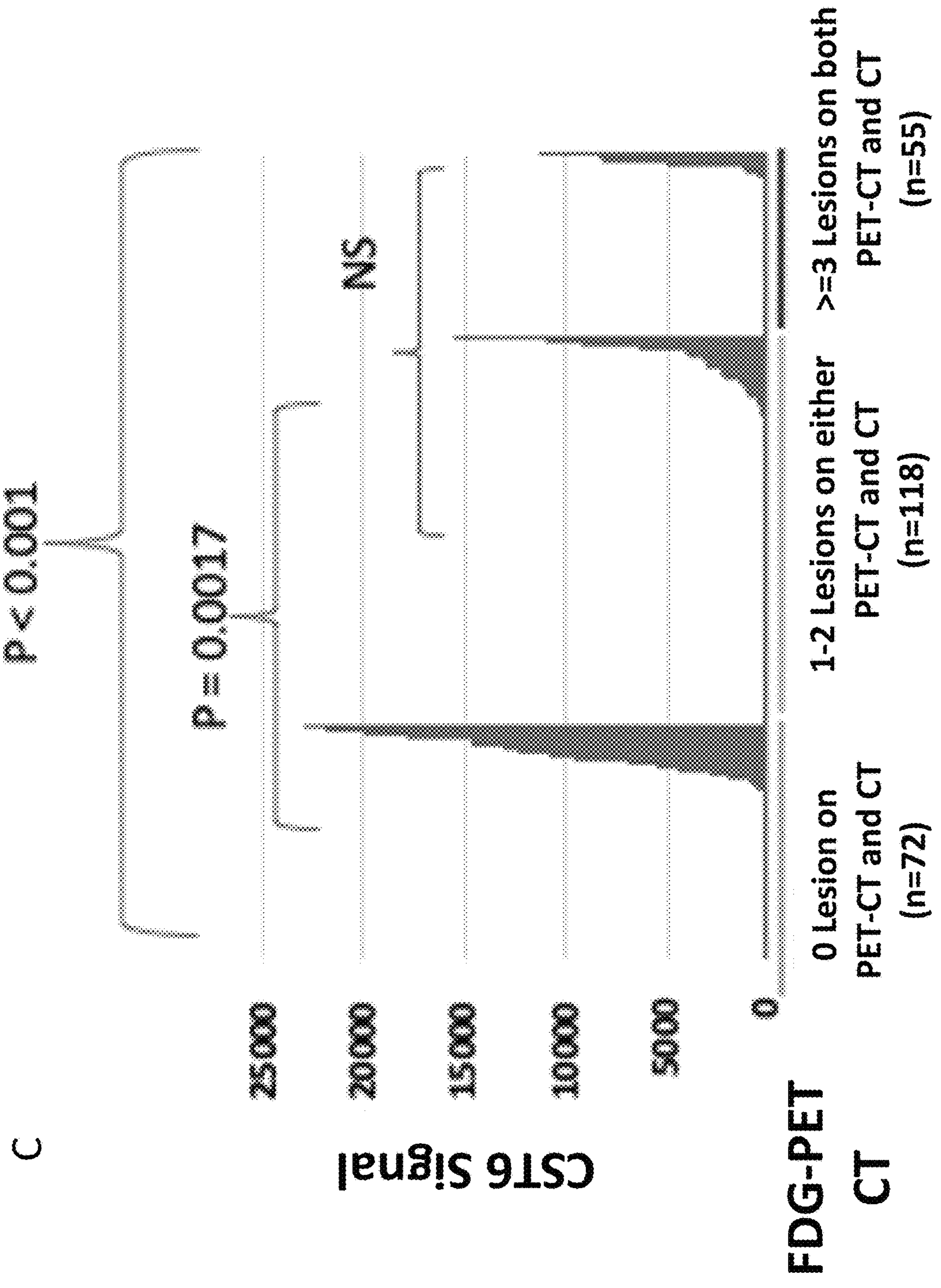

The present disclosure describes methods of inhibiting bone loss and treating cancer. Specifically, the methods may be used to reduce or inhibit bone loss in multiple myeloma and other cancers that readily metastasize to the bone marrow. The methods may also be used to mitigate bone loss caused by other factors, for example, from estrogen deficiency or bone diseases. Also provided are compositions for use in the methods.

Methods of Inhibiting Bone Loss

In a first aspect, the disclosure provides a method for inhibiting or reducing bone loss in a subject in need thereof. The method comprises administering an effective amount of CST6 to the subject to inhibit or reduce bone loss. In some embodiments, the subject is suffering from a bone disease. In the Examples, the inventors identified CST6 as a new potential anti-resorptive agent. CST6 encodes the protein cystatin M/E, which is a secreted cysteine protease inhibitor that is known to play a role in osteoclast function. The terms "CST6", "CST6 protein", and "cystatin M/E" are used here interchangeably to refer to the protein encoded by the CST6 gene.

In the methods of the present invention, CST6 can be provided to the subject in several forms, including (a) as a recombinant protein, (b) as a polynucleotide construct comprising the CST6 gene, (c) as an immune cell that expresses CST6, and/or (d) a nanocarrier comprising the recombinant protein or polynucleotide construct encoding CST6.

For example, in some embodiments, the method comprises administering to the subject a recombinant CST6 protein or a polynucleotide construct comprising CST6 (SEQ ID NO:2). As used herein, a "recombinant protein" is modified protein that is expressed from recombinant DNA (i.e., DNA comprising genetic material from multiple sources that is formed via genetic recombination). As used herein, the term "polynucleotide construct" refers to an artificially constructed (i.e., not naturally occurring) polynucleotide molecule. Constructs are commonly provided as vectors or plasmids. Within the construct, the CST6 gene may be under the control of a transcriptional regulator (e.g., a promoter and/or enhancer) or linked to a translational control sequence. The construct may further include a selectable marker, a protein tag, or another genetic elements known in the art. A construct can be transduced, transformed, or transfected into a cell, thereby causing the cell to express the protein encoded by the construct.

The methods may utilize a recombinant CST6 protein comprising the human CST6 protein (i.e., SEQ ID NO:3) or the mouse CST6 protein (i.e., SEQ ID NO:4). In some embodiments, the recombinant CST6 protein is the protein of SEQ ID NO:3 or a protein having a sequence with at least 75% identity to SEQ ID NO:3, at least 80% identity to SEQ ID NO:3, at least 90% identity to SEQ ID NO:3, at least 95% identity to SEQ ID NO:3, at least 98% identity to SEQ ID NO:3, or at least 99% sequence identity to SEQ ID NO:3.

Alternatively, the methods may utilize a polynucleotide construct comprising the full-length CST6 cDNA (i.e., SEQ ID NO:1) or the coding sequence (CDS) thereof (i.e., SEQ ID NO:2). In some embodiments, the polynucleotide construct comprises the CDS of SEQ ID NO:2 or a sequence with at least 75% identity to SEQ ID NO:2, at least 80% identity to SEQ ID NO:2, at least 90% identity to SEQ ID NO:2, at least 95% identity to SEQ ID NO:2, at least 98% identity to SEQ ID NO:2, or at least 99% sequence identity to SEQ ID NO:2.

Percentage of sequence similarity" or "percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Protein and nucleic acid sequence identities are evaluated using the Basic Local Alignment Search Tool ("BLAST"), which is well known in the art (Karlin and Altschul, 1990, Proc. Natl. Acad. Sci. USA 87: 2267-2268; Altschul et al., 1997, Nucl. Acids Res. 25: 3389-3402). The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990), the disclosure of which is incorporated by reference in its entirety. The BLAST programs can be used with the default parameters or with modified parameters provided by the user.

In some embodiments, the recombinant CST6 protein is linked to a tag or targeting agent. As used herein, the term "tag" refers to a heterologous polypeptide sequence that is linked to the CST6 protein. Many protein tags are commonly used in the art, including those that can be used for protein detection (e.g., green fluorescent protein (GFP), luciferase, horseradish peroxidase), and those that can be used for protein purification (e.g., 6-Histidine (His), hemagglutinin (HA), cMyc, GST, Flag, V5, and NE).

As used herein, the term "targeting agent" refers to a molecule that specifically binds to a complementary molecule expressed on the cellular surface. Targeting agents include agents that can specifically target the compositions of the present invention (i.e., a recombinant CST6 protein, a construct comprising the CST6 gene, or CST6-expressing immune cells to osteoclast cells and/or tumor cells. Suitable targeting agents include, for example, CST6-conjugates (e.g., bisphosphonate), CST6 peptides, antibodies, aptamers, and chimeric antigen receptors. For example, in some embodiments, the targeting agent comprises complementary determining regions (CDR) of a monoclonal antibody, variable regions of a monoclonal antibody, and/or antigen binding fragments thereof. A complementarity determining region (CDR) is a short amino acid sequence found in the variable domains of an antigen receptor (e.g., an immunoglobulin or T-cell receptor) that complements an antigen and therefore provides the receptor with its specificity for that particular antigen.

In other embodiments, the methods comprise administering to the subject an immune cell that expresses CST6 (SEQ ID NO: 3). Using CST6-expressing immune cells to provide CST6 protein to the subject provides advantages over using the CST6 protein alone, as the CST6 protein is unstable when delivered in vivo and is degraded before being able to provide any therapeutic benefit. Further, the CST6-expressing immune cell can comprise a chimeric antigen receptor that can specifically target cells that express a target antigen (e.g., a tumor associated antigen), thus providing targeted delivery of the CST6 protein.

The immune cells used in the present invention are white blood cells. In some embodiments, the immune cell is a T cell (e.g., CD4+ or CD8+ T cell), a natural killer (NK) cell (e.g., $CD3^{-}CD56^{+}$ cells), or a macrophage (e.g., CD14+ CD16+ macrophage). In preferred embodiments, the immune cell is a T cell. Immune cells are known in the art and have characteristic morphologies and marker expression that allows them to be isolated from a subject for use in the methods described herein by conventional means. Immune cells that express CST6 can be generated, for example, by transfecting the full-length CST6 cDNA directly into the immune cells.

In some embodiments, the immune cell further expresses a targeting agent that binds to a tumor antigen specific to the cancer of the subject. As used herein, an "antigen" is a molecule (e.g., a protein, glycoprotein, or carbohydrate) capable of inducing an immune response in the body. As used herein, the term "tumor antigen" refers an antigen that is expressed on the surface of a tumor cell and can be used to target the tumor. Tumor antigens include both tumor-specific antigens (i.e., molecules expressed on cancer cells but not on healthy cells) and tumor-associated antigens (i.e., molecules that have elevated levels on tumor cells but are also expressed at lower levels on healthy cells). For example, in some embodiments, the subject has multiple myeloma, and the immune cell is capable of binding to a marker of multiple myeloma, e.g., B-cell maturation antigen (BCMA) or CD19.

In some embodiments, the targeting agent expressed by the immune cell is a chimeric antigen receptor (CAR) or fragment thereof. In some embodiments, the CAR is specific for a tumor antigen, allowing the CAR to target the immune cell to the cancer cells that express that particular tumor antigen. See the section titled "Chimeric antigen receptors (CARs)", below, for a more detailed discussion of CARs. In some embodiments, the immune cell is a CAR T-cell that expresses CST6. Methods of incorporating an engineered CAR into immune cells for expression on the immune cell surface are known in the art. For example, a nucleic acid encoding a CAR polypeptide comprising an intracellular signaling domain, a transmembrane domain, and an extracellular domain may be transfected into the immune cell. In some embodiments, a full-length CAR cDNA or coding region is introduced into the immune cell. In some embodiments, a DNA construct or vector is used to introduce the CAR into the immune cell. Methods of introducing cDNA, DNA constructs, and vectors into an immune cell are known in the art.

In some embodiments, the immune cell comprises an isolated exogenous nucleic acid or DNA construct that encodes CST6, the CAR, or a combination thereof. In some embodiments, the immune cell comprises a DNA construct that comprises the polynucleotide sequence of CST6 (SEQ ID NO:2) and is capable of expressing CST6.

The "subject" to which the methods of the present invention are applied may be a mammal or a non-mammalian animal, such as a bird. Suitable mammals include, but are not limited to, humans, cows, horses, sheep, pigs, goats, rabbits, dogs, cats, bats, mice and rats. In certain embodiments, the methods may be performed on lab animals (e.g., mice and rats) for research purposes. In other embodiments, the methods are used to treat commercially important farm animals (e.g., cows, horses, pigs, rabbits, goats, sheep, and chickens) or companion animals (e.g., cats and dogs). In a preferred embodiment, the subject is a human. The subject treated by the methods of the present invention may have bone loss resulting from several diseases or conditions, including, for example, bone disease, osteoporosis or estrogen deficiency, breast cancer bone metastasis, and lung cancer bone metastasis. In some embodiments, the subject has cancer and is undergoing cancer treatment.

In Example 3, the inventors demonstrate that CST6 protein can be used to prevent bone loss in a mouse model of osteoporosis. Thus, in some embodiments, the subject has osteoporosis. Osteoporosis is a bone disease that occurs when the body loses too much bone, makes too little bone, or both. As a result, bones become weak and may break from a fall or, in serious cases, from sneezing or minor bumps. The term osteoporosis encompasses all forms of primary osteoporosis, including postmenopausal (type I) osteoporosis and senile (type II) osteoporosis, as well as secondary osteoporosis. Secondary osteoporosis develops when certain medical conditions (e.g., hyperparathyroidism, diabetes, thalassemia, multiple myeloma, intestinal malabsorption, leukemia, liver disease, metastatic bone disease, Marfan's syndrome, acromegaly, Cushing's syndrome, or scurvy) and medications (e.g., antacids containing aluminum, oral corticosteroids, heparin, methotrexate, anticonvulsants, Lasix, thyroid hormone, or steroid (cortisone) therapy) increase bone remodeling, leading to disruption of bone reformation.

In Example 2, the inventors demonstrate that CST6 protein can be used to inhibit bone loss in a mouse model of multiple myeloma. Thus, in some embodiments, the subject has bone loss associated with cancer. In particular embodiments, the subject has multiple myeloma or breast cancer. In Example 2, the inventors demonstrate that the presence of bone disease in multiple myeloma patients is associated with reduced CST6 expression. Thus, in some embodiments, the cancer does not express CST6, and is, therefore, more likely to induce bone disease. In Example 2, bone loss was assessed via detection bone lesions. Thus, in some embodiments, the subject has osteolytic bone lesions. "Osteolytic bone lesions" are spots of bone damage that result from cancerous plasma cells building up in the bone marrow. Bone lesions can be detected, for example, using positron emission tomography-computed tomography (PET-CT).

In embodiments in which the subject has bone loss associated with cancer, the method may utilized an immune cell that comprises a chimeric antigen receptor (CAR) that is specific to the cancer of the subject. The term "specific" refers to the ability of a protein to bind one molecule in preference to other molecules. A protein that is specific to a target molecule binds to the target molecule but does not bind in a significant amount to other molecules present in the sample. Specific binding can also mean binding to its target with an affinity that is often at least 25% greater, more often at least 50% greater, most often at least 100% (2-fold) greater, alternatively at least ten times greater, alternatively at least 20-times greater, and alternatively at least 100-times greater than the affinity with any other molecule.

As used herein, the terms "administering" and "administration" refer to any method of providing the treatment to the patient, for example, any method of providing a pharmaceutical preparation to a subject. Such methods are well known to those skilled in the art and include, but are not limited to, oral administration, transdermal administration, administration by parenteral administration, including injectable such as intravenous administration, intra-arterial administration, intramuscular administration, intradermal administration, intrathecal administration and subcutaneous administration, rectal administration, sublingual administration, buccal administration, among others. Administration can be continuous or intermittent.

The term "effective amount" refers to an amount sufficient to produce beneficial or desirable biological and/or clinical results. That result can be reducing, inhibiting, or slowing bone loss; ameliorating a symptom of a bone disease; and/or reducing, inhibiting, or preventing the growth of cancer cells, reducing, inhibiting or preventing metastasis of the cancer cells or invasiveness of the cancer cells or metastasis, or reducing, alleviating, inhibiting or preventing at least one symptoms of the cancer or metastasis thereof. A beneficial effect can take the form of an improvement over baseline, i.e., an improvement over a measurement or observation made prior to initiation of therapy according to the method.

The methods described above inhibit or reduce bone loss. "Bone loss" is a reduction of bone mass that can result in decreased bone density and deterioration of bone tissue. Bone loss is caused by an imbalance between bone resorption and bone formation (e.g., due to increased activity or number of osteoclasts or reduced activity or number of osteoblasts). Bone loss can be quantified, for example, using a bone density test, e.g., using x-rays, body computed tomography (CT), magnetic resonance imaging (MRI), or a bone density scan. Alternatively, bone loss can be detected as the presence of bone lesions, e.g., using positron emission tomography-computed tomography (PET-CT), or as changes to the bone structure or morphology, e.g., using micro-computed tomogtaphy (micro-CT) or bone histomorphometry.

Methods of Treating Bone Disease

In a second aspect, the disclosure provides a method for treating bone disease that is characterized by decreased expression of CST6 and bone loss in a subject in need thereof. The method comprises administering an effective amount of CST6 to the subject to treat the bone disease and reduce bone loss.

As used herein, the term "bone disease" refers to a disease that is characterized by bone loss. Exemplary bone diseases include, but are not limited to, osteoporosis, Paget's disease, alveolar bone loss, osteomalacia, renal osteodystrophy, and cancer. In Example 3, the inventors demonstrate that CST6 protein can be used to prevent bone loss in a mouse model of osteoporosis. Thus, in some embodiments, the subject has osteoporosis.

Estrogen deficiency can lead to excessive bone resorption accompanied by inadequate bone formation. Estrogen deficiency causes osteoporosis in postmenopausal women (i.e., due to the precipitous drop in estrogen caused by menopause) and contributes to the development of osteoporosis in elderly men. Thus, in some embodiments, the bone disease treated by the method is associated with estrogen-deficient bone loss. In particular embodiments, the bone disease is post-menopausal osteoporosis.

Bone destruction is one of the main complications of cancers, especially myeloma. CST6 is downregulated in multiple cancers, including breast cancer, lung cancer, cervical cancer, etc. Thus, in some embodiments, the subject has cancer and associated bone loss. In some embodiments, the cancer is breast cancer or multiple myeloma.

In these methods, CST6 can be provided to the subject in several forms, including as a recombinant protein, as a polynucleotide construct comprising the CST6 gene, or as an immune cell that expresses CST6. Thus, in the some embodiments, the administering of the CST6 protein comprises administering: (a) a recombinant CST6 protein; (b) a polynucleotide construct comprising CST6 (SEQ ID NO:2) and capable of expressing CST6; (c) an immune cell expressing CST6 protein (SEQ ID NO: 3) and/or (d) a nanocarrier comprising (a) or (b) to the subject to reduce or inhibit bone loss.

Further, CST6 may be administered as a component of a pharmaceutical composition. For example, in some embodiments, CST6 is administered via a carrier. "Pharmaceutically acceptable carriers" are reagents used for the production and delivery of pharmaceutical compositions. Pharmaceutically acceptable carriers are typically non-toxic and inert. A pharmaceutically acceptable carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, pharmaceutically acceptable salts, wetting agents, or other biocompatible materials. A tabulation of ingredients listed by the above categories, may be found in the U.S. Pharmacopeia National Formulary, 1857-1859 (1990).

In some embodiments, the carrier is a nanoparticle. The nanoparticle may be designed to target CST6 to bone or to osteoclasts, specifically. Examples of nanomaterials that can selectively target bone tissues and cells include, without limitation, titanium nanotubes, gold nanoparticles, calcium phosphate nanoparticles, mesoporous silica nanoparticles, chitosan nanoparticles, poly(L-lactide-co-glycolide) (PLGA) nanoparticles, and liposomes. The nanoparticles may also be targeted using osteoclast-specific markers, such as OPG, RANK-Fc, and c-Src. Additionally, there are known peptide targeting motifs that can help target osteoclasts (e.g., one-targeting peptide motif $(Asp)^{14}$ or $(AspSerSer)^{6}$.

For purposes of the present invention, "treating" or "treatment" describes the management and care of a subject for the purpose of combating a disease, condition, or disorder. Treating includes the administration of the CST6 to prevent the onset of the symptoms or complications, alleviating the symptoms or complications, eliminating the disease, condition, or disorder. The aim of treatment includes the alleviation or prevention of symptoms, slowing or stopping the progression or worsening of a disease, disorder, or condition and/or the remission of the disease, disorder or condition. The term "treating" can be characterized by reduction in bone loss in the subject, preferably in a subject having cancer or susceptible to bone loss. Reduction or inhibition of bone loss can be in a patient undergoing cancer treatment, or in a patient that has undergone cancer treatment.

Methods of Treating Cancer

In a third aspect, the disclosure provides a method for inhibiting cancer cell growth and bone loss in a subject having CST6-cancer. The method comprises administering an effective amount of recombinant CST6 protein or an immune cell expressing CST6 to the subject.

The present methods can be used for treatment of cancers, specifically cancers in which CST6 is downregulated. As used herein the term "cancer" or "tumor" refers to an abnormal mass of tissue in which the growth of the mass surpasses and is not coordinated with the growth of normal tissue. Suitable cancers for treatment with the present methods can be determined by one skilled in the art, and include, for example, multiple myeloma, lung cancer, breast cancer, prostate cancer, cervical cancer, brain cancer, etc. In some embodiments, the cancer is a "CST6-cancer", i.e., a cancer that does not express CST6 at detectable levels or at least has reduced expression of CST6 as compared to a similar non-cancerous cell.

In Example 2, the inventors demonstrate that the presence of bone disease in multiple myeloma patients is associated with reduced CST6 expression. Thus, in some embodiments, the method comprises: (a) obtaining a sample of the cancer from the subject, and (b) detecting the lack of expression of CST6 in the cancer cells prior to administering the CST6. Detection of CST6 may be at the protein level (e.g., using ELISA, western blotting, or protein mass spectrometry assays) or at the RNA level (e.g., using reverse transcription polymerase chain reaction (RT-PCR) or Northern blotting).

The "sample of the cancer" may comprise a tissue sample (e.g., fat, muscle, skin, neurological, tumor, etc.), a fluid sample (e.g., saliva, blood, serum, plasma, urine, stool, cerebrospinal fluid, etc.), or cancer cells. In some embodiments, the sample comprise a tumor sample, such as a biopsy. A tumor sample may be fresh, frozen, or formalin fixed paraffin embedded (FFPE). In some embodiments, the sample is a "liquid biopsy," that is, a blood sample taken from a patient to monitor tumor progression by analysis of circulating tumor DNA.

In some embodiments, an immune cell expressing CST6 is administered to the subject. As discussed above, the immune cells used with the present invention are white blood cells. In some embodiments, the immune cell is the immune cell is a T cell, a NK T cell, or macrophage. In some embodiments, the immune cell is a T cell. In some embodiments, the immune cells comprise a DNA construct that comprises a polynucleotide sequence comprising CST6 (SEQ ID NO:2) and is capable of expressing CST6. In some embodiments, the immune cells expresses a tumor antigen specific to the cancer of the subject.

In some embodiments, the immune cells further comprise a chimeric antigen receptor (CAR) or fragment thereof that allows for specific targeting to cancer cells expressing the tumor antigen. In some embodiments, the immune cells are engineered CAR-T or CAR-NK cells that deliver the recombinant CST6 protein to the tumor niche.

In some embodiments, the immune cell is capable of binding to a tumor antigen specific to the subject's cancer. For example, in some embodiments, the cancer is multiple myeloma and the immune cell is capable of binding to a marker of multiple myeloma. In particular embodiments, the immune cell comprises a CAR capable of binding a marker of multiple myeloma. Suitable markers of multiple myeloma include, for example, BCMA, CD19, Kapp light chain, CD44 variant 6, CD56, CD70, CD38, CD138, SLAMF7, GPRC5D, and NKG2DL, CD229, and CD24. In other embodiments, the cancer is a CXCR4+ cancer, and the immune cell is capable of binding CXCR4. In particular embodiments, the immune cell comprises a CAR capable of binding CXCR4. In other embodiments, the cancer is a HER2+ breast cancer, and the immune cell is capable of binding HER2. In particular embodiments, the immune cell comprises a CAR capable of binding HER2. In other embodiments, the cancer is a TGFbeta+ lung cancer, and the immune cells is capable of binding TGFbeta. In particular embodiments, wherein the immune cell comprises a CAR capable of binding TGFbeta.

The methods of treating cancer described herein can further include resecting a tumor prior to administration of the immune cells. Resection of a tumor includes surgical removal of all or part of the tumor, including, in some instances, some of the margin of the normal tissue surrounding the tumor.

The methods of treating cancer may also further include administering an anti-cancer therapy. Suitable anti-cancer therapies are known in the art. Exemplary anti-cancer therapies include radiation, chemotherapy, administration of platinum-based drugs, immunomodulatory therapies (e.g., antibodies, chemokines, checkpoint inhibitors, cancer vaccines), or other standards of care. A "cancer treatment" may include administration of any such anti-cancer therapy.

The methods described above inhibit cancer cell growth. Cancer cell growth can be quantified, for example, using a cell proliferation assay, e.g., a metabolic activity assay, cell proliferation marker assay, ATP concentration assay, or a DNA synthesis assay. Alternatively, cell growth can be quantified using a cell viability assay, e.g., by staining the cells with trypan blue, which selectively colors dead cells blue, and counting the number of viable and dead cells.

Compositions

In a fourth aspect, the present invention provides CST6-expressing immune cells and compositions thereof. In some embodiments, the immune cell comprises a chimeric antigen receptor and a polynucleotide construct comprising CST6 (SEQ ID NO:2) and capable of expressing CST6.

As discussed above, the immune cells used with the present invention are white blood cells. In some embodiments, the immune cell is the immune cell is a T cell, a NK T cell, or macrophage. In preferred embodiments, the immune cell is a T cell.

In some embodiments, the immune cell comprises a chimeric antigen receptor that is specific to a tumor antigen. In some embodiments, the tumor antigen is BMCA. In other embodiments, the tumor antigen is CD19. Other suitable tumor antigens are contemplated and within the scope of the present invention.

The present invention also provides compositions in which the immune cells have been formulated into a suitable form for administration to a subject. The compositions may comprise a pharmaceutically acceptable carrier, preferably a carrier that maintains the viability of the cells prior to administration.

Kits

In a fifth aspect, kits for carrying out the methods described herein are provided. The kits provided may contain the necessary components with which to carry out one or more of the above-noted methods. In one embodiment, the kit is for treating a subject having cancer or bone loss. The kits may comprise the recombinant CST6, polynucleotide constructs encoding CST6, CST6-expressing immune cells, or nanocarriers comprising CST6 described herein.

Chimeric Antigen Receptors (CARs)

The immune cells used in the methods and compositions of the present invention may optionally comprise a chimeric antigen receptor (CAR) or fragment thereof, e.g., to allow for specific targeting of the immune cell to cancer cells expressing a particular tumor antigen. The term "chimeric antigen receptor (CAR)", as used herein, refers to artificial chimeric immunoreceptors, artificial T-cell receptors, or chimeric T cell receptors that have antigen specificity. CARs comprise an extracellular antigen binding domain that is operably connected to (e.g., as a fusion protein) a transmembrane domain to allow it to be expressed on the surface of the immune cell. In some embodiments, the CAR also comprises an intracellular signaling domain, which induces immune cell activation and signaling once the CAR comes into contact with its specific antigen target.

In some embodiments, the antigen binding domain comprises an antibody or a portion thereof (e.g., a single-chain variable fragment (scFv)). In other embodiments, the antigen binding domain comprises the ligand of a target receptor or a receptor for a target ligand.

The CAR can be used to target the immune cells to multiple myeloma cells by targeting a multiple myeloma-specific antigen, e.g., B-cell maturation antigen (BCMA). Suitable multiple myeloma antigens include, for example, BCMA, CD19, Kapp light chain, CD44 variant 6, CD56, CD70, CD38, CD138, SLAMF7, GPRC5D, and NKG2DL, CD229, and CD24, as described by Wu et al. (J Hematol Oncol 2019; 12, 120), Radhakrishnan et al. (Nat Commun 2020; 11(1):798), and Gao et al. (J Natl Cancer Inst 2020; 112(5):507-515), the contents of which regarding CAR-T cells are incorporated by reference in their entirety.

Alternatively, the CAR can be used to target the immune cells to malignant B cells by targeting a B cell lineage-specific antigen, e.g., CD19. Suitable CD19-targeting CAR-T cells are known in the art, including those described by Jae et al. (Blood 2016; 127(26):3312-3320) and Garfall et al. (N Engl J Med. 2015; 373(11):1040-1047), the contents of which regarding CAR-T cells are incorporated by reference in their entirety.

CXCR4 is a chemokine receptor that regulates immune cell trafficking into and out of the bone marrow (see, e.g., *Front. Immunol.* 10:156). CXCR4 plays a role in cancers such as multiple myeloma, acute lymphoblastic leukemia (ALL), and chronic lymphocytic leukemia (CLL). Thus, in another embodiment, the CAR specifically binds to CXCR4 and used to target the immune cells to CXCR4+ cancer cells.

CST6 is known to suppress breast cancer bone metastasis (see, e.g., Cell Res. 2012; 22(9):1356-1373). Thus, in another embodiment, the CAR specifically binds to human epidermal growth factor receptor 2 (HER2) and used to target the immune cells to a HER2+ breast cancer. Suitable HER2-targeting CAR-T cells are known in the art, including those described by Priceman et al. (Clin Cancer Res. 2018; 24(1):95-105), the contents of which regarding CAR-T cells are incorporated by reference in their entirety.

As is multiple myeloma, CST6 is differentially expressed in lung cancer (see, e.g., Carcinogenesis. 2014; 35(6):1248-1257). Thus, in another embodiment, the CAR specifically binds to TGFbeta and used to target the immune cells to a TGFbeta$^{+}$ lung cancer. Suitable TGFbeta-targeting CAR-T cells are known in the art, including those described by Hou et al. (Bioeng Transl Med. 2018; 3(2):75-86).

Inclusion of a costimulatory receptor may be necessary to achieve full activation of the modified immune cell. Thus, in some embodiments, the CAR comprises additional costimulatory receptors, such as CD3-zeta, FcR, CD27, CD28, 4-1BB (CD137), DAP10, and/or OX40 (CD134). In some embodiments, additional co-stimulatory molecules (e.g., chemokines, chemokine receptors, cytokines, and cytokine receptors) are co-expressed with the CAR in the immune cell.

There are four main classes or "generations" of CARs. "First generation" CARs are typically composed of an antibody-derived antigen binding domain (e.g., a scFv) fused to a transmembrane domain, fused to an intracellular signaling domain. First generation CARs typically comprise an intracellular signaling domain derived from the CD3 ζ-chain, which is the primary signal transmitter in endogenous T cell receptors. "Second generation" CARs add intracellular signaling domains from various costimulatory protein receptors (e.g., CD28, 41BB, ICOS, OX40) to the cytoplasmic tail of the CAR to provide additional signals to the T cell. "Third generation" CARs combine multiple costimulatory domains, such as CD28-41BB or CD28-OX40, to augment T cell activity. "Fourth generation" CARs (also known as TRUCKs or armored CARs) include additional factors that enhance T cell expansion, persistence, and anti-tumoral activity. This can include cytokines, such is IL-2, IL-5, IL-12 and costimulatory ligands. The CARs used with present invention may be from any generation of CAR. In some embodiments, the CAR comprises a CD3ζ intracellular signaling domain.

The CARs used with the present invention may comprise any suitable transmembrane domain from a human transmembrane signaling protein. Suitable transmembrane domains include, without limitation, the human $IgG_4Fc$ hinge and Fc regions, the human CD4 transmembrane domain, the human CD28 transmembrane domain, the human CD3ζ transmembrane domain, and a cysteine mutated human CD3 transmembrane domain.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

EXAMPLES

Example 1

The following Example, the inventors demonstrate that the protein CST6 inhibits multiple myeloma (MM) cell growth and reduces MM cell-induced bone destruction.

MM is a plasma cell malignancy that is characterized in its early stages by its absolute dependence on its bone marrow microenvironment. Contacts made by MM cells with stromal cells, especially osteoclasts (OCLs) and osteoblasts (OBs), are essential for growth, survival, and drug resistance.

Based on concordant gene expression signatures, the inventors have classified MM into 8 distinct molecular entities. They are particularly interested in one of these subgroups, referred to as low bone (LB) disease, because this subgroup has a superior event-free survival and overall survival following high-dose therapy and stem cell transplantation and exhibits significantly less bone disease than all the other subgroups. By analyzing gene expression profiling (GEP) and RNA-sequencing data in more than 1,000 myeloma patients, the inventors identified CST6 as the most upregulated gene in the LB subgroup. CST6, a 14-17 kD secretory protein, is a lysosomal protease inhibitor. Overexpression of CST6 in human myeloma cell lines prevents MM cell growth in vitro and in vivo in mice. In addition, purified CST6 protein from conditioned media of CST6-overexpressing MM cells inhibits MM cell growth and RANKL-induced osteoclast differentiation, decreases MM cell-induced bone destruction, and extends MM mouse survival. Mechanistic studies indicate that CST6 abrogates the alternative NF-κB signaling pathway evidenced by a decrease in nuclear p52 protein in CST6-treated osteoclast precursors. Based on gene expression data and their experimental confirmation, the inventors believe that the autocrine small protein CST6 can be used clinically to target MM cells and prevent bone damage in MM.

Results:

CST6 is Significantly Upregulated in the Low Bone (LB) Subtype of Myeloma Disease We have classified MM into 8 distinct molecular entities[1]. We are particularly interested in one of these subgroups called low bone (LB) disease, because this subgroup has a superior event-free and overall survival following high-dose therapy and stem cell transplantation as well as with significantly less bone disease than all the other subgroups. CST6 expression in $CD138^+$ MM cells was examined in 8 myeloma subtypes using Affymetrix U133Plus2 microarray and correlated with bone focal lesions determined by magnetic resonance imaging (MRI) in 351 newly diagnosed MM patients enrolled in the total therapy 2 (TT2) clinical trial. CST6 expression is significantly higher in the lowest bone lytic lesion subtypes LB (30%) and MF (40%) compared with the remaining groups (FIG. 1A; P<0.001). We further verified this discovery in 245 myeloma patients enrolled in the TT2 clinical trial who also were scanned by both fluorine-18 fluorodeoxyglucose positron emission tomography (FDG-PET) scan and computerized tomography (CT) scan in 244 MM patients. CST6 levels were negatively correlated with focal lesions, as assessed by both FDG-PET and CT. On FDG-PET and CT tests, 72 cases showed no detectable bone lytic lesion, 118 cases had one or two lesions, and 55 cases had three or over lesions. CST6 levels were higher in purified MM cells from patients without bone lytic lesion than those who had one or more lesions on FDG-PET and CT (FIG. 1B; one-way ANOVA for three groups' comparison, P<0.001; 0 lesion vs. 1~2 lesion, P=0.0017; 1~2 lesions vs. >=3 lesions, not significant (NS)). These data suggest that high CST6 expression in MM cells correlates indeed with less focal bone lesions in MM patients.

Figure 2:
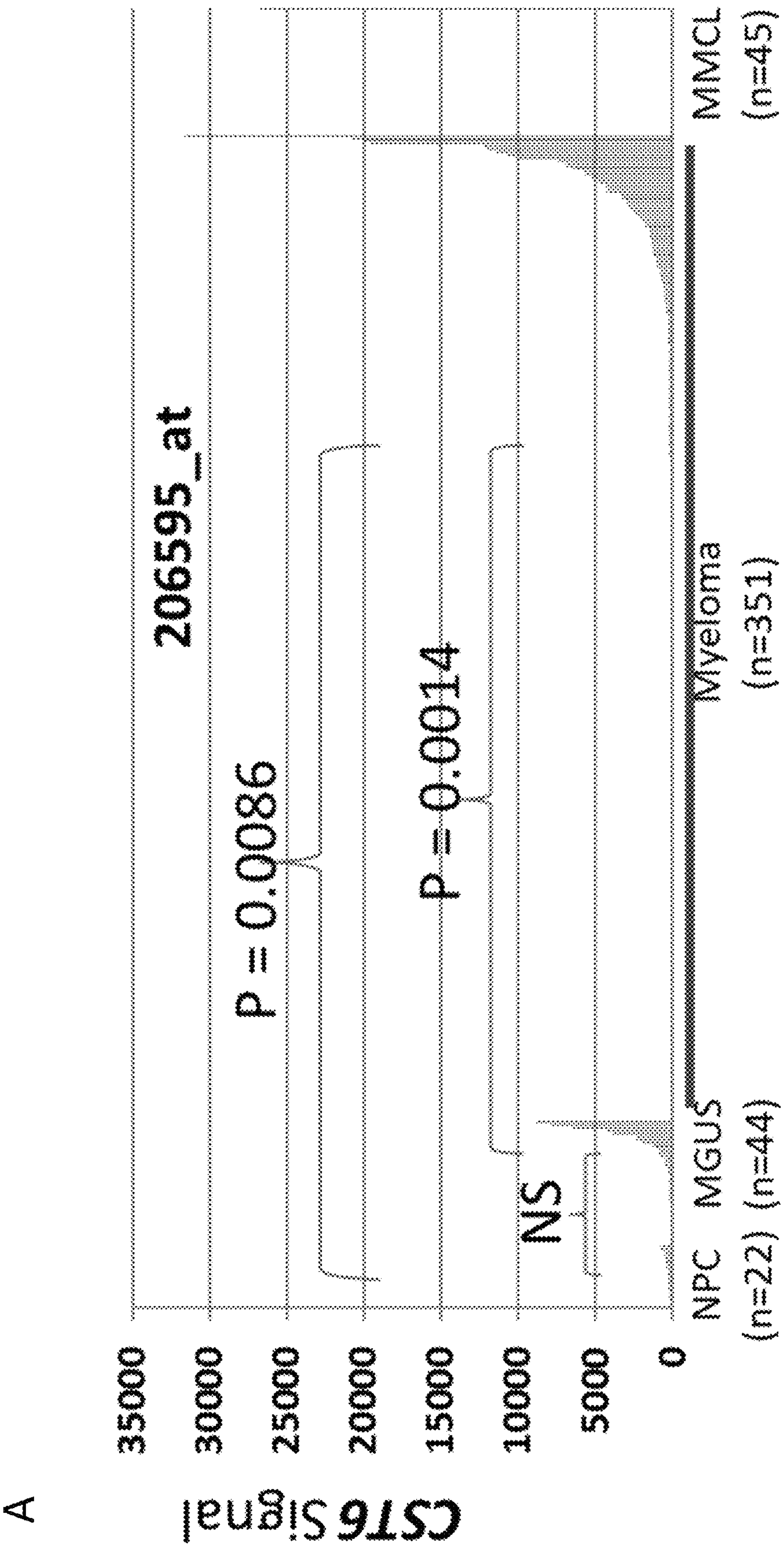
FIG. 2 shows that CST6 expression is increased in tumor plasma cells and is inversely correlated with DKK1 expression in myeloma cells. (A) Increased CST6 expression in MGUS and MM cells compared to normal plasma cells (NPC). The Affymetrix Signal is indicated on the y axis. The level of CST6 expression in each sample is indicated by the height of the bar. Samples from NPC, MGUS, and MM patients are ordered from the lowest to highest level of expression of CST6 from left to right. P values are analyzed by one-way ANOVA (three groups; MM cell lines are not included in the analysis) or a student t test (two groups). (B) Negative correlation between CST6 and DKK1 expression in 351 newly diagnosed MM samples. The Affymetrix Signal is indicated on the y axis. The levels of CST6 and DKK1 expression in each sample are indicated by the height of the bar. Samples from 351 newly diagnosed MM patients are ordered from the lowest to highest level of expression of CST6 (orange bar; 206595_at) from left to right. The expression level of DKK1 is indicated with blue bar (204602_at). The correlation coefficient r value was calculated using a Pearson analysis, and the P value is based on a paired t test. (C) A poor correlation between CST6 mRNA and protein levels is seen in samples from 464 newly diagnosed patients. (D) CST6 mRNA levels showed no relationship with creatinine protein levels. (E) However, there was a strong association between CST6 protein levels and creatinine protein levels, suggesting that Cst6 is affected by renal impairment. (F) Patients were observed with high serum concentrations of cystatin E/M and low DKK1 protein levels.
Figure 2:
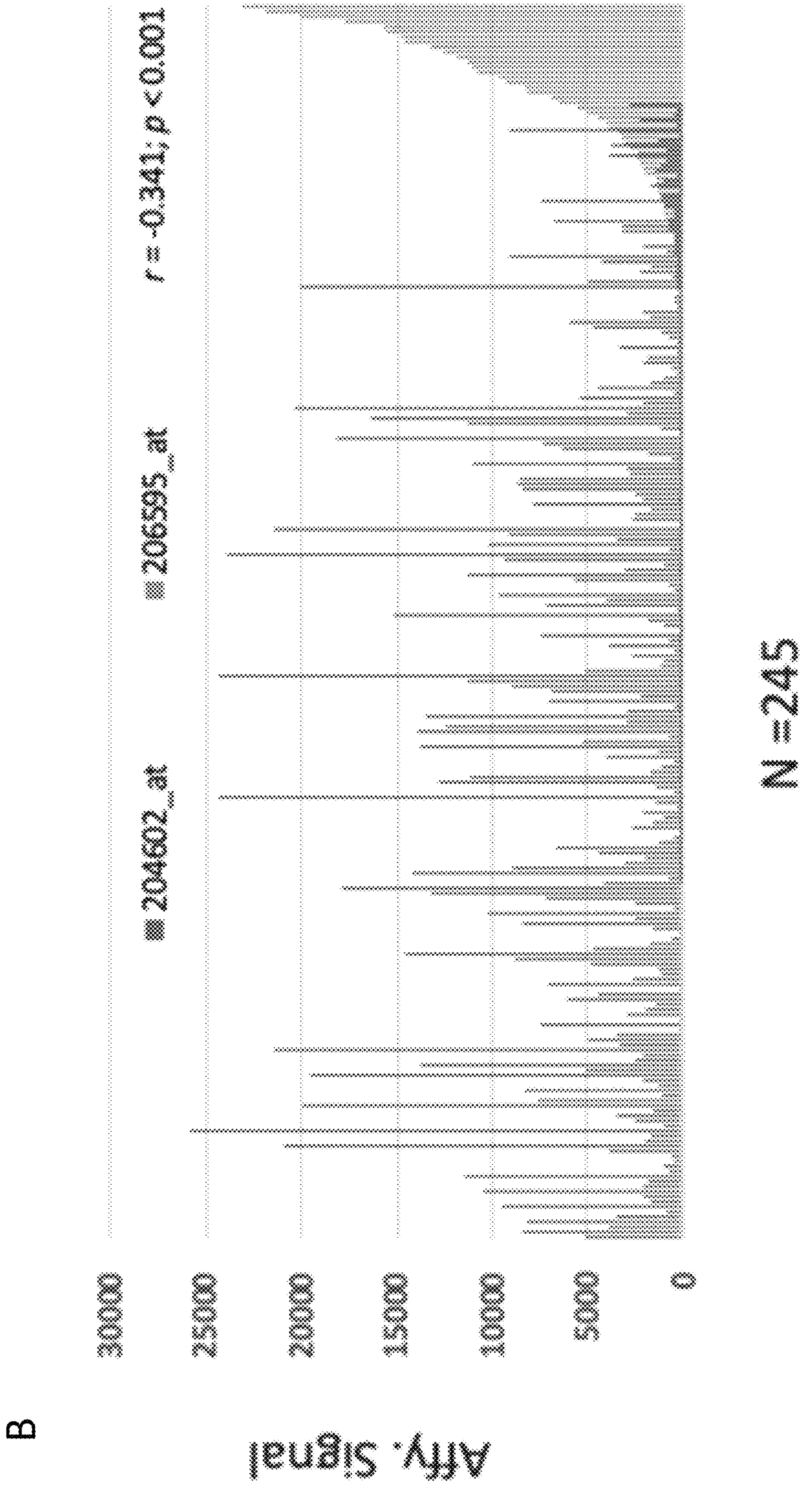
Figure 2:
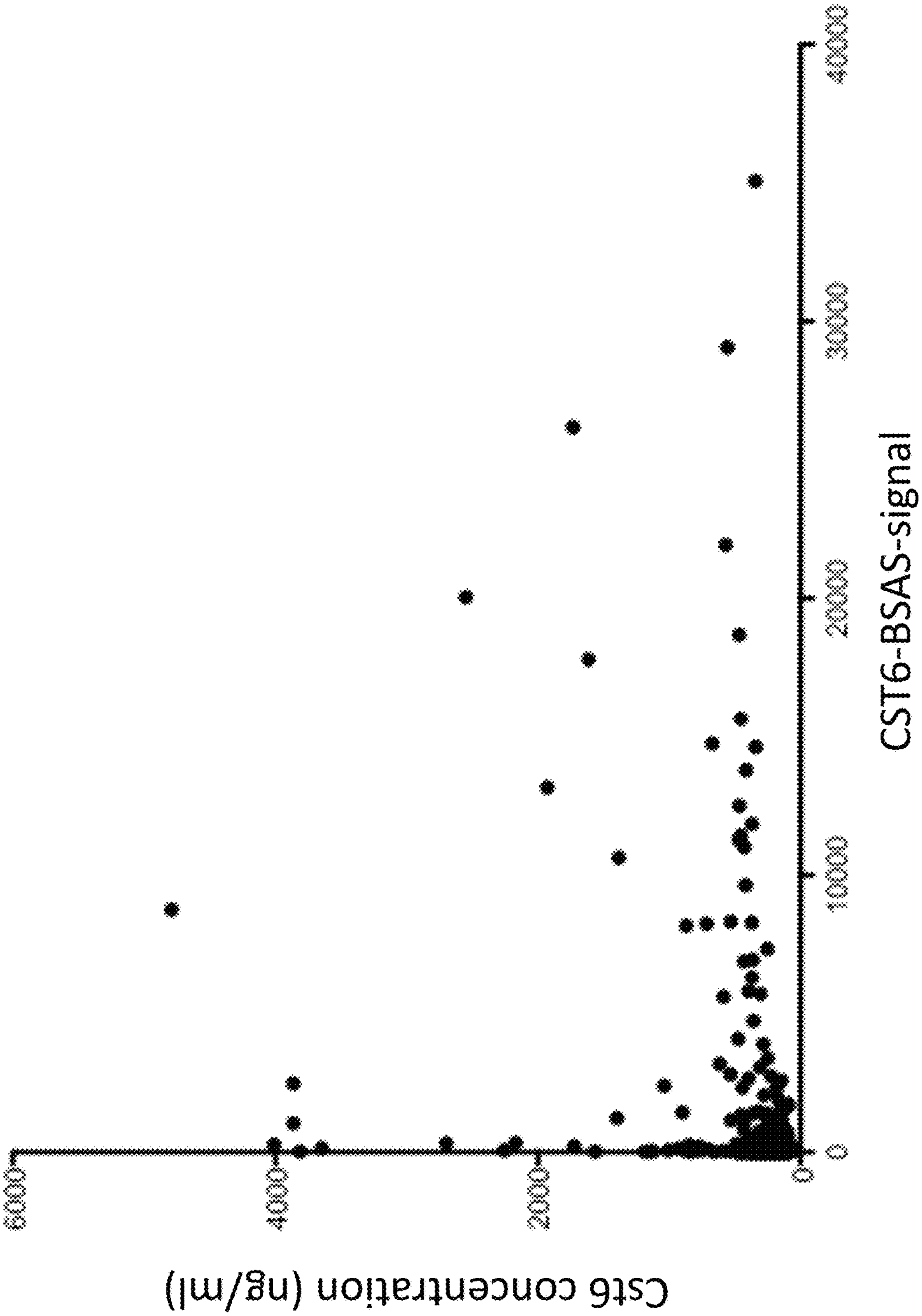
Figure 2:
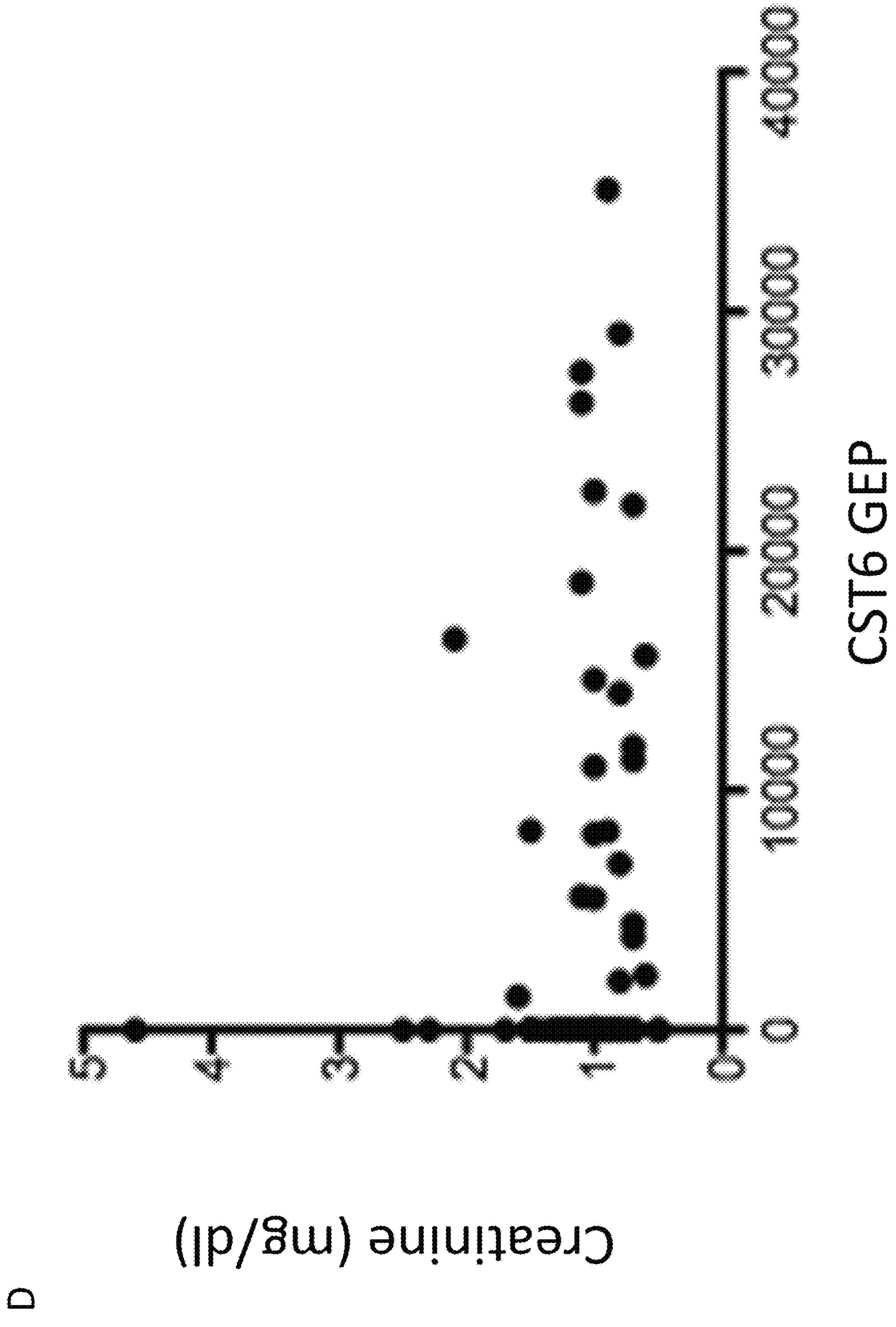
Figure 2:
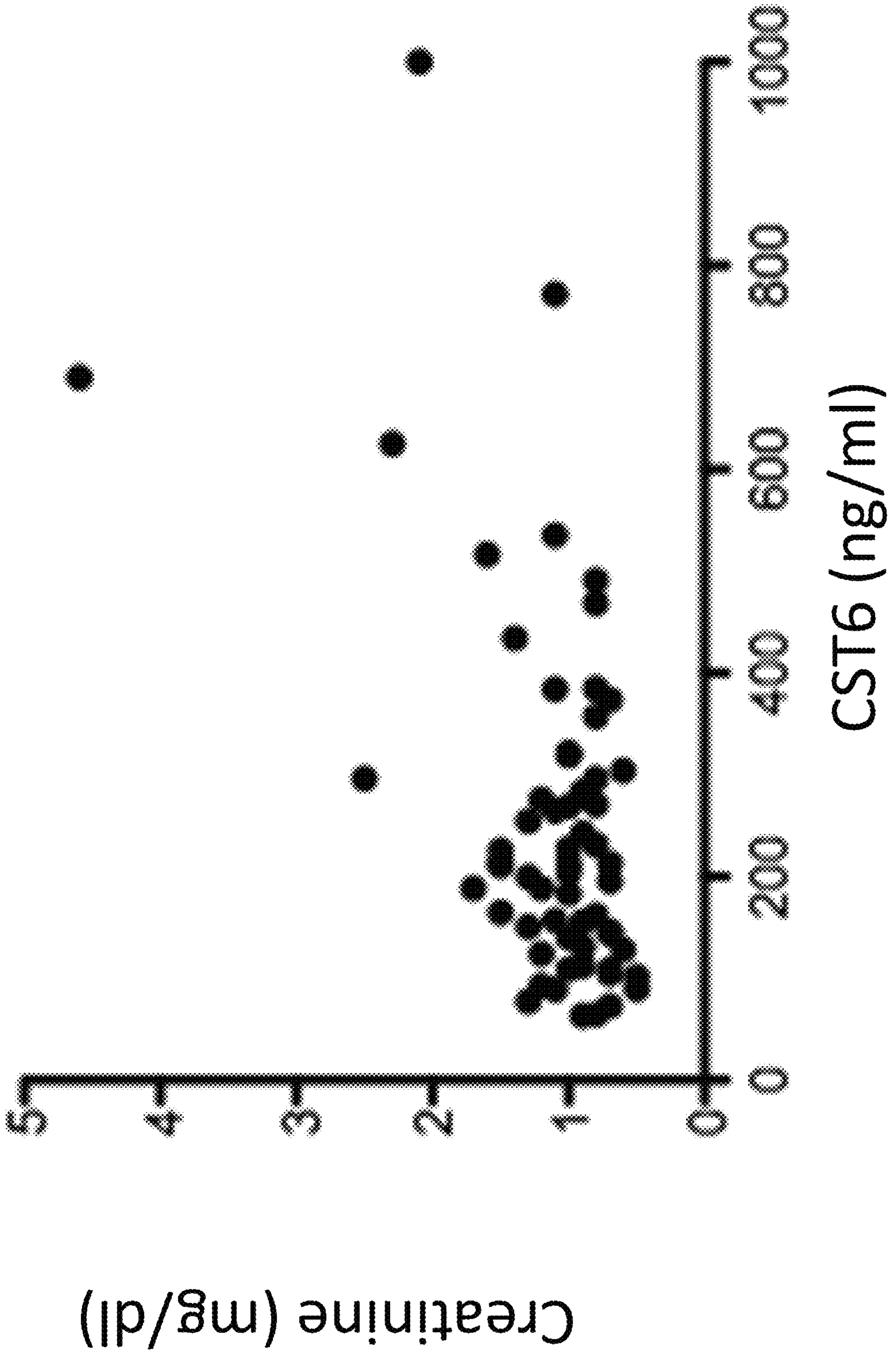
Figure 2:
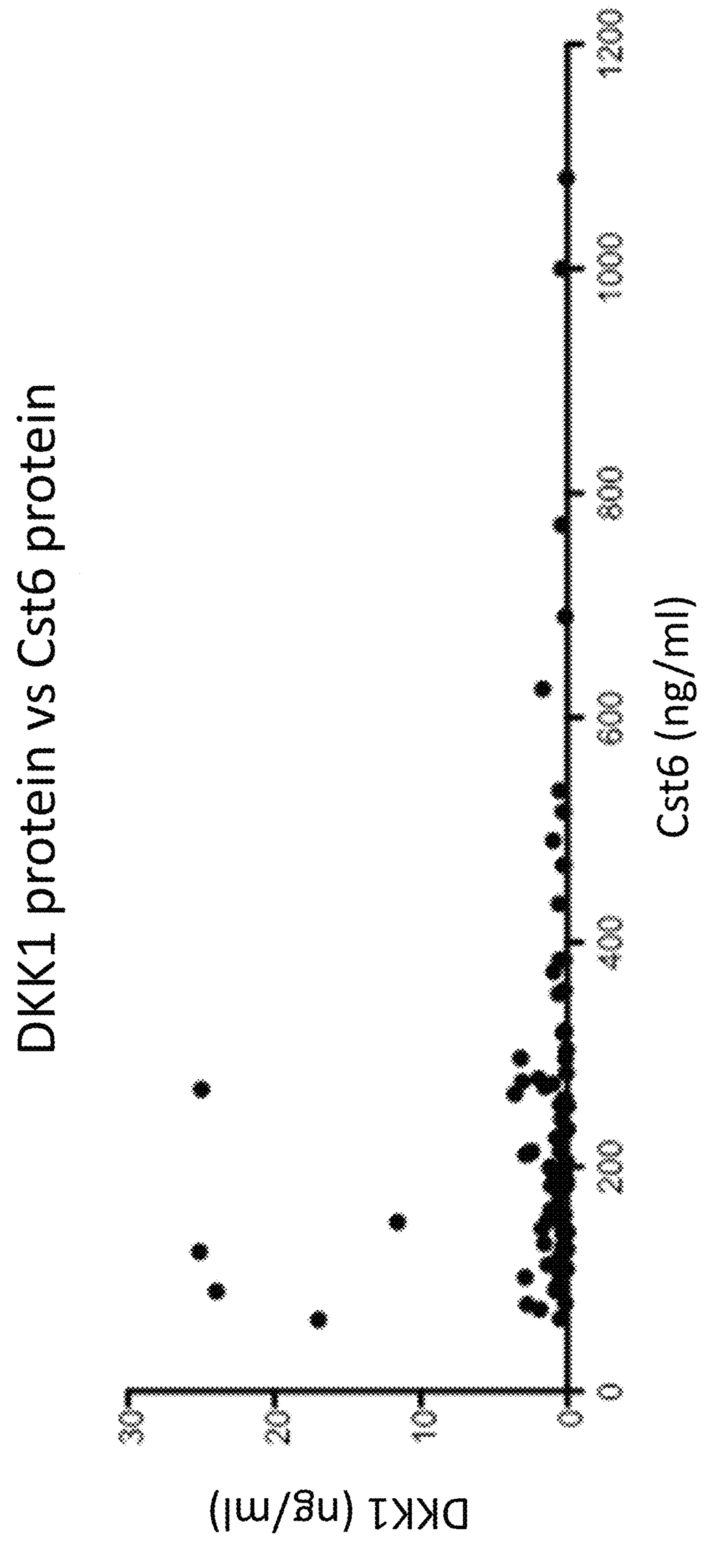

CST6 is Increased in Tumor Plasma Cells Compared to Normal Plasma Cells and is Inversely Correlated with DKK1 Expression in Myeloma Cells We first compared CST6 expression levels in $CD138^+$ plasma cells from 22 healthy subjects (normal plasma cells, NPC), 44 subjects with monoclonal gammopathy of undetermined significance (MGUS), and 351 patients with newly diagnosed MM using Affymetrix microarrays from TT2 clinical trial described above. CST6 was significantly increased in newly diagnosed MM patients compared to NPC samples (P=0.086) and to MGUS samples (P=0.0014), but there was no significant difference between NPC and MGUS (NS) samples (FIG. 2A). Only one (U266) of 45 MM cell lines highly expressed CST6.

We have previously reported that new bone formation in myeloma is almost nonexistent because maturation from mesenchymal cells to osteoblasts is inhibited by DKK1, which binds to the LRP6 co-receptor and inhibits the beta-catenin dependent Wnt signaling[8]. Thus, we then correlated the expression of CST6 with DKK1 using Affymetrix microarrays from 351 purified bone marrow plasma cell populations of TT2 cohort. Myeloma patients with high CST6 showed a significantly decreased DKK1 signal, indicating there is a negative correlation between CST6 and DKK1 expression (FIG. 2B; r=−0.341, P<0.001).

As shown in FIG. 2C there was a poor correlation between CST6 mRNA and protein from 464 newly diagnosed patients. Cystatin C, a class II cystatin similar to CST6, is subject to renal clearance and is reported to be used extensively as a marker of glomerular filtration rate in patients suffering from kidney disease. Thus, to assess whether CST6 serum levels may also be affected by renal impairment in multiple myeloma patients, we performed a correlation analysis of creatinine and CST6 protein levels. 92 of the 464 patients where Cst6 protein was measured in serum samples had previously had a creatinine measurement performed in our hospital. While CST6 mRNA levels showed no relationship with creatinine protein, there was a strong association between CST6 protein and creatinine, suggesting that Cst6 is affected by renal impairment (FIG. 2D & 2E). Although the correlations between CST6 mRNA and protein was poor we still observed patients with high serum concentrations of CST6 had low Dkk1 protein levels (FIG. 2F).

CST6 Inhibits Myeloma Cells-Induced Bone Damage Using an Ex Vivo Model

Figure 3:
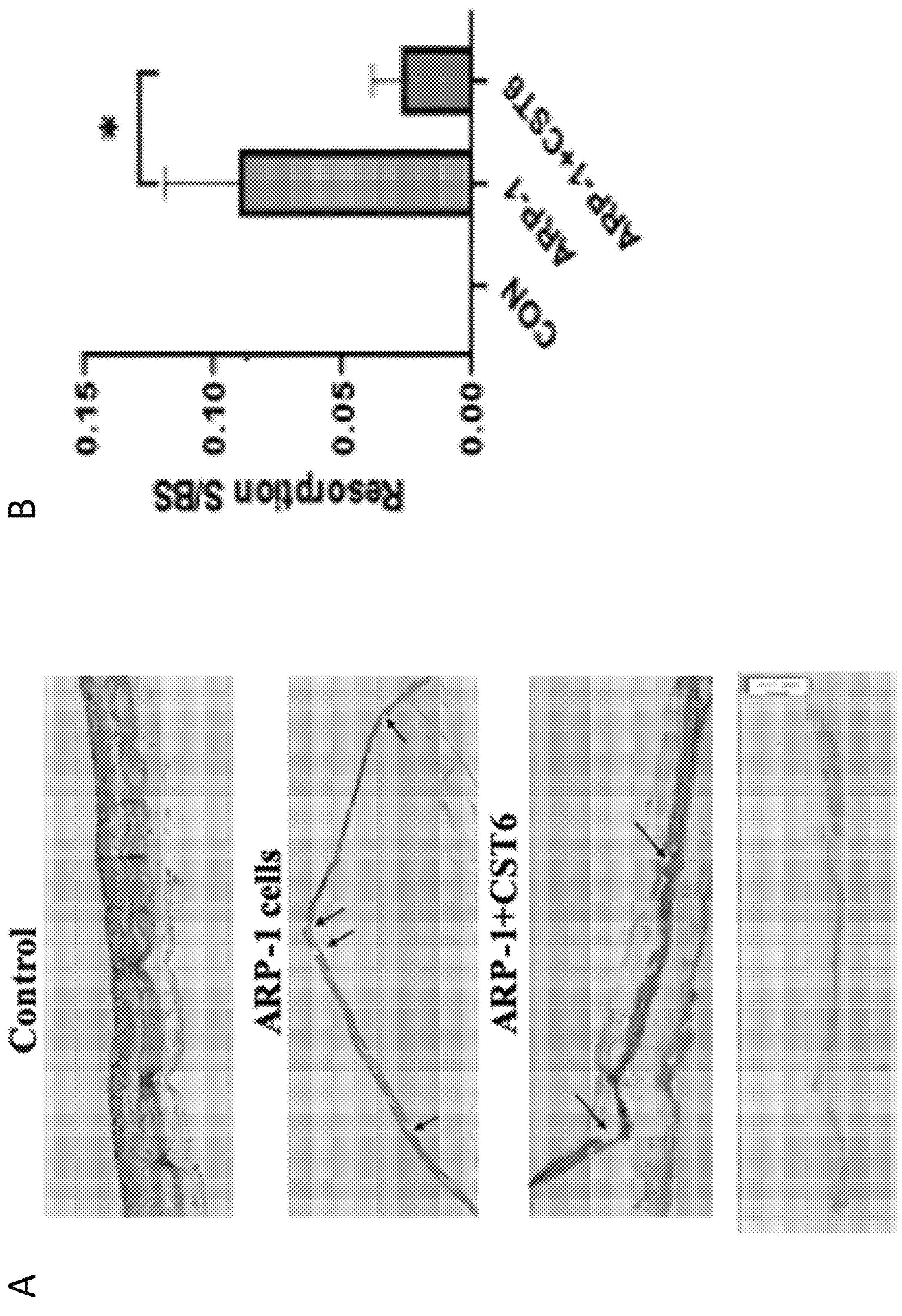
FIG. 3 shows that recombinant CST6 protein reduces myeloma cell-induced bone resorption in calvariae ex vivo. (A) ARP1 MM cells were cultured on calvariae and the calvariae were fixed, decalcified, sectioned, and processed for H&E staining. Three non-overlapping fields per bone were analyzed under 20× magnification for bone resorption (black arrow). (B) Bone resorption was quantified by calculating the resorption surface to bone surface (S/BS) ratio from the ex vivo organ culture system.

To determine the impact of CST6 on MM-associated osteolytic lesions, an ex vivo organ culture system was used to detect bone resorption ex vivo[6]. ARP1 MM cells transfected with CST6 or empty vector were cocultured with calvariae for 10 days, after which the calvariae were histologically analyzed. The Bioquant Image Analysis software was used to quantify mean resorption surface to total bone surface ratio. As shown in the FIGS. 3A and 3B, absence bone lytic lesion was observed in the calvariae cultured with regular media, and the addition of recombinant mouse CST6 protein to ARP1 MM cells significantly decreased the resorption surfaces on calvariae compared to ARP1 cultured alone (black arrows; $P<0.05$). This result demonstrates that CST6 protein can block MM cells-induced bone lytic lesions.

Recombinant CST6 Protein Suppresses Osteoclast Cell Differentiation

Figure 4:
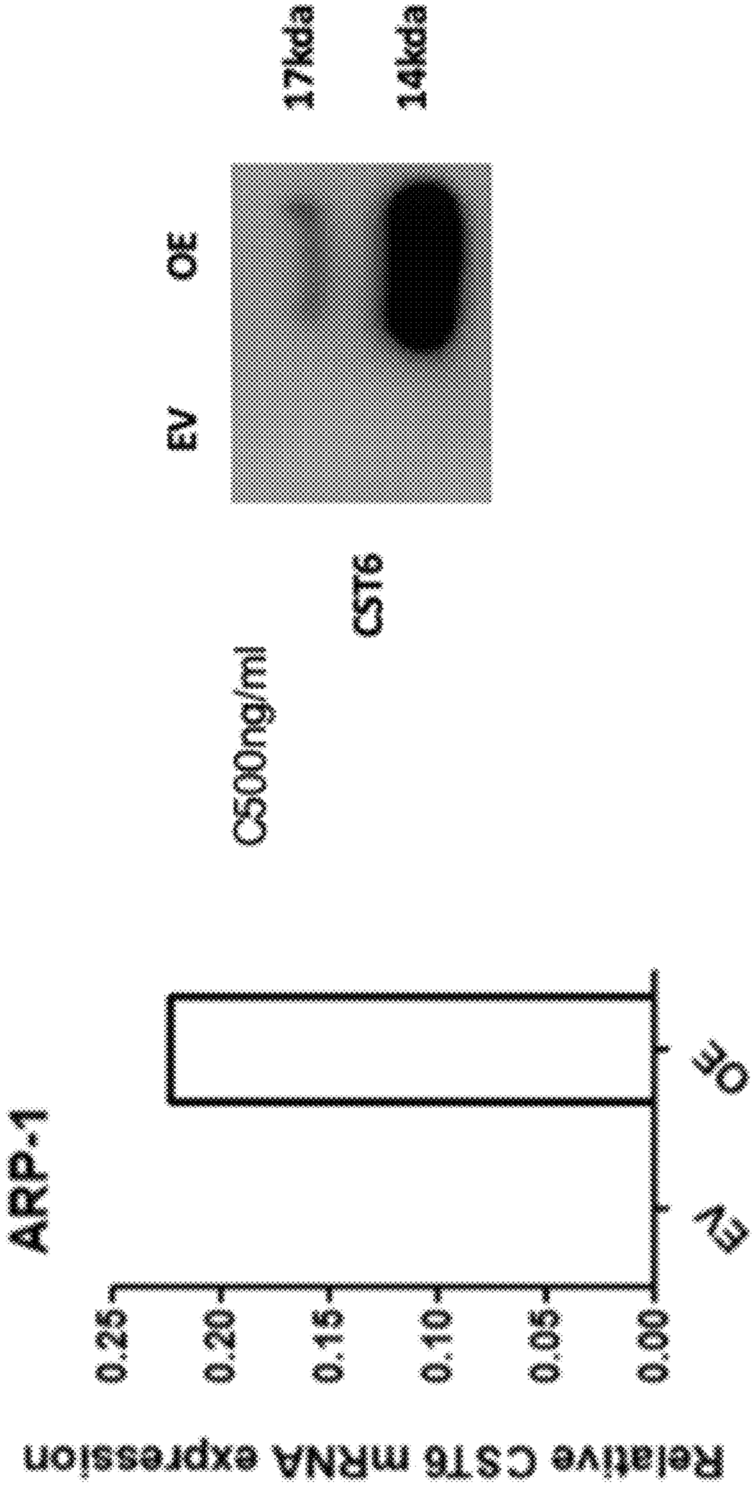
FIG. 4 shows that recombinant CST6 protein inhibits osteoclast cell differentiation. (A) Purification of CST6 protein from ARP1 MM cells overexpressing full-length CST6 cDNA. The expression of CST6 was detected by real-time PCR (left) and western blotting (left). (B) Recombinant mouse CST6 (rmCST6) inhibits RANKL-induced osteoclast differentiation. RAW264.7 macrophages were cultured with RANKL in the presence or absence of rmCST6 protein for 4 days. Osteoclasts were detected by TRAP staining and quantified. The P value is based on a student t test. (C) rmCST6 inhibits primary macrophage differentiation to osteoclasts. Primary bone marrow monocytes from C57BL6 mice were isolated and induced to differentiate into osteoclasts by addition of RANKL. rmCST6 protein was added in the culture media for 5 days. Osteoclasts were detected by TRAP staining. (D) rmCST6 regulates signaling pathways of osteoclast differentiation. The expression of genes related to osteoclastogenesis (i.e., NFATc-1, CTSK, and TRAP) was examined by real-time PCR at different time points. The P value is based on a student t test.
Figure 4:
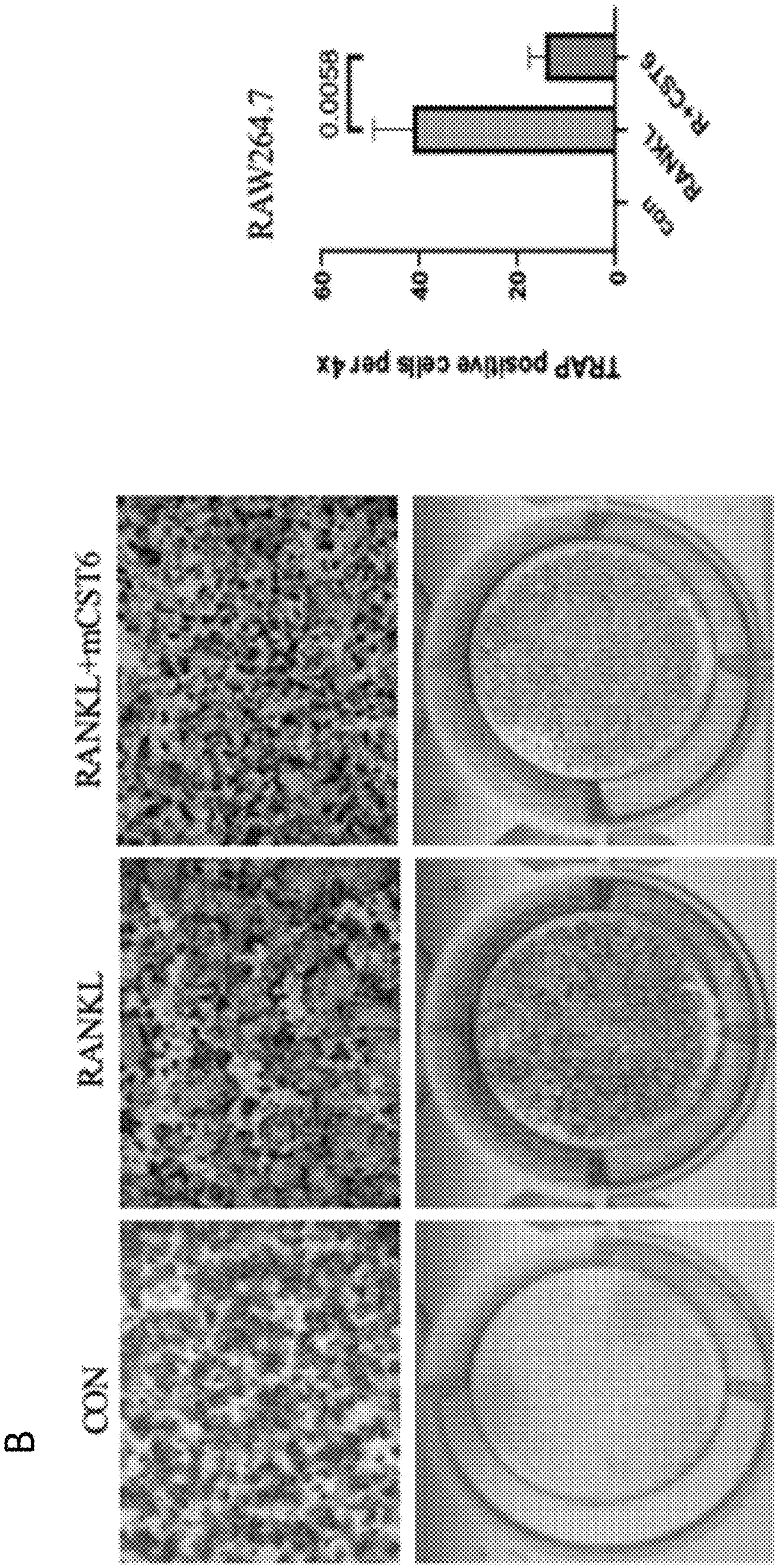
Figure 4:
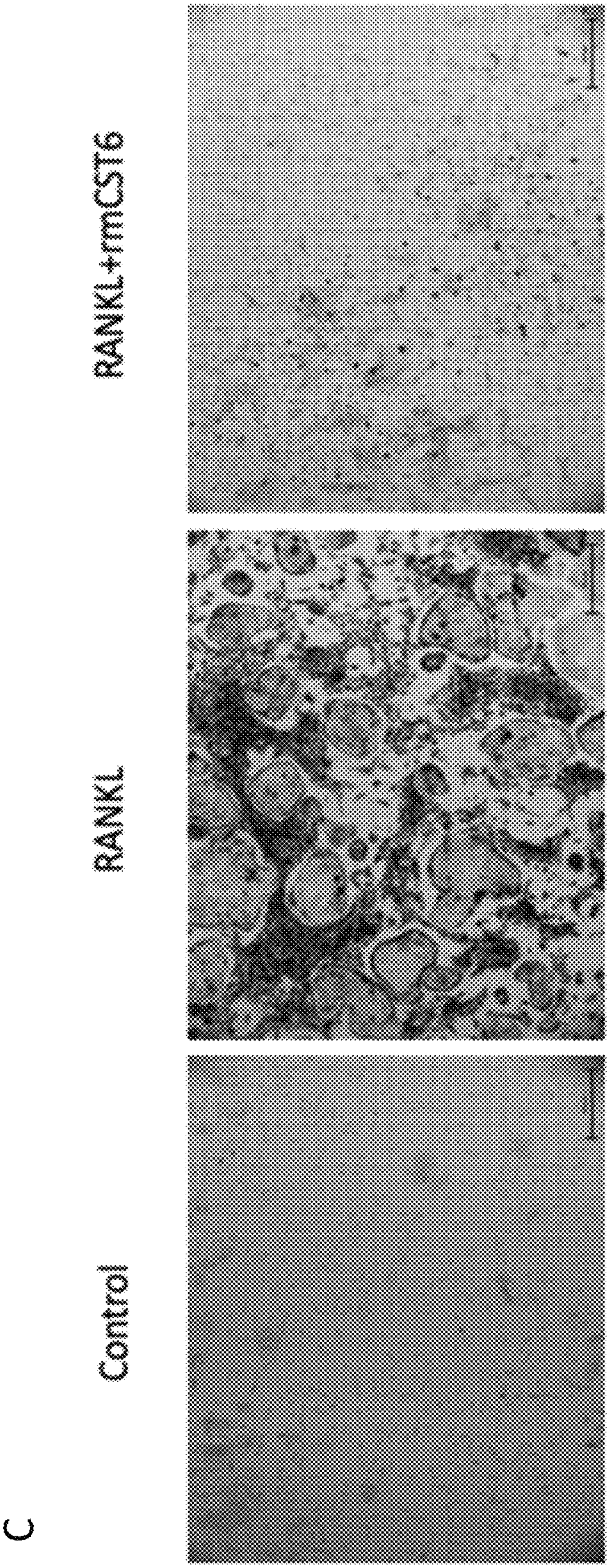
Figure 4:
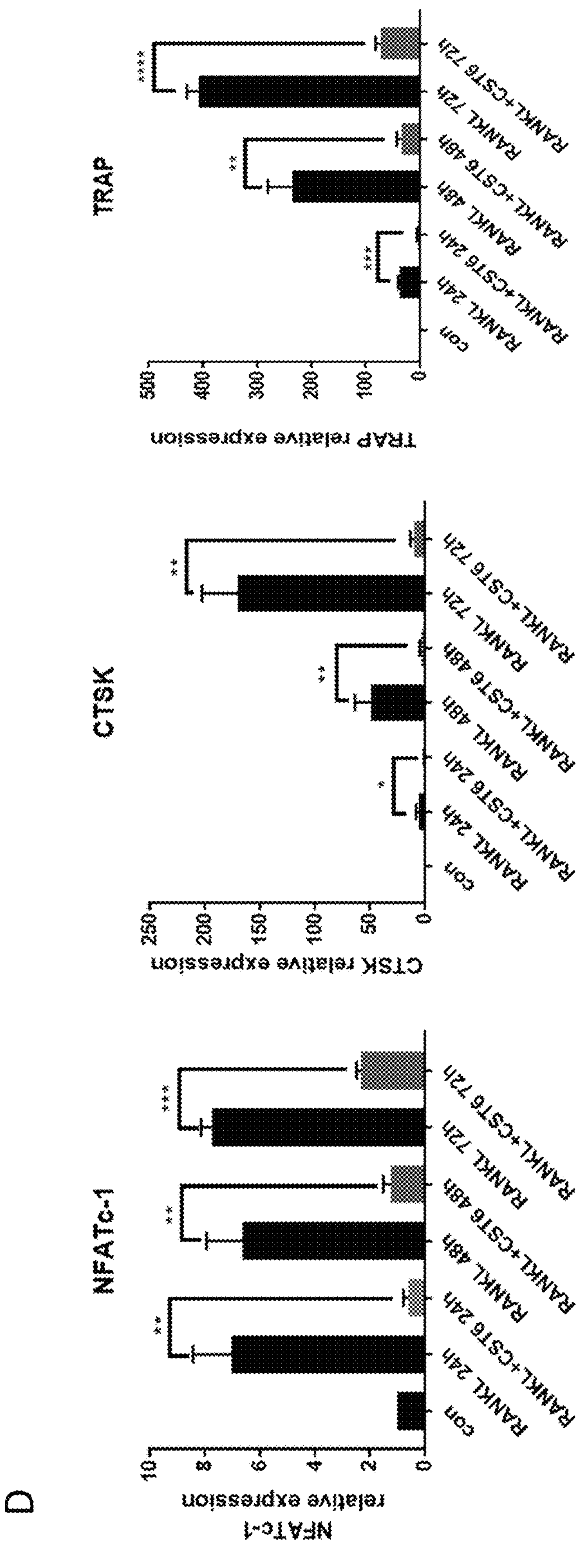

We overexpressed both human and mouse CST6 in the MM cell line ARP1, which was confirmed by increased CST6 expression at both the mRNA and protein levels (FIG. 4A). We then purified CST6 proteins from conditioned media (CM) of ARP1-overexpressing CST6 culture.

The murine macrophage cells RAW264.7 and primary macrophages derived from mouse bone marrow were induced to differentiate to osteoclast by addition of RANKL (50 ng/ml) and M-CSF (10 ng/ml) for up to 3~5 days in a standard protocol. The recombinant mouse CST6 protein was added in the induction media with different doses. TRAP staining showed that addition of CST6 significantly decreased osteoclast differentiation compared with control RAW264.7 cells (FIG. 4B; P=0.0058) and primary mouse macrophages (FIG. 4C). Real-time PCR was used to verify that CST6 protein in RAW264.7 downregulated the expression of CTSK, NFATc1, and TRAP, reliable makers for osteoclastogenesis (FIG. 4D). Together, these results suggest that recombinant CST6 protein inhibits RANKL-induced osteoclastic differentiation, both in RAW264.7 macrophages and primary bone marrow macrophages.

CST6 Inhibits Alternative NF-κB Signaling Pathway in Osteoclast Differentiation

Figure 19:
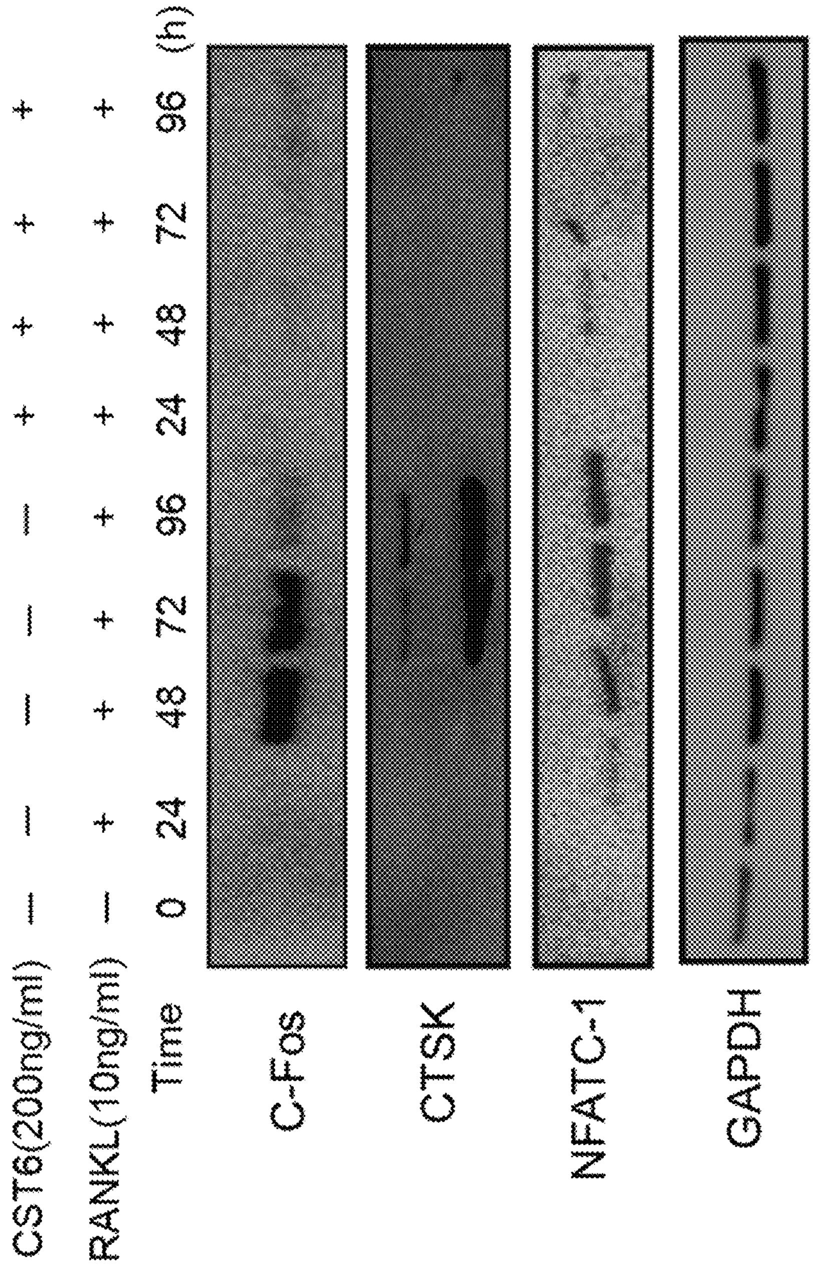
FIG. 19 shows that CST6 inhibits osteoclastogenesis by attenuating RANKL-induced NF-κB signaling pathway. (A) Western blot showing the NFATC-1, c-Fos, and cathepsin K (CTSK) expression levels during osteoclast differentiation in mice treated with or without 200 ng/ml rmCST6. (B) Western blot showing the expression level of IκBα and the phosphorylation of p65 and ERK. (C) Western blots showing the expression level of TRAF3, p100, and p52 in osteoclast precursor cells that were treated with RANKL and/or rmCST6 for 8 hours.
Figure 19:
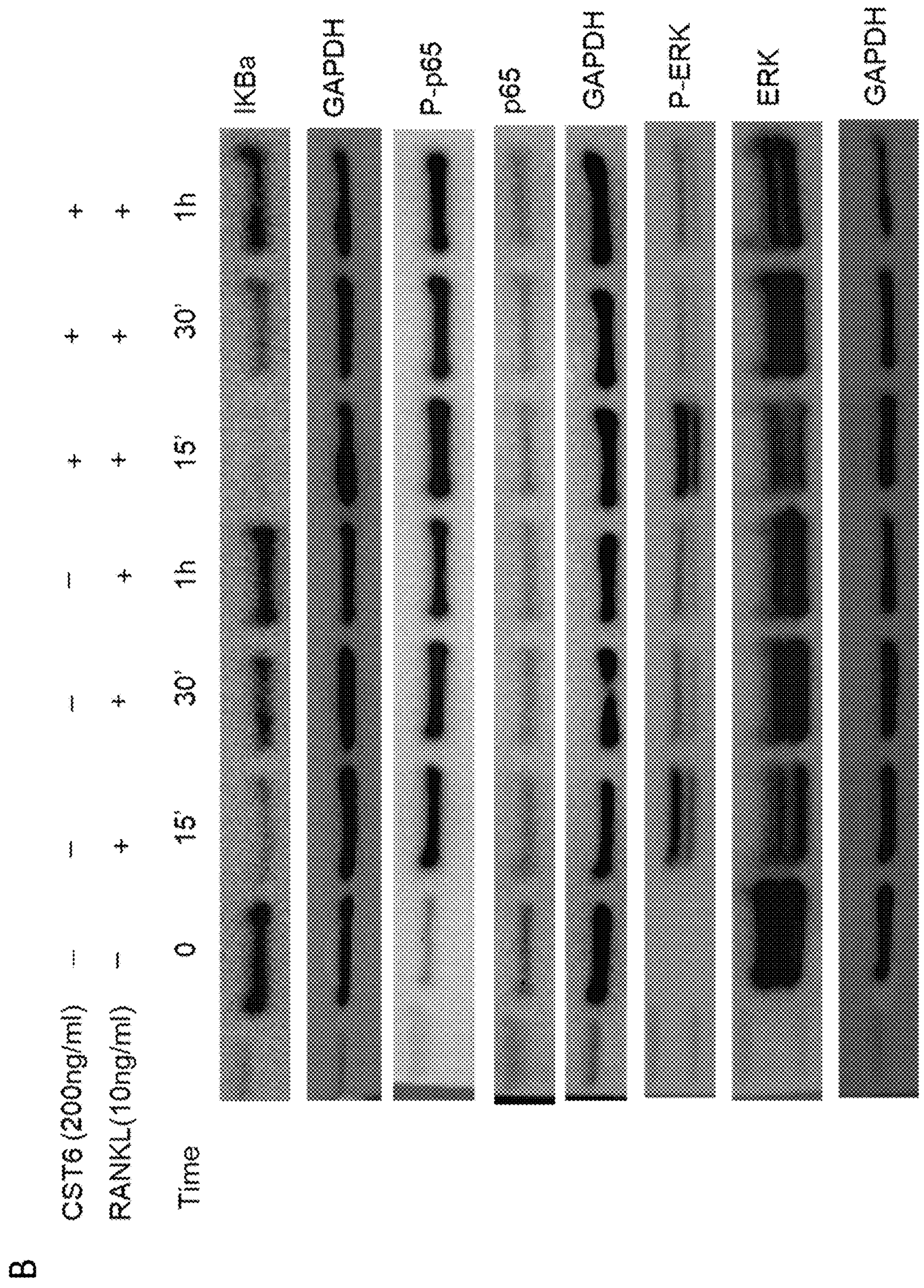
Figure 19:
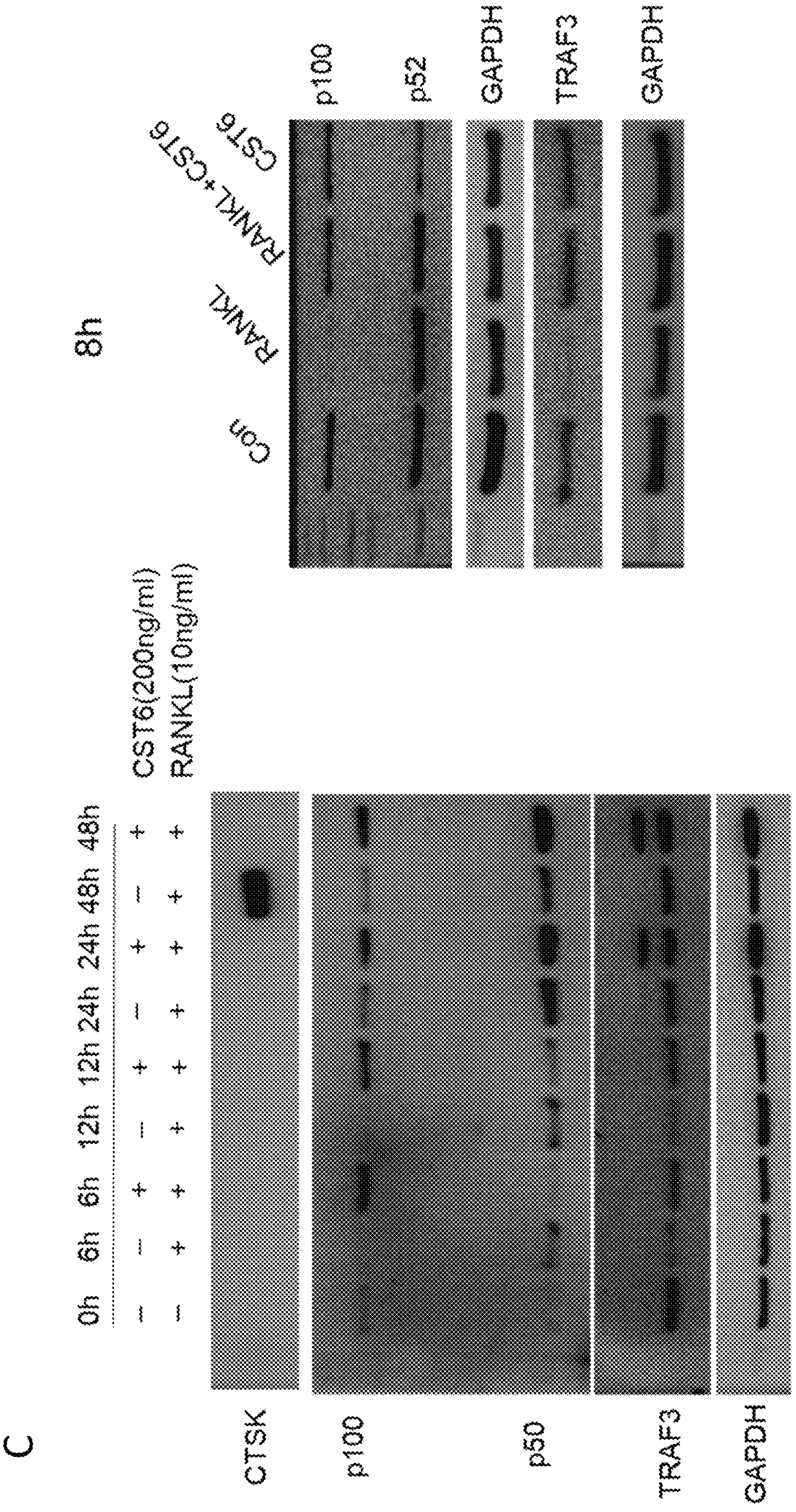

We have shown that the nuclear factor of activated T-cells cytoplasmic 1 (NFATc1), which is a key osteoclastogenesis regulator that is activated by the NF-κB signaling pathway, is significantly inhibited in the CST6 protein treated macrophages. Therefore, we next examined the role of CST6 in both canonic and alternative NF-κB signaling pathways. Nuclear and cytoplasmic fractionations were performed in these RAW264.7 cells with or without CST6 protein in culture. Decreased nuclear p52 (alternative NF-κB pathway), but not p50 (canonic NF-κB pathway), was observed in CST6 protein-treated RAW264.7 cells by western blots (FIG. 19C). The mRNA of cathepsin K (CTSK), a substrate of the cystatin inhibitor CST6, was decreased in CST6 protein-cultured macrophages (FIG. 4C). We then examined CTSK protein levels by western blot. As shown in the FIG. 19A, treatment with CST6 protein also significantly decreased CTSK protein levels after 48 hrs and further decreased 72 hrs after macrophages treated with RANKL.

Recombinant CST6 Inhibits CTSK in Dose Dependent Manner in In Vitro Assays

Figure 5:
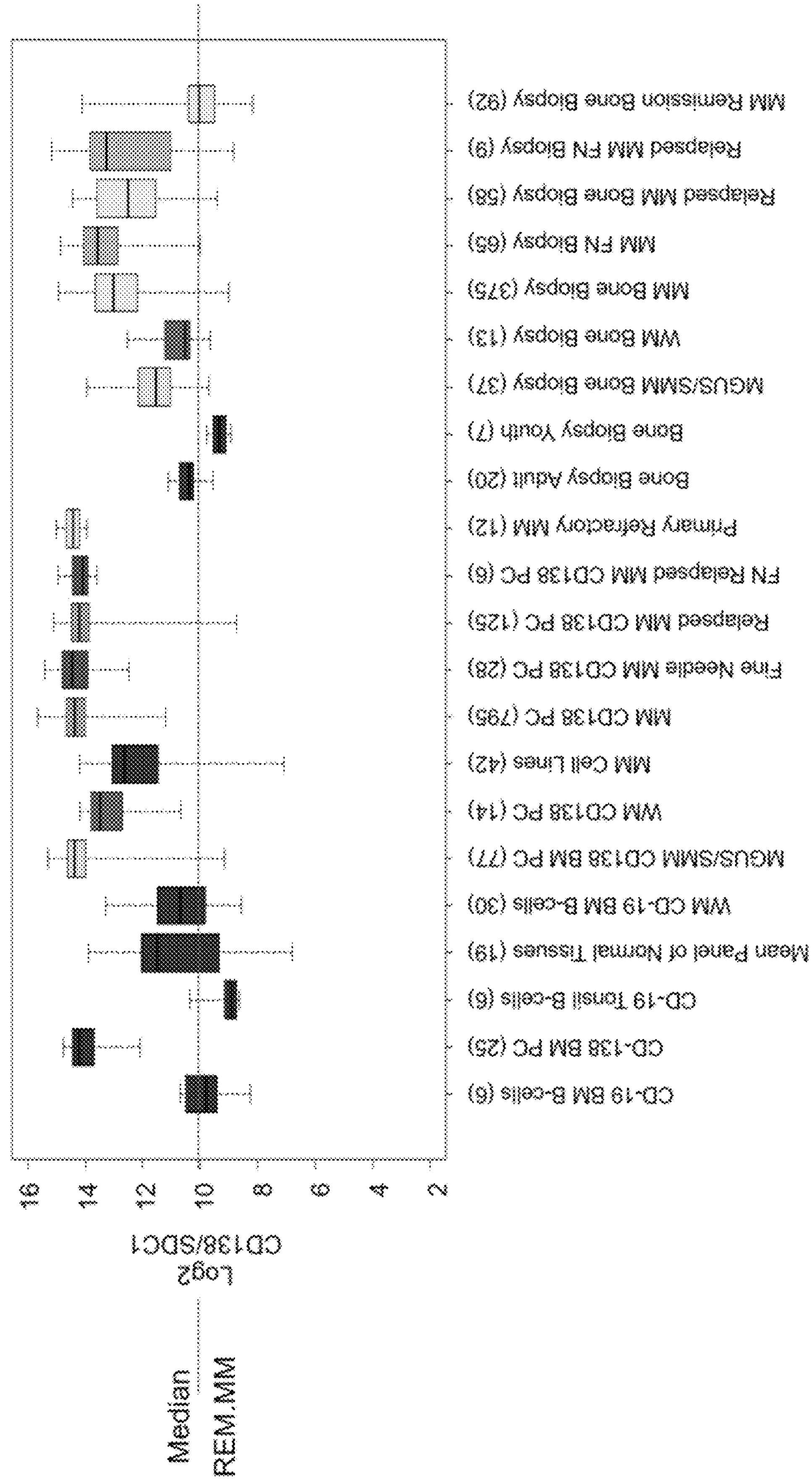
FIG. 5 shows that the plasma cell-specific gene CD138/SDC1 is not expressed in bone biopsies from MM in remission. Boxplots of MAS5 and $Log_2$ transformed U1333Plus2.0 microarray data of syndecan-1/SDC1/CD1338 is shown is a variety of samples, including in purified CD19-selected bone marrow (BM) or tonsillar B-cells, normal tissues, CD138-selected plasma cells taken from the random aspirates of the iliac crest or fine needle aspirates of skeletal focal lesions, whole bone biopsies of the iliac crest or fine needle (FN) biopsies of focal lesions from healthy donors (adult and youth) and patients with Waldenstrom's macroglobulinemia (WM), MGUS/Smoldering MM (SMM), newly diagnosed MM, relapsed MM, refractory MM, and MM in remission. The number of cases in each category is indicated in parentheses.
Figure 6:
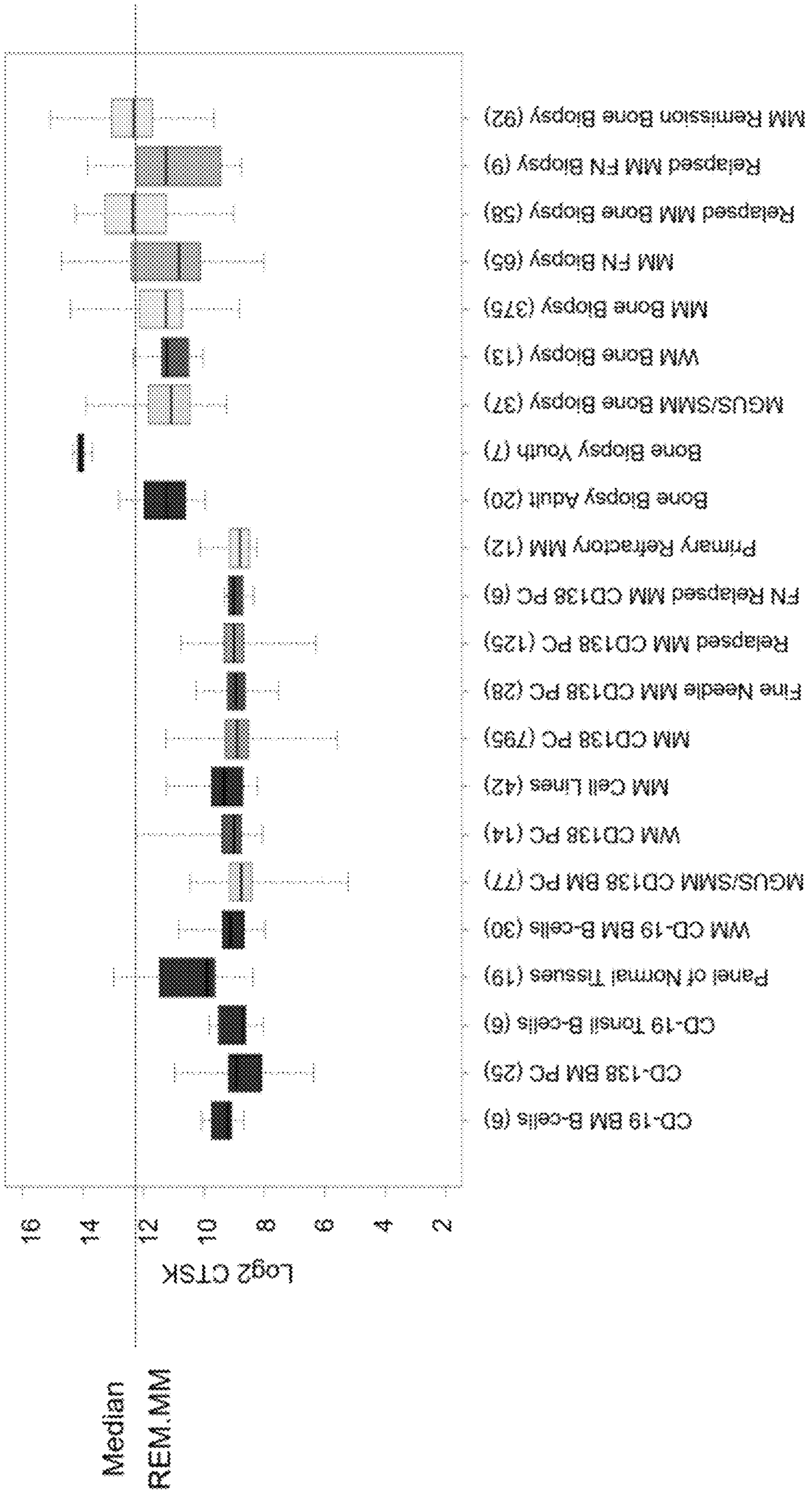
FIG. 6 shows that osteoclast-specific gene cathepsin K is elevated in biopsies from MM in remission. Boxplots of MAS5 and $Log_2$ transformed U1333Plus2.0 microarray data for cathepsin K/CTSK is shown is a variety of samples, including in purified CD19-selected bone marrow (BM) or tonsillar B-cells, normal tissues, CD138-selected plasma cells taken from the random aspirates of the iliac crest or fine needle aspirates of skeletal focal lesions, whole bone biopsies of the iliac crest or fine needle (FN) biopsies of focal lesions from healthy donors (adult and youth) and patients with Waldenstrom's macroglobulinemia (WM), MGUS/Smoldering MM (SMM), newly diagnosed MM, relapsed MM, refractory MM, and MM in remission. The number of cases in each category is indicated in parentheses.

FIG. 5 and FIG. 6 present microarray data showing the mRNA levels of the plasma cell-specific gene SDC1/CD138 (FIG. 5) and osteoclast-specific gene CTSK (FIG. 6) in relevant cell types and show that, while CD138 levels plummet in MM in remission, CTSK levels and, therefore, osteoclast numbers, are elevated in bones of MM in remission, similar to that seen in relapsed MM, suggesting that increased osteoclasts in the bones of MM in remission might contribute to relapsing disease and that suppressing CTSK might aid in the prevention of relapses. FIG. 5 shows the expected high level expression of SCD1/C138 in purified plasma cells and the relatively low level expression in CD-19-selected cells and normal tissues (left side of panel). There is low level expression in whole bone biopsies from healthy adults and youths, higher levels in MGUS/SMM and WM, and still higher levels in bone biopsies and FN biopsies from MM. As expected, expression levels significantly drop in whole bone biopsies from MM in remission to levels below that seen in the biopsies of healthy donors. FIG. 6 further shows the generally low level expression in purified CD19 and CD138 cells with higher expression in normal healthy tissues. There is significantly higher expression detected in whole bone biopsies relative to purified cells while the levels in MM remission bone biopsies is higher than that seen in healthy adult donors, MGUS/SMM, random biopsies, and MM FN biopsies from newly diagnosed MM and similar to that seen in random biopsies from relapsed MM.

Taken together, these data suggests that cathepsin K levels, and therefore osteoclasts, are elevated in the bone marrow of MM in remission and that these levels are similar to that seen in relapsed MM. Suggesting that the elevated levels of osteoclasts in remission marrows could contribute to relapsing disease. Inhibiting CTSK in MM in remission could aid in the prevention of relapses.

CST6 Inhibits Cathepsin K In Vitro

Figure 7:
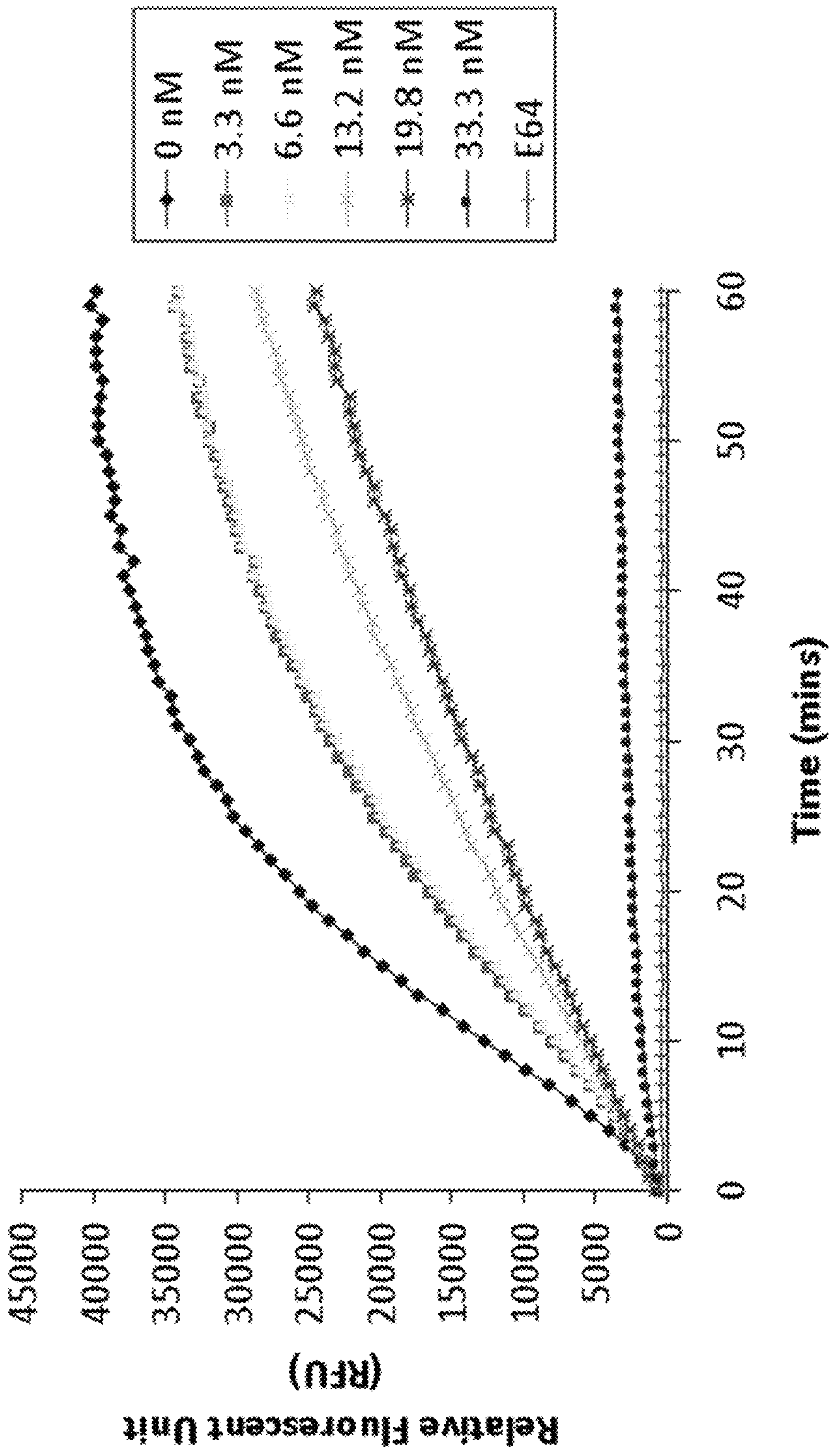
FIG. 7 shows that recombinant CST6 inhibits CTSK in a dose dependent manner in in vitro assays. (A) The ability of recombinant cystatin E/M to inhibit cathepsin K cleavage of a specific fluorogenic substrate was assessed in an in vitro assay. CST6 was able to inhibit cathepsin K in a dose dependent manner with an inhibition constant (Ki) of 3.84 nM. (B) Recombinant Cst6 can inhibit cathepsin K-mediated bone resorption of dentine discs by osteoclasts cultivated from primary mesenchymal stem cells in a bone resorption assay.
Figure 7:
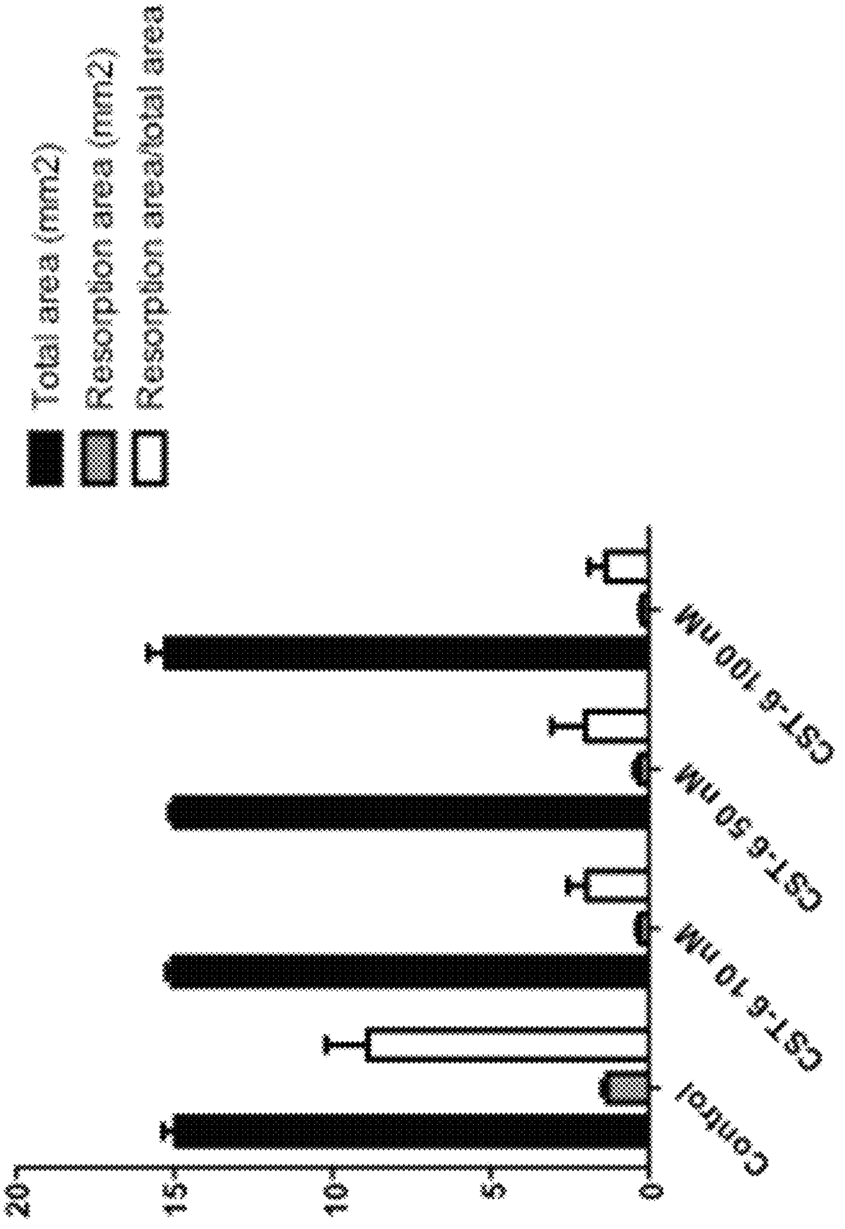

The cysteine protease, cathepsin K, has been previously shown to be the main protease involved in bone resorption. As the CST6 gene encodes cystatin E/M, which is a reported cysteine protease inhibitor, we hypothesized that elevated levels of cystatin E/M in the vicinity of osteoclasts may prevent bone resorption by preventing cathepsin K activity within the ruffled border of the osteoclast. Analysis of the MEROPS database showed the ability of CST6 to inhibit cathepsin K had not been previously studied. Using a similar approach to our previous cathepsin S studies (Burden et al., 2008), we assessed the ability of recombinant cystatin E/M to inhibit cathepsin K cleavage of a specific fluorogenic substrate in an in vitro assay. FIG. 7A clearly shows that CST6 was able to inhibit cathepsin K in a dose dependent manner with an inhibition constant (Ki) of 3.84 nM. The calculated Ki value for inhibition of cathepsin K by Cst6 is close to the Ki values for inhibition of cathepsin K by other class two cystatins measured by Guay and colleagues (2002).

Overexpression Model

Figure 8:
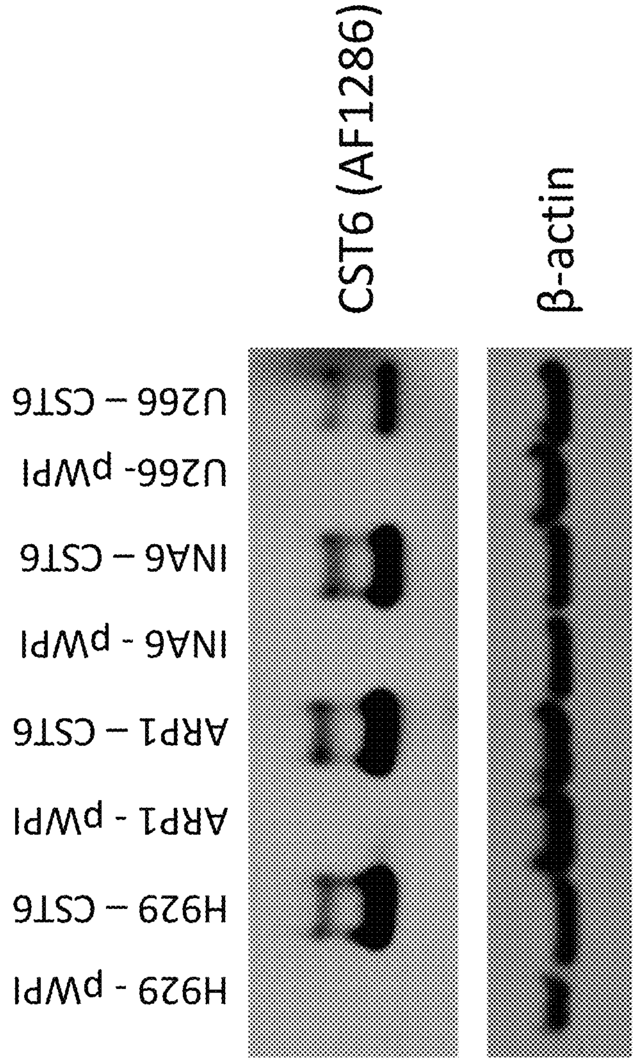
FIG. 8 shows an assessment of intracellular cathepsin activity in multiple myeloma cell lines overexpressing Cst6. (A) Cell lines were screened by western blotting. Both the unglycosylated and glycolsylated forms of cystatin E/M were detected in cell lysates. (B) Results of an ELISA showing that the cystatin E/M protein was being correctly secreted into the supernatant. (C) Conditioned media from the H929 cell line expressing cystatin E/M inhibited cathepsin K activity compared to control cells comprising the empty vector pWPI.
Figure 8:
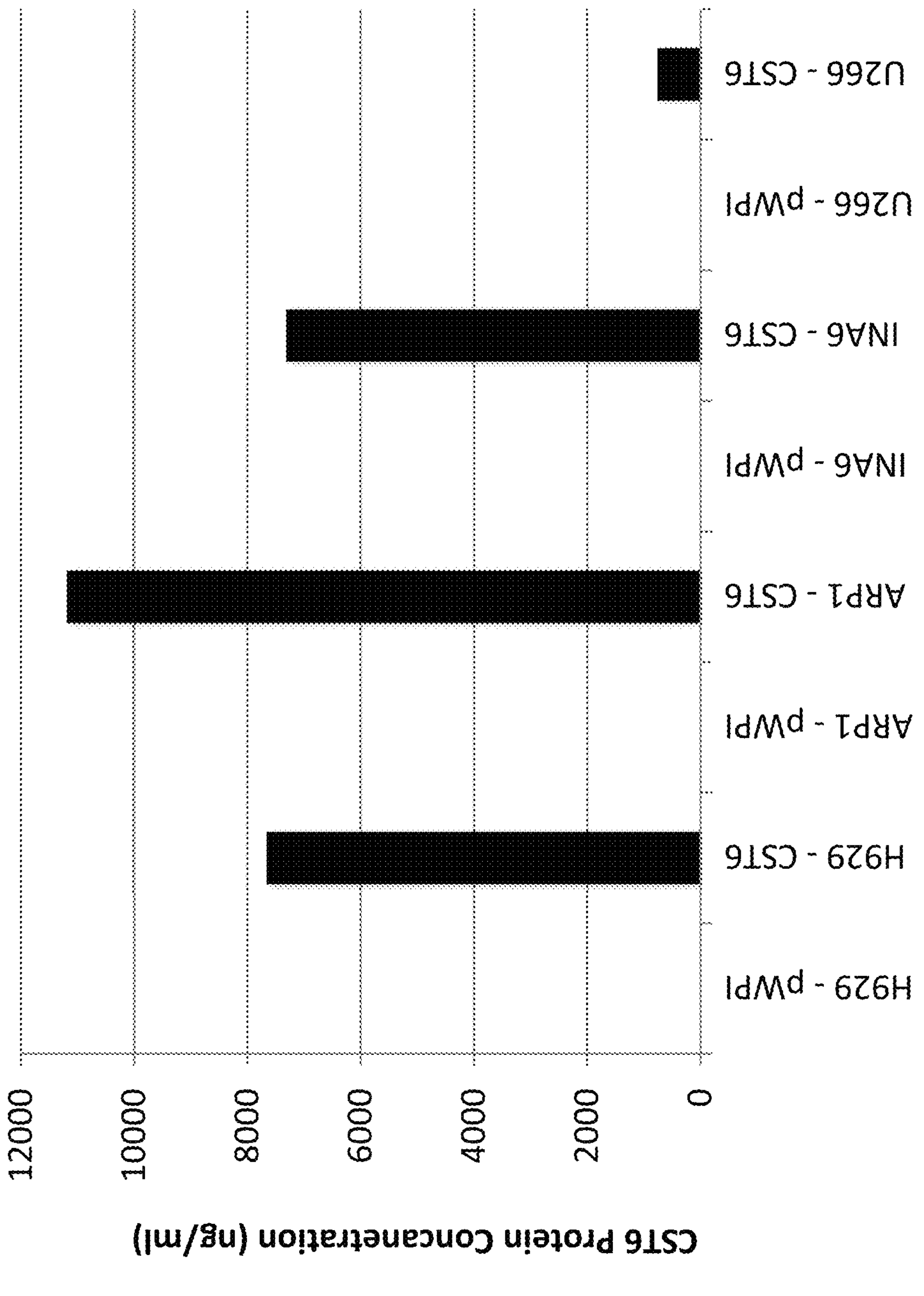
Figure 8:
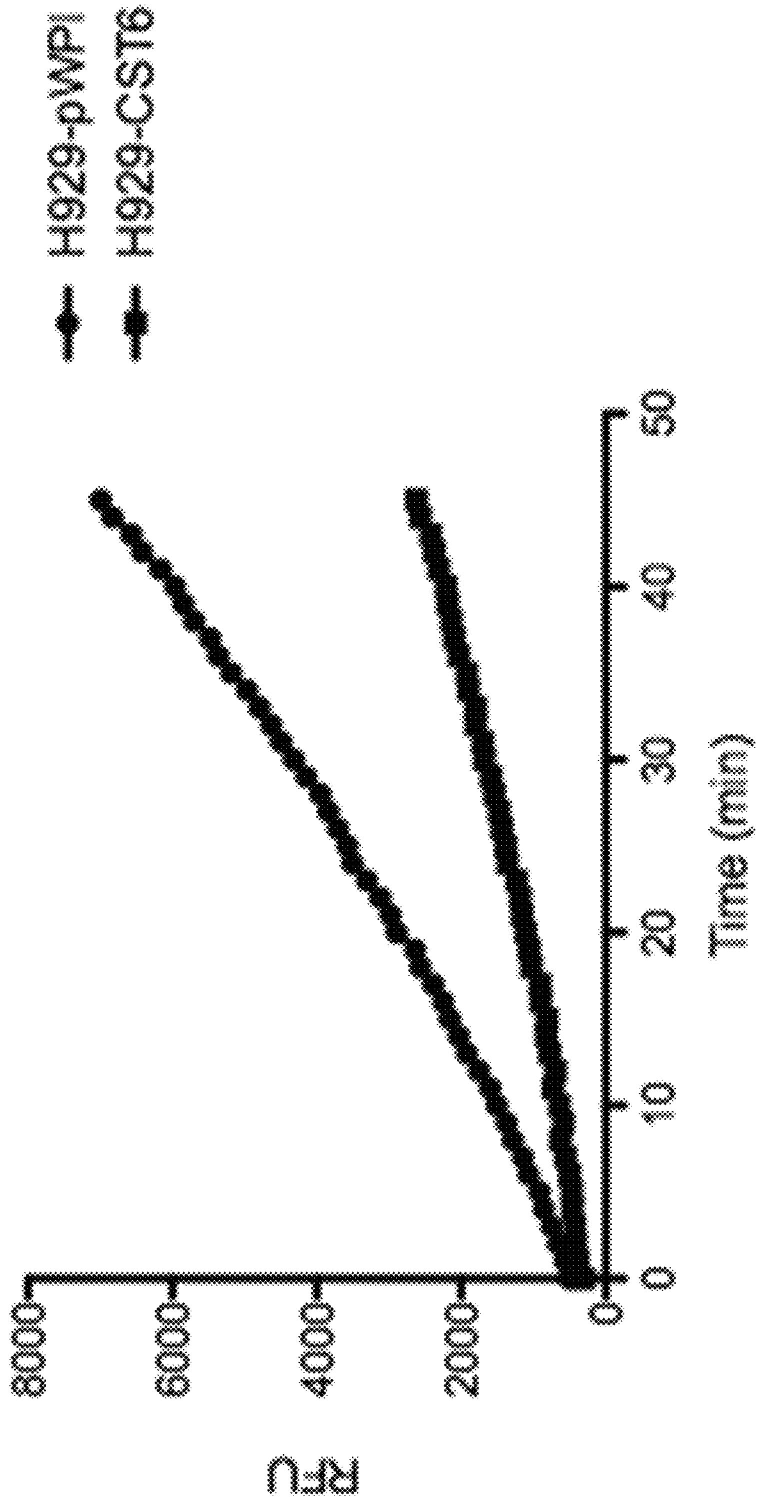

Gene expression profiling and western blotting showed that no MM cell lines expressed CST6 (data not shown). Using our ELISA, we analyzed cystatin E/M expression in conditioned media from a panel of eight multiple myeloma cell lines and were unable to detect the presence of CST6, which was consistent with the gene expression profiling data. Therefore, to examine the role of cystatin E/M, we employed a lentiviral approach to establish a panel of MM cell lines that stably overexpressed cystatin E/M. Cell lines were screened by western blotting and we were able to detect both the unglycosylated and glycolsylated forms of cystatin E/M in cell lysates (FIG. 8A). Using the cystatin E/M ELISA, we confirmed the protein was being correctly secreted into the supernatant (FIG. 8B). Although the manufacturer guidelines state the cathepsin K drug discovery kit was not suitable for biological samples, we were able to adapt the assay using serum free media. Using the H929 cell line expressing cystatin E/M or the empty vector, we show that conditioned media from a cell line with elevated CST6 inhibited cathepsin K activity compared to control cells (FIG. 8

CST6 can Inhibit Intracellular Cathepsin and Legumain Activity

Figure 9:
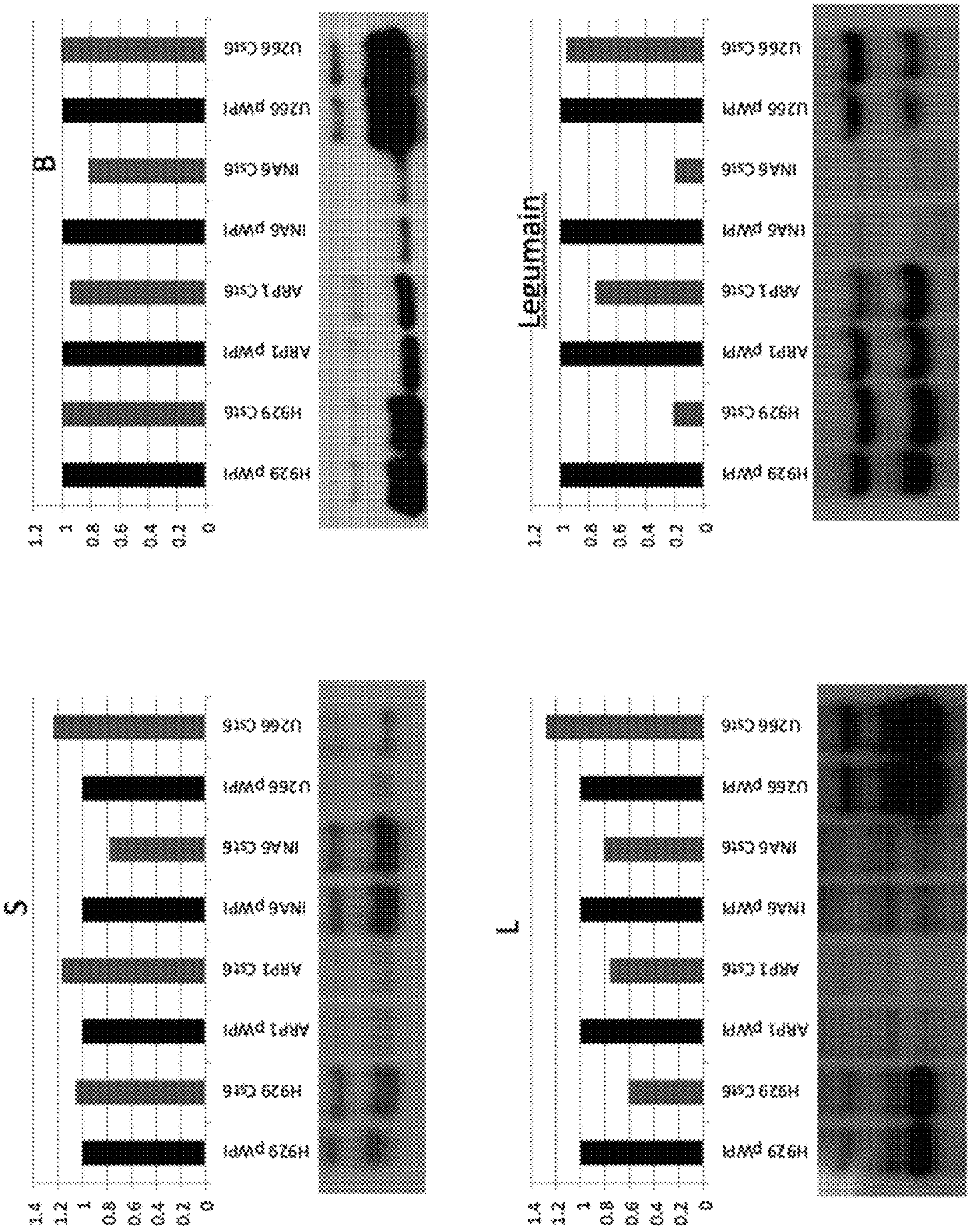
FIG. 9 shows an assessment of intracellular cathepsin activity in multiple myeloma cell lines overexpressing CST6. Activity of cathepsin S and B was not affected by overexpression CST6, whereas cathepsin L and legumain showed a reduction in activity in comparison to cell lines infected with the empty vector. Western blot analysis of the same lysates used for the activity assays confirmed that this reduction in activity was not due to a decrease in protein.
Figure 10:
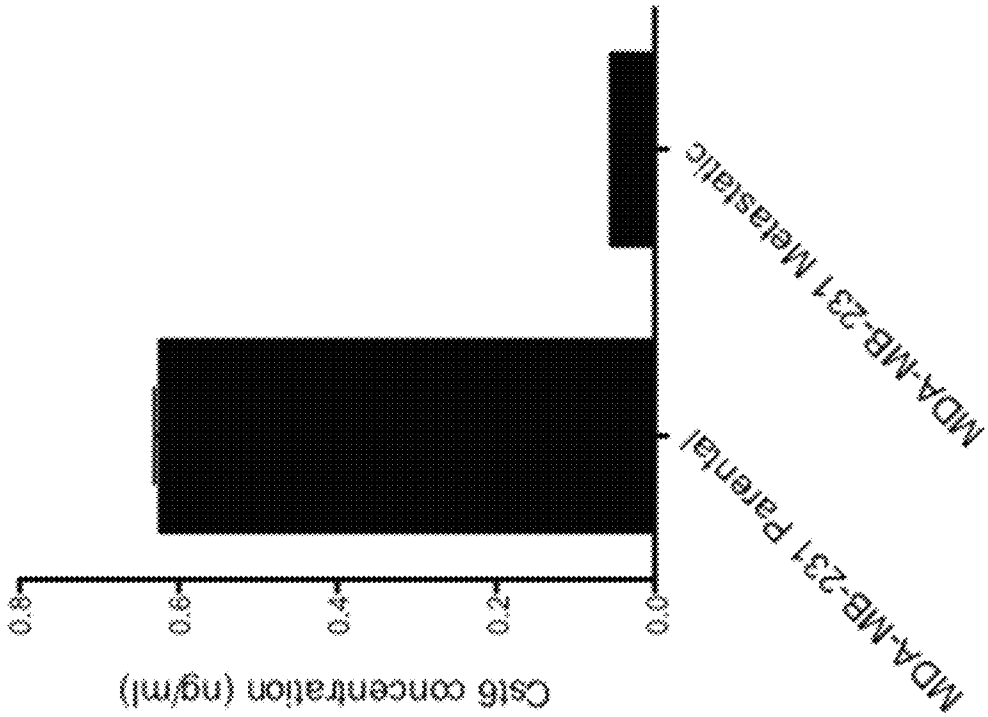
FIG. 10 shows a reduction in CST6 protein in supernatant of MDA-MB-231 Metastatic compared to the parental cell line. CST6 concentration was determined in the supernatant of cell lines.

Forced expression of CST6 can inhibit intracellular cathepsin B and legumain activity in prostate cancer and melanoma (Briggs et al., 2010; Hosokawa et al., 2008). Cathepsins B, L, and legumain are known to be inhibited by cystatin E/M (MEROPS) and cathepsin S is a cathepsin L-like protease which is reportedly involved in the generation of epitopes in antigen presenting cells (Small et al., 2011). Gene expression profiling indicated cathepsins B, L, S, and legumain are expressed in multiple myeloma cell lines and patient samples (data not shown). We therefore examined whether elevated cystatin E/M levels in cell lysates from multiple myeloma cell lines could inhibit intracellular activity of cathepsins S, B, L, and legumain. We employed a fluorometric assay and measured activity of cathepsins B, L, S, and legumain by cleavage of the substrates Z-Arg-Arg-MCA, Z-Phe-Arg-MCA, Z-Val-Val-Arg-MCA, and Z-Ala-Ala-Asn-MCA, respectively. Activity of cathepsin S and B was not affected by overexpression CST6 whereas cathepsin L and, in particular, legumain showed a reduction in activity in comparison to cell lines infected with the empty vector (FIG. 9). Western blot analysis of the same lysates used for the activity assays confirmed this reduction in activity was not due to a decrease in protein (FIG. 9). Aside from the highly specialized osteoclast, cathepsins are typically located in the lysosome, although a number of authors have reported cancer cells can secrete cathepsins, which may aid in invasion (Mohamed and Sloane, 2006; Small et al., 2011). Thus, we assessed the activity of cathepsins S, B, L, and legumain in serum free conditioned media from our empty vector and cystatin E/M stably expressing cell lines but were unable to detect any marked activity from all proteases tested (data not shown).

CST6 can Prevent Osteoclast Activity on Cultured Bone Slices

To examine CST6 inhibition of cathepsin K activity, we examined whether recombinant CST6 could reduce the bone resorptive ability, mediated by cathepsin K, of primary osteoclasts grown on dentine bone slice. Mesenchymal stem cells were allowed to grow and differentiate into mature osteoclasts on dentine discs prior to treatment with recombinant cystatin E/M or vehicle control. At all concentrations tested (10, 50 and 100 nM), recombinant cystatin E/M significantly reduced the resorption area established by the mature osteoclasts, which indicated that cathepsin K proteolytic activity was being inhibited (FIG. 7B).

CST6 Results in Reduced Tumor Growth and a Lower Incidence of Osteolytic Lesions in SCID-Hu Mouse Model From previous studies, we have noted that not all multiple myeloma cell lines will grow exclusively in the bone in our SCID-Hu mouse model, but we have previously used the H929 cell line for SCID-Hu studies. Therefore, we used the H929 cell line stably transduced with either the empty vector or a vector containing the CST6 ORF for the SCID-Hu studies. Prior to initiating the mouse studies, we demonstrated that overexpression of cystatin E/M did not result in significant growth inhibition in vitro in comparison to the empty vector, pWPI. Remarkably, cystatin E/M resulted in a statistically significant reduction in growth of the H929 cell line in comparison to the empty vector suggesting cystatin E/M was altering the interactions between the myeloma cell and the microenvironment in vivo. Using the same blood samples used for the human immunoglobulin measurement from the final time point, we were able to confirm that the tumor cells were still expressing cystatin E/M by measurement in our ELISA. To determine the effect of cystatin E/M on bone resorption, we performed bone mineral density evaluations on radiographs taken of the mice at the end of the study. There was a substantial, but not statistically significant, reduction in the overall change in bone mineral density when compared to the H929-pWPI cells, which suggests that cystatin E/M is able to inhibit bone resorption in vivo. Finally, the inhibitory role of cystatin E/M on cathepsin K may not be confined to cleavage of type I collagen resulting in bone resorption. Gocheva and colleagues (2010) showed various cathepsins in the tumor microenvironment affected tumor angiogenesis and invasion and this was, in part, due to cleavage of adhesion molecules such as the cadherins. We demonstrate that cathepsin K can cleave E- and N-cadherin using an in vitro assay and that the addition of recombinant Cst6 can inhibit this cleavage. The E-cadherin cleavage products are similar in size to those reported by Gocheva and colleagues (2010) for CTSB, CTSL, and CTSS cleavage of E-cadherin.

Materials and Methods:

Microarray Data Sets

Gene expression profiling data were obtained from previous studies and are available under the NCBI's Gene Expression Omnibus under accession number GSE2658[1,2].

Patients

Gene expression profiling was performed in newly diagnosed patients with multiple myeloma enrolled on total therapy. The institutional review board of the University of Arkansas for Medical Sciences approved these research studies, and all subjects provided written informed consent approving use of their samples for research purposes.

Cell Culture and Reagents

Human myeloma cell lines (ARP1, OCI-MY5, H929 and their derivative cell lines ARP1-CST6, OCI-MY5-CST6, and their relative controls) and murine myeloma cell lines (5TGM1) were cultured in RPMI 1640 medium (Invitrogen, Carlsbad, CA), supplemented with 10% heat-inactivated FBS (Invitrogen), penicillin (100 IU/mL), and streptomycin (100 mg/mL) in a humidified incubator at 37 °C and 5% CO2/95% air. The conditioned media of MM cells was prepared by culturing $0.5\times10^6$ cell/mL with 1% FBS RPMI1640 for 48 hrs and harvesting the media by 1000 g×20 min spin down. The conditioned media was kept in a −80 °C freezer prior to use.

CST6 Overexpression

CST6 cDNA was purchased from Open Biosystems (Huntsville, AL, USA) and cloned into the pWPI lentiviral vector (Dr Didier Trono, School of Life Science, Lausanne, Switzerland). Packaging and concentration of virus was performed using a standard protocol (Zufferey et al., 1997). $0.5\times10^6$ myeloma cells were transduced with lentiviral particles and stably transfected cell lines were identified as GFP expressing cells using FACS Aria.

CST6 Expression and Purification

Human and mouse CST6 cDNA were cloned into pcDNA3.1(+)-C-6His by GenScript. pcDNA3.1(+)-C-6His-CST6 constructs were transfected into HEK293T cells via Lipofectamine2000 (Invitrogen). Conditioned media was collected 48 h and 72 h after transfection. The pH of the media was adjusted to pH7.5-pH8.0 with 0.05M NaOH. Then the sampled was loaded into a HisTrapTMHP column (GE Healthcare) with peristaltic pump at 4 °C. The His-tagged protein was washed with 50 ml 50 mM Na-Phosphate, 300 mM NaCl, 10% glycerol, 5 mM Imidazole pH 7.5, and eluted with 50 mL 0-100% to 50 mM Na-Phosphate, 300 mM NaCl, 10% glycerol, 300 mM Imidazole pH 7.5 on a NGC Chromatography System (Bio-Rad). After concentration by ultrafiltration, 5 ml sample were loaded onto a Superdex 75 100/300 GL column (GE Healthcare) pre-equilibrated with 50 mM Na-Phosphate pH 7.5, 150 mM NaCl, at a flowrate of 0.75 ml/min. The protein purity was determined by silver stain according to the Pierce Silver Stain Kit (Thermo) protocol. The concentration of the purified protein was determined at 280 nm by NanoDrop™ 2000 (Thermo scientific).

Whole Cell Extract and Conditioned Media Preparation for Enzymatic Activities

Preparation of whole cell lysates was performed based on the protocol of Briggs and colleagues (2010). Briefly, cells were seeded at $0.5\times10^6$ per ml in T25 flasks in serum free media and after three days conditioned media and cells were collected. Cells were washed three times in PBS before addition of lysis buffer (100 mM sodium citrate, 1 mM disodium EDTA, 1% n-octyl-ß-D-glucopyranoside, pH 5.8) and three freeze thaw cycles at −80 °C. Cell lysates and conditioned media were cleared by centrifugation at 10,000×g for 5 min before protein quantification was performed using the BCA Protein Assay Kit (Thermo Scientific, Rockford, IL).

In Vitro Kinase Inhibition Assay[3,4]

The ability of CST6 to inhibit the protease activity of papain (sigma #P4762) was measured by absorbance assay using Na-Benzoyl-L-arginine4-nitroanilide hydrochloride (sigma #B3133) as the substrate. 5 μM papain and various concentrations of mouse CST6 were prepared with 400 mM sodium phosphate buffer pH6.5. 25 μl 400 mM sodium phosphate buffer pH6.5, 50 μl papain and 50 μl different concentration (0.1-5 μM) CST6 were mixed and incubated at room temperature for 15 min. 15 μl L-BAPA, which was dissolved in DMSO at a concentration of 50 mM, was added to start the reaction at 37 °C for 1 h. The reaction was stopped by addition of 50p1 of stopping reagent (30% (v/v) acetic acid), and liberated nitroaniline was quantified by A405 measurement in a UV-visible plate reader (Bio-Tek). Papain inhibitory activity (%) was calculated as [Abs (control)−Abs (sample)]/Abs (control)*100.

Cathepsin K Activity Assay

The ability of recombinant CST6 (R&D Systems, Minneapolis, MN) to inhibit cathepsin K protease activity was assessed using the Cathepsin K Drug Discovery Kit (Enzo Life Sciences International, Plymouth Meeting, PA). Fluorimetric assays were done in triplicate in 96-well microtitre plates using cathepsin K, the fluorogenic synthetic substrate Z-Phe-Arg-AMC in the presence of the cathepsin K assay buffer. Inhibitory activity of CST6 towards cathepsin K was measured in serum-free conditioned media from the H929 cell line stably infected with pWPI or CST6 lentivirus. Conditioned media equating to 25 μg was added to each well and inhibitory activity was evaluated by measuring the residual enzyme activity. Recombinant CST6 was added to assays at various concentrations and the resultant fluorescence was measured using a SpectraMax M2 microplate reader (Molecular Devices, Sunnyvale, CA) with excitation at 380 nm and emission at 460 nm wavelengths. The initial rates from the CatK progress curves in the presence of predetermined concentrations of recombinant CST6 were subjected to non-linear regression analysis (Morrison and Walsh, 1988) using GraFit® software (Erithacus Software Limited, Surrey, UK) to determine the inhibition constant (Ki).

Measurement of Intracellular Cathepsin B, L, S and Legumain Activity

Fluorimetric assays to measure intracellular cathepsin B, L, S, and legumain activity were performed as described by Briggs and colleagues (2010). Cathepsins B, L, S, and legumain activity were measured by cleavage of the substrates Z-Arg-Arg-MCA, Z-Phe-Arg-MCA, Z-Val-Val-Arg-MCA, and Z-Ala-Ala-Asn-MCA, respectively (Peptides International, Louisville, KY). Cell lysate (50 μg) was added to black 96-well microfluor plates (No. 7005; Thermo Fisher Scientific). After the addition of 100 μl buffer and 50 μl substrate solution (final concentration 10 μM) the resultant fluorescence was measured every 60 s over a period of 60 min with excitation at 380 nm and emission at 460 nm wavelengths. Temperature was kept at 37 °C and all measurements were performed in triplicate. Cathepsin L activity was measured in the presence of the cathepsin B-specific inhibitor CA074 (0.25 μM; Sigma).

Western Blot

Cells were treated with CST6 at various concentrations and durations. The cell lysates were lysed in 150 mM NaCl, 10 mM EDTA, 10 mM Tris pH 7.4, and 1% Triton X-100 supplemented with Protease inhibitor (#Roche). Protein-lysates were incubated on ice for 30 min and centrifuge at 13500 rpm for 4 °C for 10 min. For cell fractionations, a Nuclear/Cytosol Fractionation kit (BioVision, Inc.) was used according to the manufacturer's protocol. The protein concentration in the supernatants was determined by NanoDrop™ (Thermo Fisher Scientific). Proteins were separated with NuPAGE 4% to 12% Bis-Tris Gel (NOVEX) at 200 V, then transferred to a nitrocellulose membrane for 1 hour at 400 mA at 4 °C. The membrane was blocked for 60 minutes with 5% milk at room temperature. Antibodies against CST6 (R&D Systems), CTSK (Santa Cruz Biotechnology), p52 (Cell Signal Technology), p50 (Cell Signal Technology), GAPDH (Cell Signal Technology), Histone3 (Cell Signal Technology) were incubated overnight at a dilution of 1:1,000. Secondary rabbit antibody (ANASPEC, goat anti-rabbit IgG [H+L], HRP-conjugated) and secondary mouse antibody (Santa Cruz Biotechnology, goat anti mouse IgG-HRP, sc-2005) were incubated for 1 hour at a concentration of 1:10,000. For exposure, Immobilon Western HRP Substrate Peroxide Solution from Millipore was used. Imaging was done with a Bio-Rad ChemiDoc XRS+ with Image Lab Software.

Real-Time PCR

For quantitative analysis of gene expression, total RNA was isolated by RNeasy kit (Qiagen). Complementary DNA was synthesized using an Iscript reverse transcription kit according to the manufacturer's instructions (Bio-Rad). Real-time qPCR for mouse CTSK, TRAP, NFATc1, and β-actin were performed with SYBR Green Super Mixture Reagents (Bio-Rad) on the CFX Connect real-time system (Bio-Rad). PCR was initiated at 95 °C for 3 minutes to hot-start the DNA polymerase and denature the template, and then 40 cycles consisting of denaturing at 95 °C for 30 seconds, annealing, and extension at 60 °C for 30 seconds were performed. The relative quantitation of each gene is calculated as ΔΔCT. Each sample is normalized to the endogenous control gene β-actin. Primers were as follows:

```
Mouse CTSK:
forward,
                              (SEQ ID NO: 5)
5'-AGCAGGCTGGAGGACTAAGGT;

reverse,
                              (SEQ ID NO: 6)
5'-GATTTGTGCATCTCAGTGGAAGAC;
```

-continued

```
NFATc1:
forward,
                                    (SEQ ID NO: 7)
5'-CCTTATGTGGCTCAGGTCTTACTTC;

reverse,
                                    (SEQ ID NO: 8)
5' TGGTCCCCGAGACCACAAT;

TRAP:
forward,
                                    (SEQ ID NO: 9)
5' AAGTATGCCCACACCAACTGATC;

reverse,
                                   (SEQ ID NO: 10)
5'-GAAAGCCCGTTCCCAAGAAA;

β-actin:
forward,
                                   (SEQ ID NO: 11)
5'-GCCACTGCCGCATCCTCTTC;

reverse,
                                   (SEQ ID NO: 12)
5'-AGCCTCAGGGCATCGGAACC;
```

CST6 and DKK1 Sandwich ELISA

The DKK1 sandwich ELISA was performed as previously described (Tian et al., 2003). For the CST6 sandwich ELISA, maxisorp plates (COMPANY) were coated with 50 μl of a monoclonal CST6 antibody (R&D Systems, Minneapolis, MN) at a concentration of 2 μg/ml in phosphate buffered saline (PBS), pH 7.2, and incubated overnight at 4 °C. The plates were washed (PBS containing 0.1% Tween 20, pH 7.2) and blocked with 4% bovine serum albumin (100 μl/well) in PBS containing 0.02% $NaN_3$ at room temperature for 1 h. Plates were washed prior to addition of recombinant CST6 protein (R&D Systems, Minneapolis, MN) for establishment of a standard curve (0.5-10 ng/ml in ELISA dilution buffer), MMCL conditioned media and patient serum samples to each well of the plates and incubated at 4 °C. overnight. Plates were washed before incubation with biotinylated polyclonal CST6 antibody (50 μl/well, 0.2 μg/mil in PBS pH 7.2) (R&D Systems, Minneapolis, MN) at 37 °C for 2 h. Plates were then washed prior to incubating each well with 50 μl of a 1:10,000 dilution of streptavidin-horseradish peroxidase at room temperature for 1 h. Color development was achieved with the OPD substrate according to manufacturer instructions and the reaction was stopped by treatment of the plates with sulfuric acid (50 μl/well, 0.5 mol/l). The absorbance values were measured at 490 nm. Validation of the specificity of the CST6 sandwich ELISA was tested by ensuring no color development was evident when recombinant cystatin A, B, C, D, F, S, SN, and kininogen proteins were used.

Osteoclast Formation and Osteoclast Resorption Assays

RAW264.7 cells were obtained from the American Type Culture Collection (ATCC, Manassas, VA, USA) and grown in Dulbecco's modified Eagle's medium (DMEM, Life Technologies) containing 10% FBS and 1% penicillin/streptomycin (i.e., DMEM complete medium). $5\times10^4$ cells were seeded into 12-well plate with indicated concentrations of M-CST6 in the presence of 10 ng/ml RANKL (R&D Systems). After 3-5 days, the adherent cells were fixed and stained with TRAP (Sigma-Aldrich) according to manufacturer's instruction. Osteoclasts were identified as TRAP+ cells containing 3 or more nuclei. Primary mouse bone marrow macrophage (BMM) were collected from 6-8 week-old C57BL/6 mice. $4\times10^4$ cells were seeded into 96-well plate with a-MEM containing 10% FBS and 10 ng/ml M-CSF (PeproTech) for 2 days to recruit macrophages. Then osteoclast differentiation was induced with 10 ng/ml RANKL (R&D Systems) for 3-5 days. TRAP staining was used to count the mature osteoclast cells[5].

Preparation of Osteoclasts and Osteoclast Resorption Assays

Preparation of osteoclasts and osteoclast resorption assays were performed as described by Pennisi and colleagues (2009). Bone resorbing osteoclasts were prepared from peripheral blood mononuclear cells (PBMCs) from patients with MM. Dentine discs (Immunodiagnostic Systems, Scottsdale, AZ) were placed in each well of a 96 well plate and allowed to equilibrate in 100 μl of osteoclast culture media for 1 h. Equilibration media was aspirated off and PBMCs ($2.5\times10^6$ cells/ml) in osteoclast medium containing a minimum essential medium supplemented with 10% fetal bovine serum (FBS), 50 ng/ml receptor activator of NF-κB ligand (RANKL), 25 ng/ml macrophage colony stimulating factor (M-CSF) and antibiotics were cultured on dentine discs. At approximately 10 days, wells containing no dentine discs were examined by light microscope to verify differentiation of PBMC into large multinucleate osteoclasts capable of bone resorption activity. To test the effect of CST6 on mature osteoclasts bone resorbing ability, osteoclasts were treated with a range of pre-determined concentrations of recombinant CST6 for 14 days. Dentine slices were treated with 10% bleach solution for 5 min and washed in distilled water. Resorption pits were photographed with a Nikon eclipse 450 microscope. The ratio of resorption area:total area was quantified by using OsteoMeasure XP (Osteometrics, GA, USA).

Ex Vivo Organ Culture Assay[6]

Calvariae from 10 day old neonatal C57BL/6 mice were dissected as previously described[7]. Half calvarial pieces were co-cultured with $2\times10^5$ ARP-1 cells in α-MEM/RPMI1640 50/50 medium supplemented with 1% P/S for 10 days in six-well plate and the medium was changed every 3 days. Samples were fixed in 10% formalin for 24 h, decalcified for 48 h in 10% EDTA pH7.2, embedded in paraffin, sectioned, and stained with H&E. Whole length of the slides were captured by the Olympus BX-61 microscope. Bone lesions on the surface were measured using ImageJ software.

Cell Viability

Cell culture (10 μl) was mixed with 10 μl of trypan blue and samples were counted in a hemocytometer. Translucent cells were counted as viable and blue-stained cells were counted as dead. Cell viability was calculated by dividing viable cells by total cell number. Each sample was done in triplicate.

Mouse Models

All mouse experiments were performed under protocols approved by the Institutional Animal Use and Care Committee of the University of Iowa. Human myeloma cells ($0.5\times10^6$ cells in 100 μL PBS) were injected subcutaneously into the flank of NOD-Rag/null gamma mice. For 4 weeks, the mouse tumors were harvested to determine volume and weight. In KaLwRij mouse model, 5TGM1-GFP ($1\times10^6$ cells in 100 L PBS) were injected through tail vein. Mice were treated with one of the following: (a) PBS, (b) 25 μg/kg CST6, (c) 50 μg/kg CST6, (d) untreated control. Mice were bled every week to harvest serum for detecting IgG2b by the ELISA assay according to the manufacturer's instructions (Bethyl Laboratories). For survival studies, mice were monitored until they reached the human end point.

SCID-Hu Model

SCID-hu mice were prepared as previously described (Yaccoby et al, 1998; Yaccoby & Epstein, 1999) to test the effect of CST6 on growth of myeloma cells and myeloma-induced bone disease. One hundred thousand H929 cells infected with either pWPI or CST6 lentivirus were diluted in 100 μl phosphate-buffered saline (PBS) and injected directly into the implanted human bone. Mice were bled weekly from the tail vein, and changes in levels of circulating human light chain immunoglobulin (hIg) of the M-protein isotype were used as an indicator of tumor growth.

Determination of Human hIg Levels

Levels of human κ light chains were determined by enzyme-linked immunosorbent assay (ELISA) as previously described (Yaccoby et al, 1998; Yaccoby & Epstein, 1999). At the end of each experiment, all samples were analyzed in the same assay to preclude interassay variability.

Radiographic and Bone Mineral Density Evaluations

Radiographs were taken with an AXR Minishot-100 beryllium source instrument (Associated X-Ray Imaging Corp., Haverhill, MA, USA) using a 10-second exposure at 40 kV. Changes in bone mineral density (BMD) of the implanted bones were determined using PIXImus DEXA (GE Medical Systems LUNAR, Madison, WI, USA) (Yaccoby et al, 2006, 2007).

Statistical Analyses

Results are presented as average ±SD or as average±SEM, as indicated in the Brief Description of the Drawings. Statistical analysis was done using GraphPad Prism 6.05 and Prism 7.0. All other comparisons were analyzed by unpaired, 2-sided, independent student's t test, unless otherwise described in the Brief Description of the Drawings. P<0.05 was considered significant. Statistical difference of Kaplan-Meier survival curves was determined by long-rank test.

REFERENCES

1. Zhan F, Huang Y, Colla S, et al. The molecular classification of multiple myeloma. *Blood.* 2006; 108 (6):2020-2028.
2. Shaughnessy J D, Jr., Zhan F, Burington B E, et al. A validated gene expression model of high-risk multiple myeloma is defined by deregulated expression of genes mapping to chromosome 1. *Blood.* 2007; 109(6):2276-2284.
3. Zhou Y, Zhou Y, Li J, et al. Efficient expression, purification and characterization of native human cystatin C in *Escherichia coli* periplasm. *Protein Expr Purif* 2015; 111:18-22.
4. Vincents B, Vindebro R, Abrahamson M, von Pawel-Rammingen U. The Human Protease Inhibitor Cystatin C Is an Activating Cofactor for the Streptococcal Cysteine Protease IdeS. *Chemistry & Biology.* 2008; 15(9):960-968.
5. Xiu Y, Xu H, Zhao C, et al. Chloroquine reduces osteoclastogenesis in murine osteoporosis by preventing TRAF3 degradation. *J Clin Invest.* 2014; 124(1): 297-310.
6. Xu L, Mohammad K S, Wu H, et al. Cell Adhesion Molecule CD166 Drives Malignant Progression and Osteolytic Disease in Multiple Myeloma. *Cancer Res.* 2016; 76(23):6901-6910.
7. Mohammad K S, Chirgwin J M, Guise T A. Assessing new bone formation in neonatal calvarial organ cultures. *Methods Mol Biol.* 2008; 455:37-50.
8. Tian E, Zhan F, Walker R, et al. The role of the Wnt-signaling antagonist DKK1 in the development of osteolytic lesions in multiple myeloma. *N Engl J Med.* 2003; 349(26):2483-2494.

Example 2

Osteolytic bone disease is a hallmark of multiple myeloma (MM), a malignancy of antibody-secreting plasma cells (PC). While osteolytic bone metastases is a feature of several cancers, it is a presenting and a diagnostic criteria for MM. However, a significant fraction of MM cases fail to present with or develop osteolytic lesions. In MM, osteolysis is linked to both suppressed osteoblastogenesis and increased osteoclastogenesis 1. New bone formation is suppressed, at least in part, via DKK1-mediated inhibition of Wnt/β-catenin signaling, which is essential for osteoblast differentiation[2]. DKK1 also increases osteoclast numbers by increasing the RANKL/OPG ratio in the MM bone marrow microenvironment 3-5.

Using global gene expression profiling (GEP) the inventors have created a molecular classification of MM[6-8]. Correlation of clinical parameters with disease subtypes revealed a statistically significant lower incidence of bone disease in what they have termed the low bone (LB) disease subtype[6]. The existence of the LB molecular subtype was independently verified[6-8]. These data suggested that MM lacking bone disease represent a distinct pathologic entity. The molecular basis for the absence of bone disease in MM is not understood. Positron emission tomography-computed tomography (PET-CT) is recommended by the International Myeloma Working Group (IMWG) to ascertain the presence of MM lytic bone lesions 9.

In the following Example, the inventors combined PET-CT and global gene expression profiling (GEP) of purified tumor cells from newly diagnosed MM (NDMM) patients to identify secreted molecules that might suppress osteolytic bone disease in MM. They studied cells from 526 MM patients, including 185 patients with no focal MM bone lesions by positron emission tomography/computed tomography (PET-CT) and 341 patients with focal tumor growth in the bone. The expression of 55 genes (of approximately 21,000 total genes) distinguished the two groups of disease growth patterns (P<0.00001). The most significant of these genes, CST6 and its corresponding protein (cystatin M/E), was studied in detail, as cystatin M/E is a secreted factor that has been linked to osteoclast function. Enzyme-linked immunosorbent assay (ELISA) revealed that cystatin M/E levels in bone marrow serum are correlated with the mRNA patterns of CST6. Recombinant cystatin M/E or bone marrow serum containing elevated levels of cystatin M/E significantly inhibited the activity of the osteoclast-specific protease cathepsin K, and blocked osteoclast differentiation and function. Recombinant cystatin M/E inhibited bone destruction in an in vivo model of MM. This work suggests that the secretion of CST6, an inhibitor of osteoclast differentiation and function, by MM cells prevents osteolytic bone lesions in patients with MM.

Figure 11:
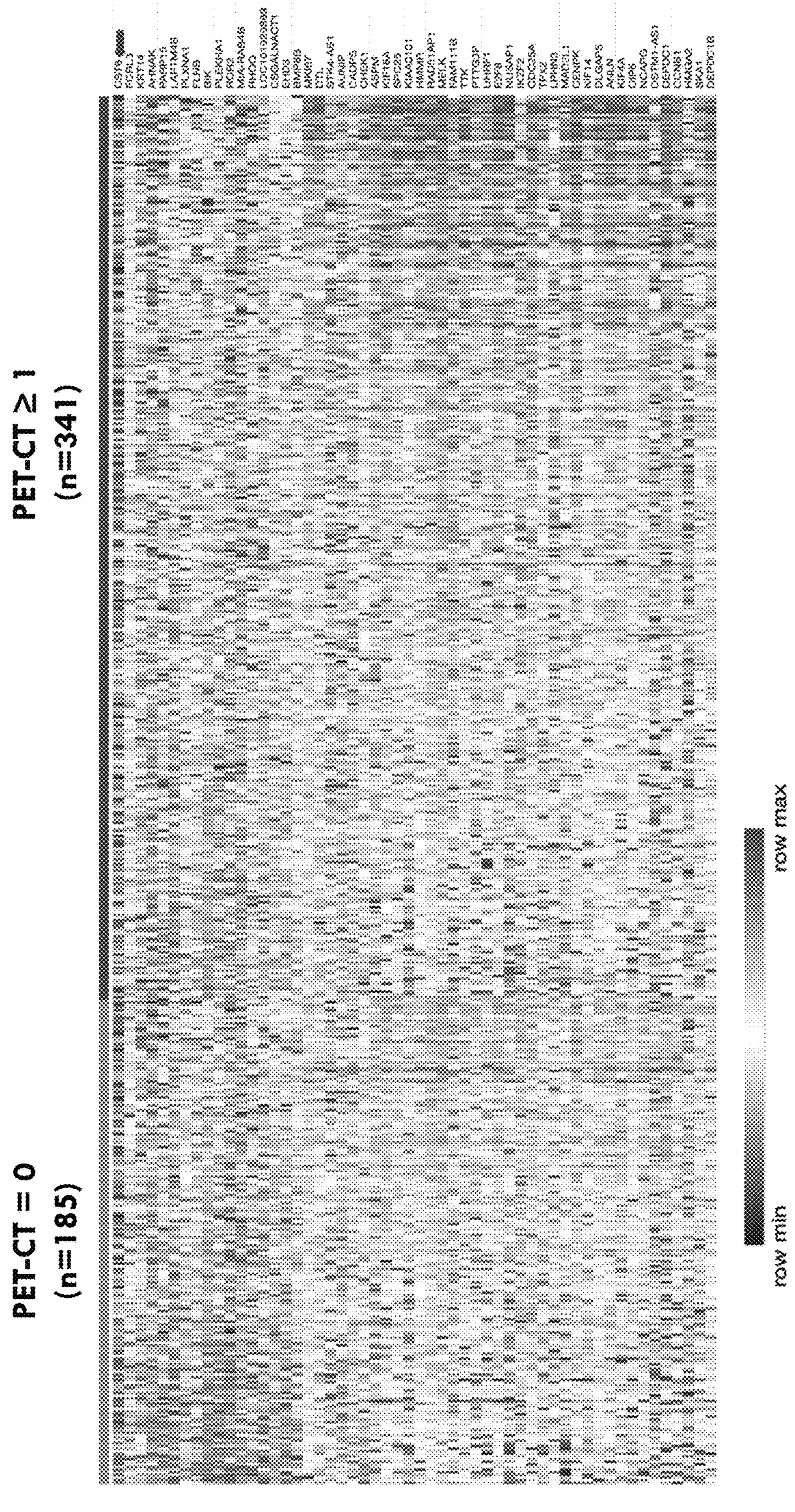
FIG. 11 shows that high expression of CST6 is linked to the absence of bone lesions in MM. (A) Clustergram heatmap of 55 genes significantly differentially expressed in MM cells from patients with no focal lesions (n=185) on PET-CT and patients with one or more focal lesions (n=341) on PET-CT (P<0.00001). The 17 genes with elevated levels of expression in MM cells from patients with no lesions on PET-CT and ranked from top to bottom by significance (the red arrow indicates the gene CST6), while the 38 genes with significantly upregulated expression in patients with one or more lesions on PET-CT are ranked from bottom to top by significance. The gene symbols are listed on the right. (B) Affymetrix MAS5.0 normalized mRNA expression signal is indicated on the y axis. The expression level of CST6 in each sample is indicated by the height of the bar. Samples are ordered from the lowest to highest level of expression of CST6 from left to right on the x axis. (C) Bar graph showing the proportion of patients with no PET-CT lesions or with 1 or more PET-CT lesions for each MM subtype. (D) Bar graph showing DKK1 (red) and CST6 (blue) expression. The expression of CST6 and DKK1 in each sample is indicated by the height of the bar. A negative correlation was found between CST6 and DKK1 signal with a threshold of 5000. (E) Dot plot showing the correlation between CST6 mRNA and protein expression. The level of expression of CST6 mRNA was quantified by microarray analysis and CST6 protein was measured by enzyme-linked immunosorbent assay (ELISA) in 75 NDMM patients. Each spot indicates the relative relation of CST6 mRNA and protein expression levels. There was a significant correlation between the level of CST6 mRNA in MM cells and the level of CST6 protein in MM bone marrow serum (r=0.60, P<0.0001).
Figure 11:
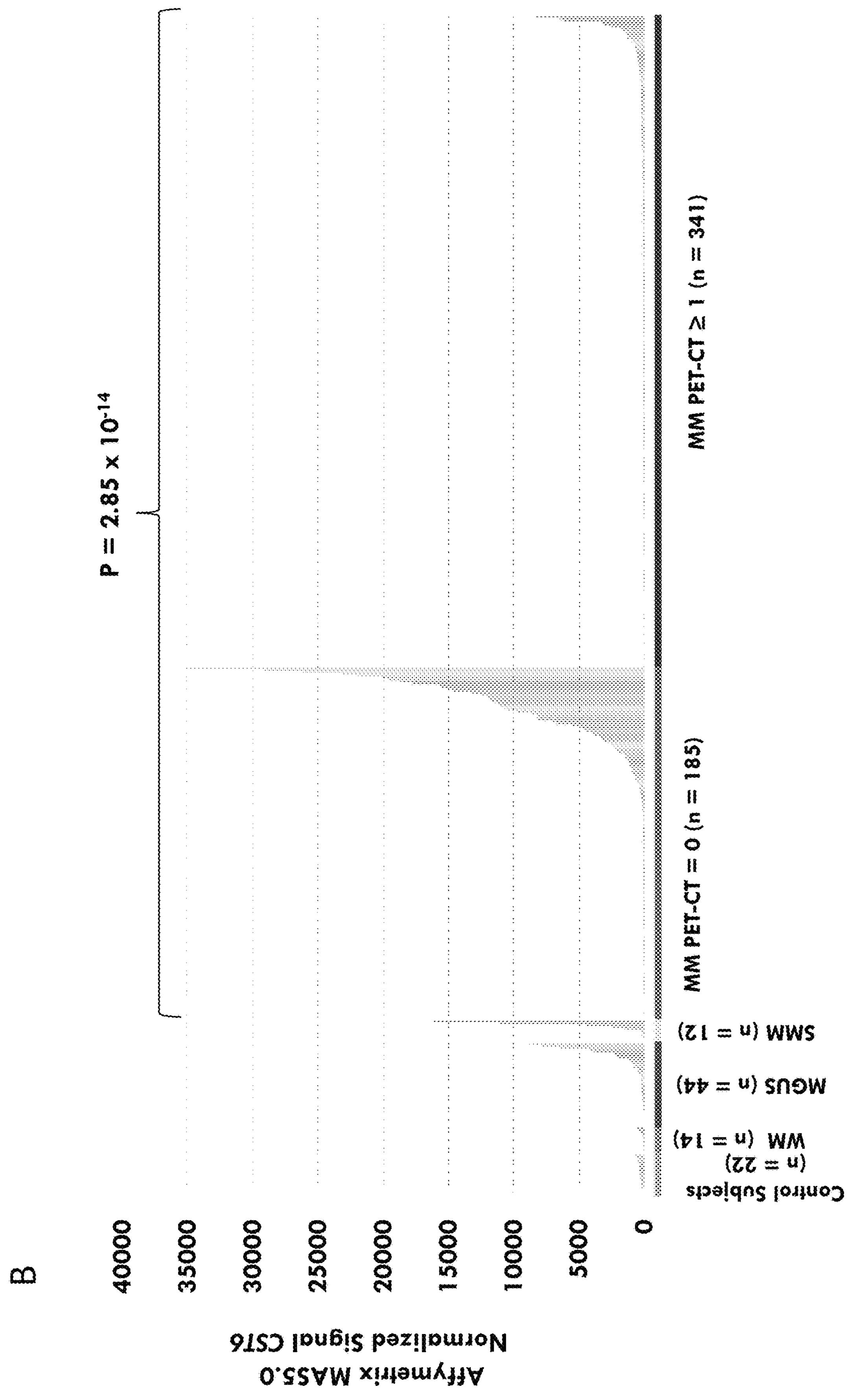
Figure 11:
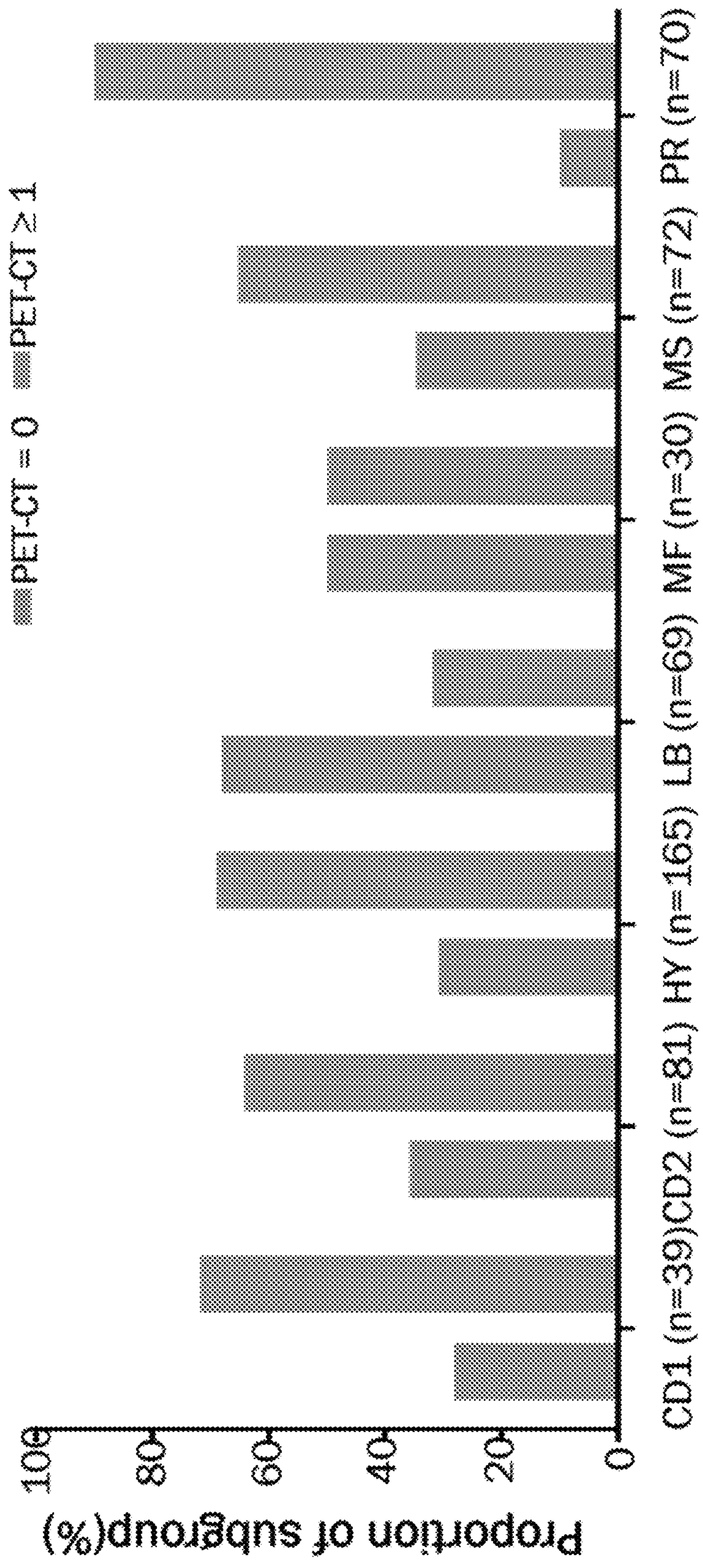
Figure 11:
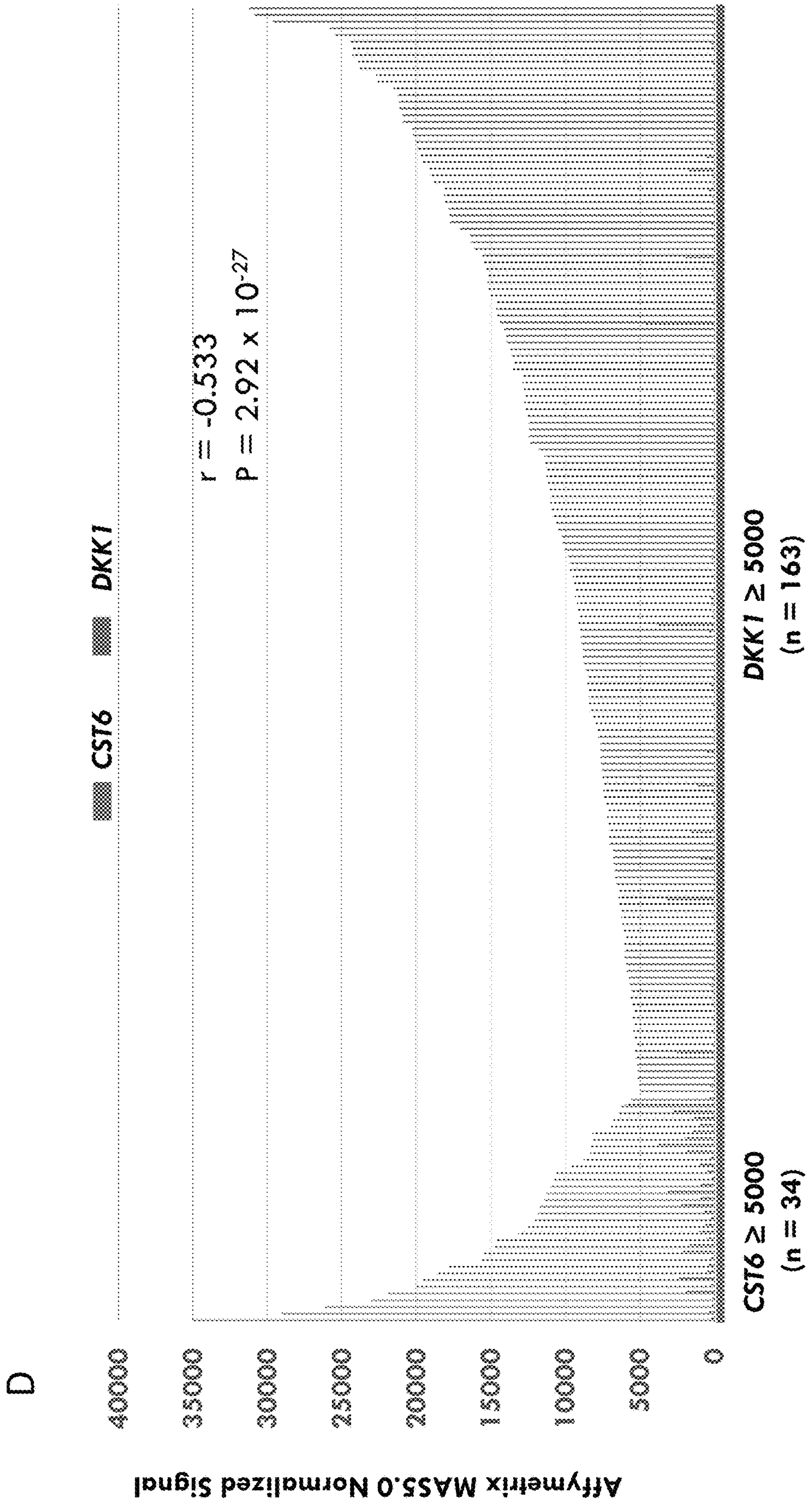
Figure 11:
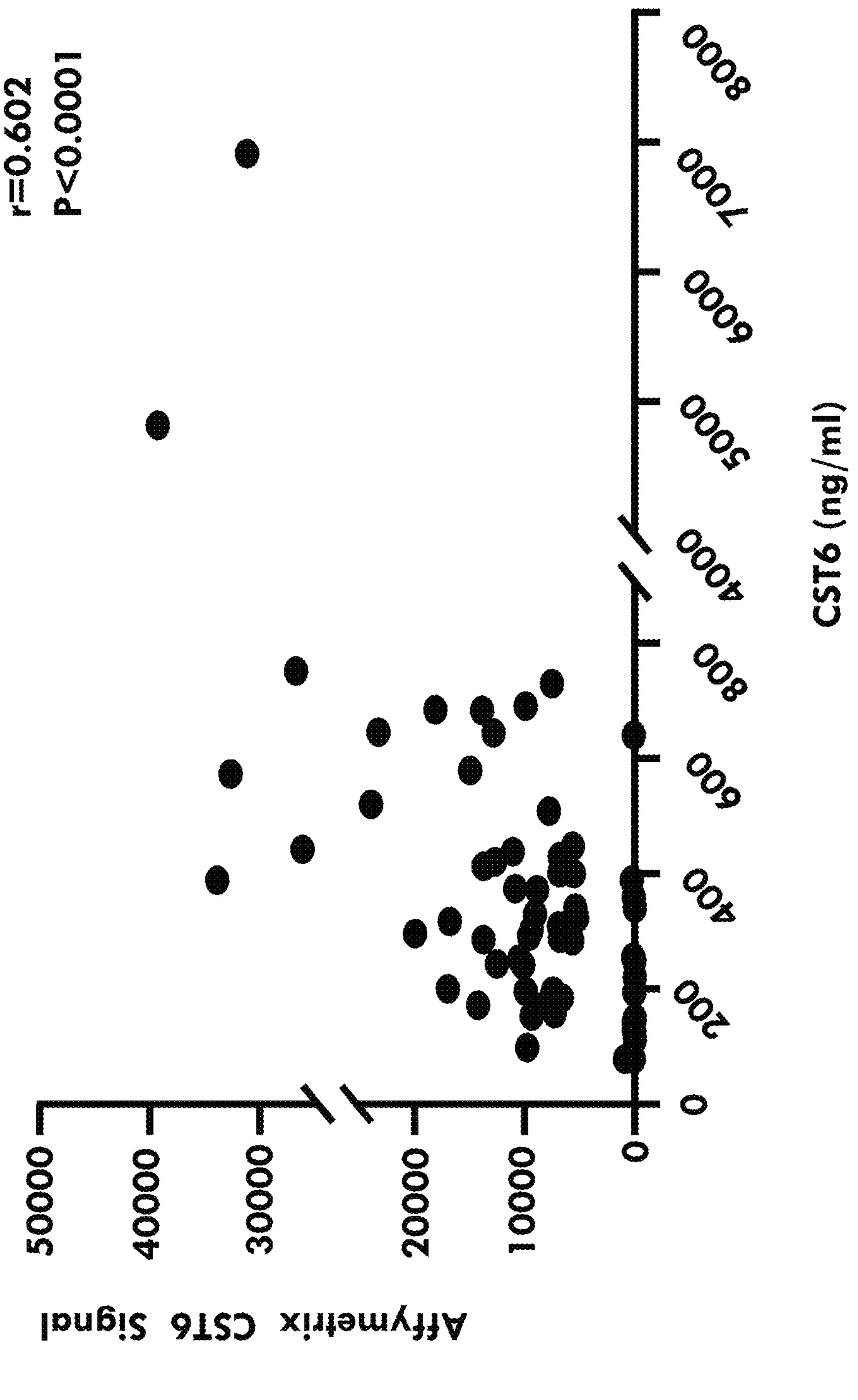

Results:

The Absence of MM Bone Disease is Linked to Elevated Expression of CST6 We correlated global mRNA expression levels in CD138-selected bone marrow (BM) PC from 526 newly diagnosed MM with the presence or absence of PET-CT defined focal lesions. Of these, 185 had no evidence of PET-CT lesions while 341 cases had greater than or equal to one focal lesion detected by PET-CT. We identified 55 genes that were significantly differentially expressed (greater than 1.4-fold and P<0.00001) between these two groups. Supervised cluster analysis showed these 55 genes were distinctly differentially expressed in MM patients with or without bone lytic lesions (FIG. 11A). CST6 was the most significantly differentially expressed gene ($P=2.85\times10^{-14}$) in the analysis and was elevated in the group with no PET-CT lesions (FIG. 11B). CST6 encodes the protein cystatin M/E, a soluble inhibitor of cysteine proteases. Genes associated with cell proliferation were significantly elevated in cases with ≥1 PET-CT lesion (FIG. 11A). CST6 is barely detectable in PC isolated from healthy subjects and patients with Waldenstrom's macroglobulinemia (WM) (FIG. 111B). The gene is expressed in a subset of monoclonal gammopathy of undetermined (MGUS) and smoldering MM (SMM) but at much lower levels than see in MM without bone lesions (FIG. 111B). We found that 68% of the LB subtype had no PET-CT lesions while 90% of the proliferation (PR) subtype had one or more PET-CT lesions (FIG. 11C).

Previously, we showed an inverse relationship between DKK1 and CST6 and the presence of MRI-defined bone lesions in MM[2]. We divided the 526 cases into those in which MM tumor cells expressed CST6 and DKK1 above Affymetrix Signal 5000. CST6 was above 5000 in 34 cases and DKK1 above 5000 in 163 cases (FIG. 11D). Only one of the 163 cases had both high DKK1 had high CST6 expression, and none of the 34 cases with high CST6 had high DKK1 (FIG. 11D). Taken together with previous results, these data indicate that elevated DKK1 and CST6 define two separate subtypes of MM, one with and one without bone disease.

An ELISA for CST6/cystatin M/E was developed and standard curves were created using recombinant protein. CST6 was detected in serum isolated from the BM aspirates from which the PC were isolated and protein and mRNA levels were correlated (FIG. 11E). The mean (±SD) level of CST6 protein in the bone marrow serum from 75 patients with NDMM for whom gene-expression data were also available was 673.0±1076.1 ng per milliliter. In contrast, the CST6 level was 13.2±19.4 ng per milliliter from 10 control subjects. These data indicate that CST6 protein and mRNA levels are correlated and that CST6 protein is significantly elevated in MM bone marrow.

Recombinant CST6 Protein and Human MM Bone Marrow Serum with High CST6 Protein Inhibits Osteoclast Differentiation and Function We next investigated whether CST6 can block osteoclast differentiation, as is suggested by previous studies[10,11] Mouse and human bone marrow monocytes (BMMs) were induced to differentiate into osteoclasts by addition of RANKL and M-CSF with or without various doses of CST6. TRAP staining showed that CST6 significantly suppressed formation of TRAP-positive multinuclear osteoclasts in a dose-dependent manner (FIG. 12A-B, FIG. 15A-B). This effect was partially neutralized by an anti-CST6 antibody, but not by a non-specific IgG (FIG. 12A-B, FIG. 15C-D). Furthermore, recombinant mouse CST6 (rmCST6) also significantly reduced OC resorption area using the Corning® Osteo Assay, and this reduction was partially reversed by an anti-CST6 antibody (FIG. 12A-B, FIG. 15C-D). We found that 200 ng/ml rmCST6 protein was sufficient to inhibit osteoclast formation and function.

Figure 12:
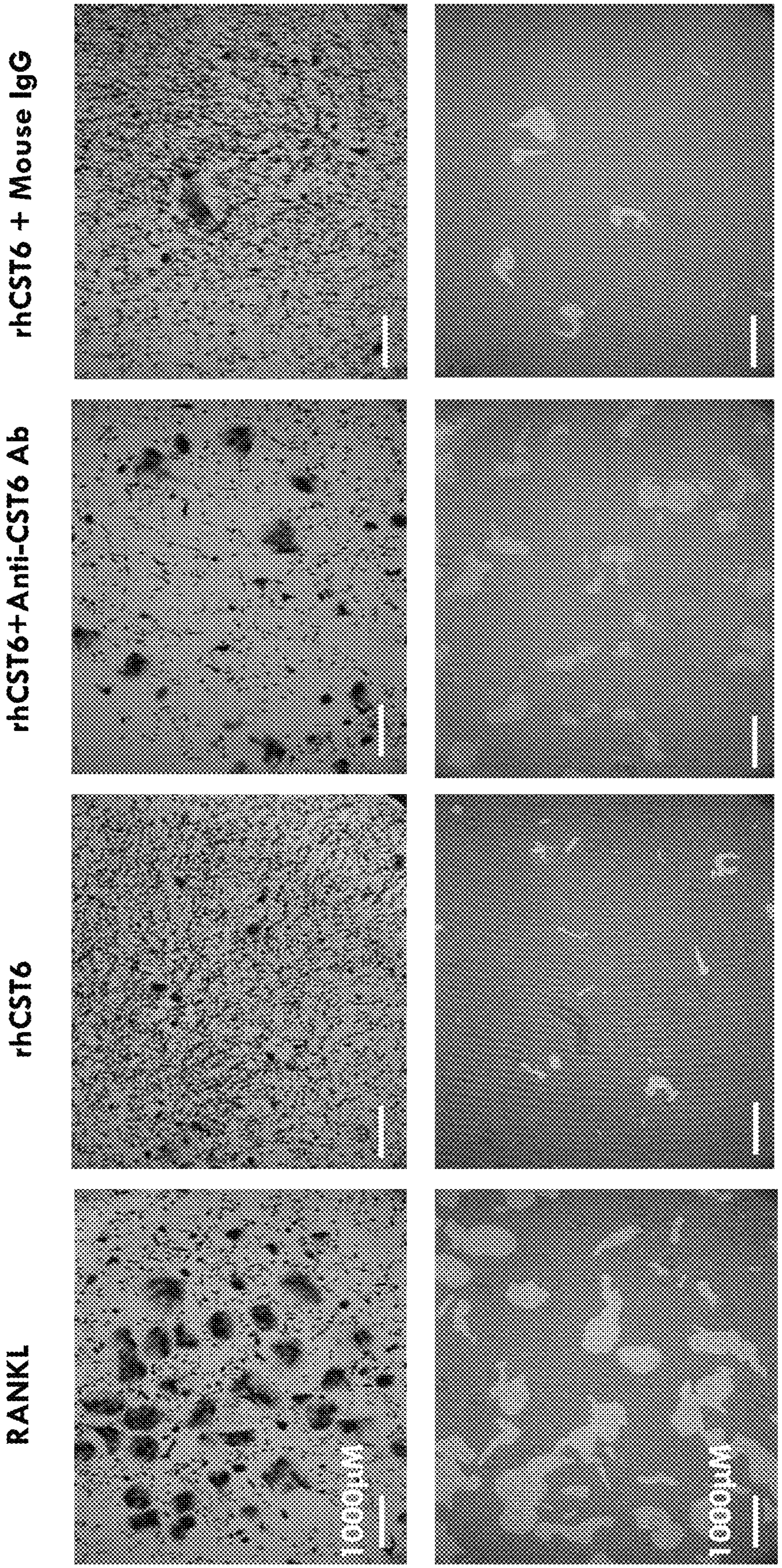
FIG. 12 shows that CST6 inhibits osteoclast differentiation and function. (A) Human osteoclast (OCL) precursor cells were differentiated into OCL with M-CSF and RANKL for 7 days. 200 ng/ml rhCST6, 4 μg/ml anti-CST6 antibody or non-specific mouse IgG were present throughout the process as indicated. On day 7, half of the wells in each group were stained with TRAP solution and the remaining half of the wells were bleached for quantifying resorption areas. Scale Bar=1000 μm. (B) Bar graphs showing the quantification of TRAP$^+$ OCL and the bone resorption area. (C) Bone marrow serum from healthy donors and MM patients was added into the cell culture media with indicated CST6 concentrations. Culture media containing high CST6 protein (final concentration 200 ng/ml) from Patient 5 (P5) showed significant inhibition of OCL differentiation and bone resorption, while culture media containing low CST6 protein from a healthy donor and Patient 1 (P1) with low levels of CST6 did not show inhibition of OCL differentiation and function. 4 μg/ml of anti-CST6 antibody or non-specific mouse IgG were also added to the culture media during human OCL differentiation. On day 7, half of the wells in each group were stained with TRAP solution and the remaining wells were bleached to quantify resorption areas. The CST6 level in each bone marrow serum sample was determined by ELISA as described in FIG. 11. Scale Bar=1000 μm. (D) Bar graphs showing the results of TRAP$^+$ OCL and the bone resorption area quantification. P values are for the comparison between the RANKL and RANKL plus serum containing 200 ng/ml CST6. (E) Cathepsin K activity was measured using the cathepsin K drug discovery kit. The y axis represents the cathepsin K activity expressed as relative fluorescence intensity (RFU). The x axis is the time points treated by CST6 protein in multiple doses. (F) Western blot showing the cathepsin K (CTSK) expression level during the period of mouse OCL differentiation treated with or without 200 ng/ml recombinant mouse CST6 (rmCST6). *P<0.05, P<0.01, *P<0.001, ****P<0.0001; ns, not significant. Statistical analysis was performed using unpaired, 2-sided, independent student's t test.
Figure 12:
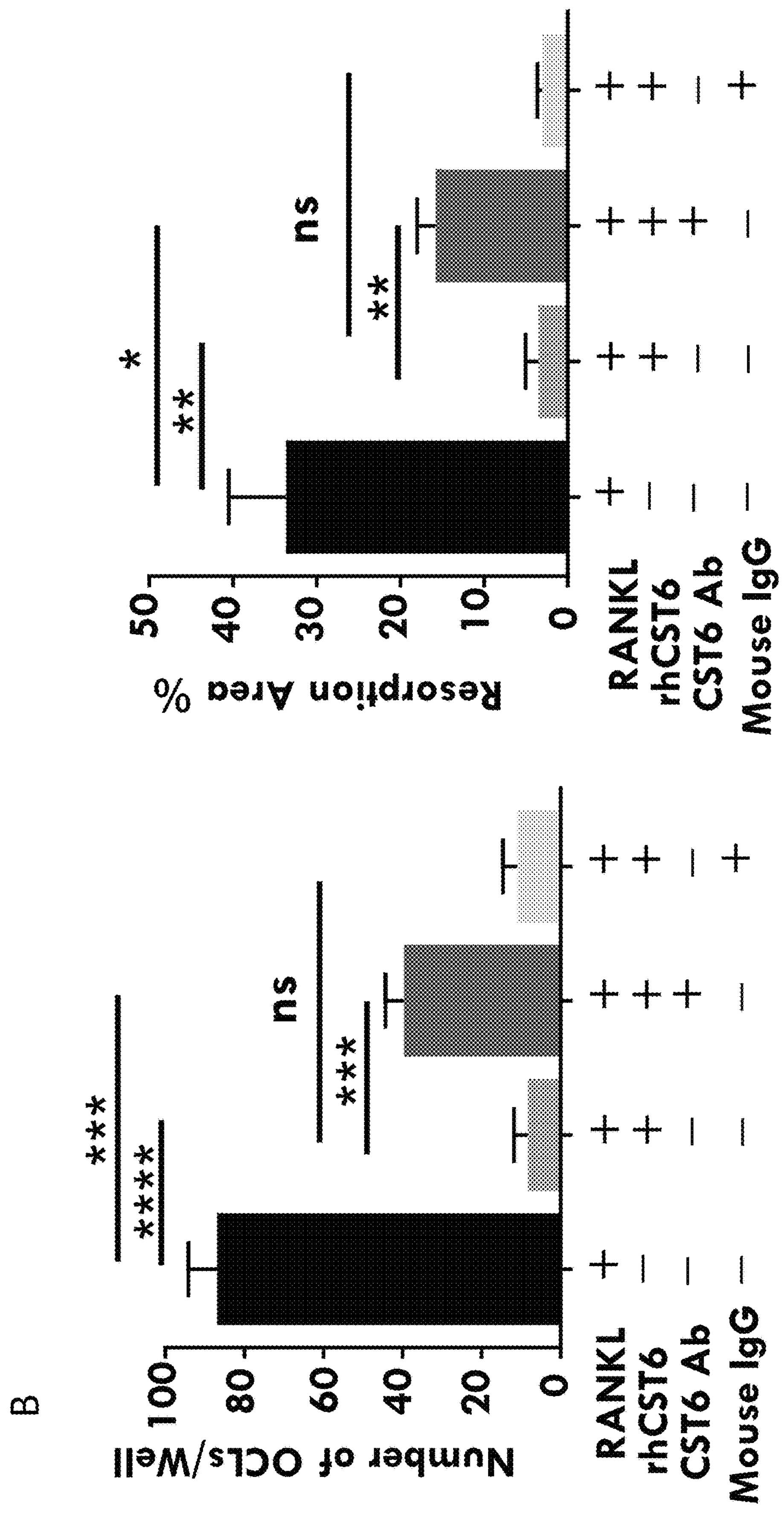
Figure 12:
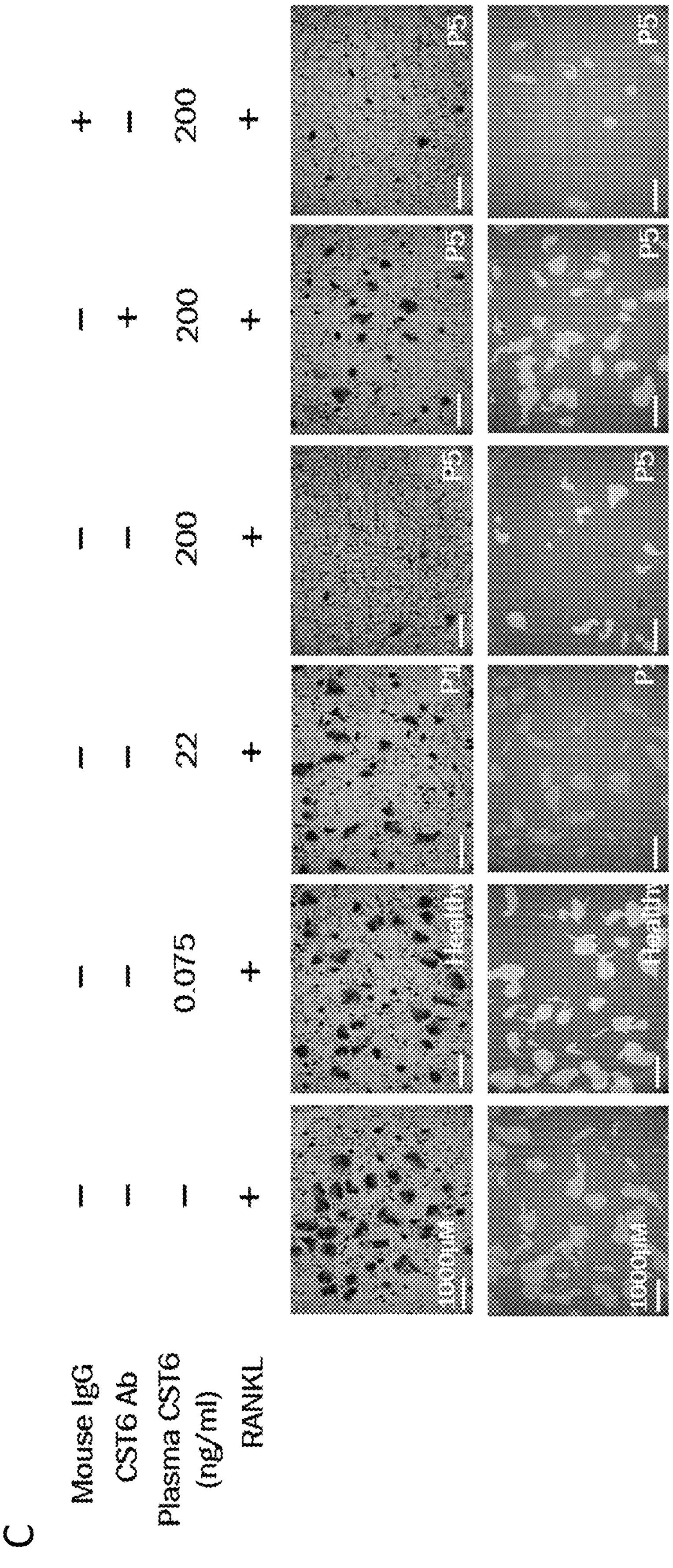
Figure 12:
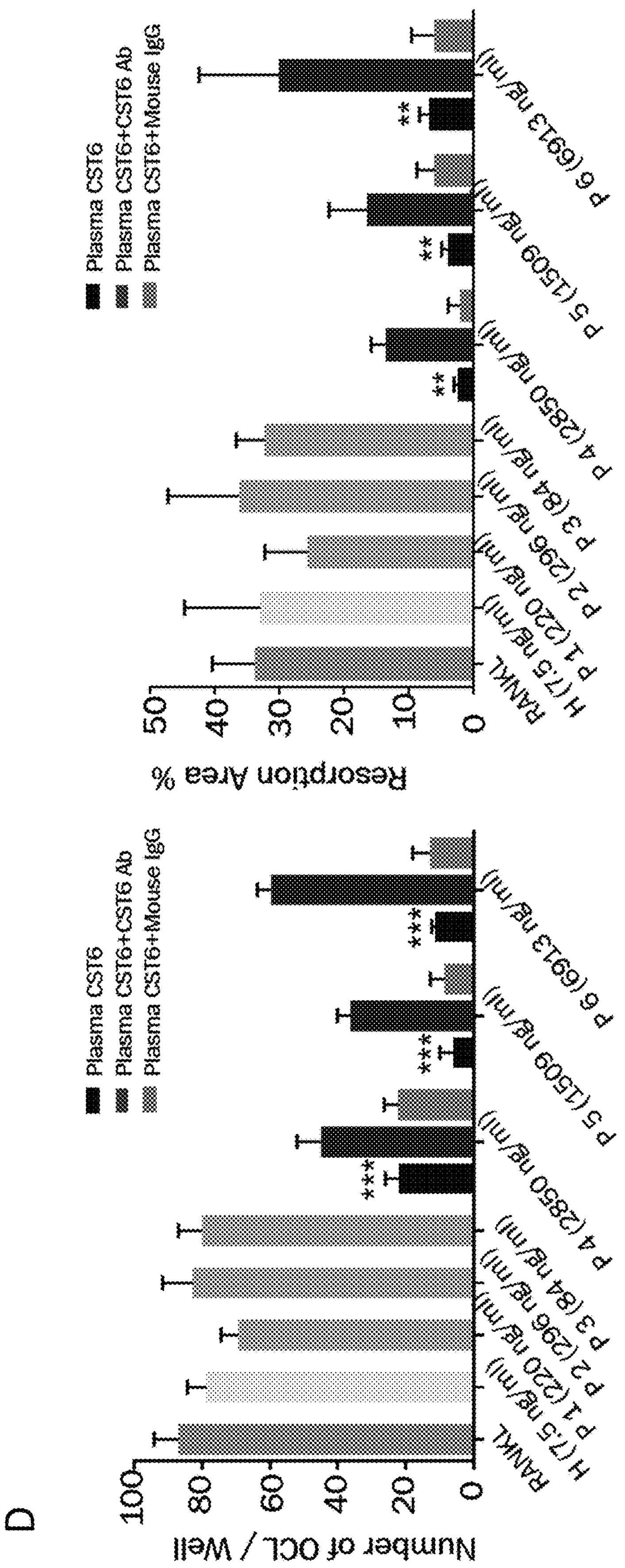
Figure 12:
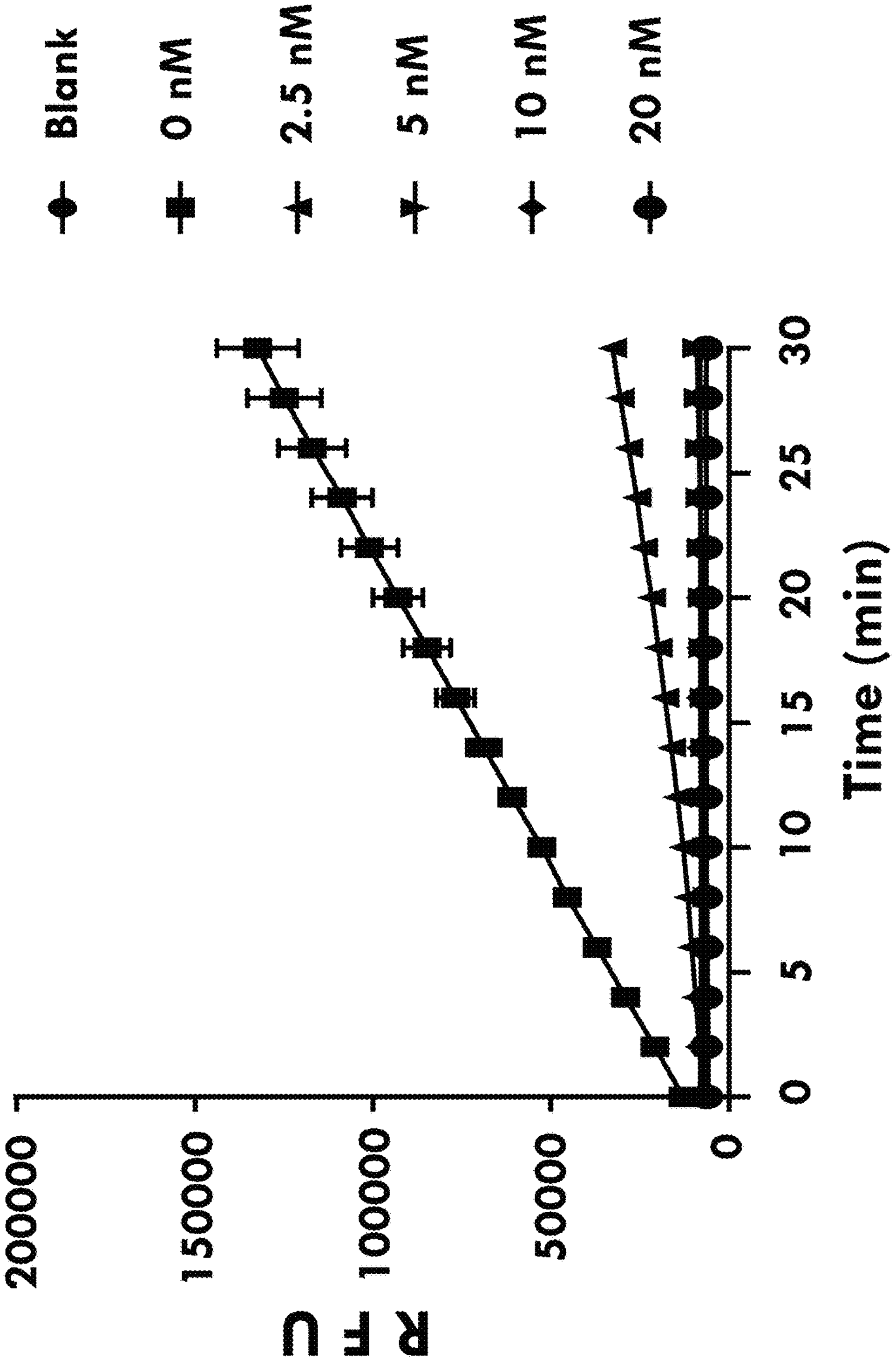
Figure 12:
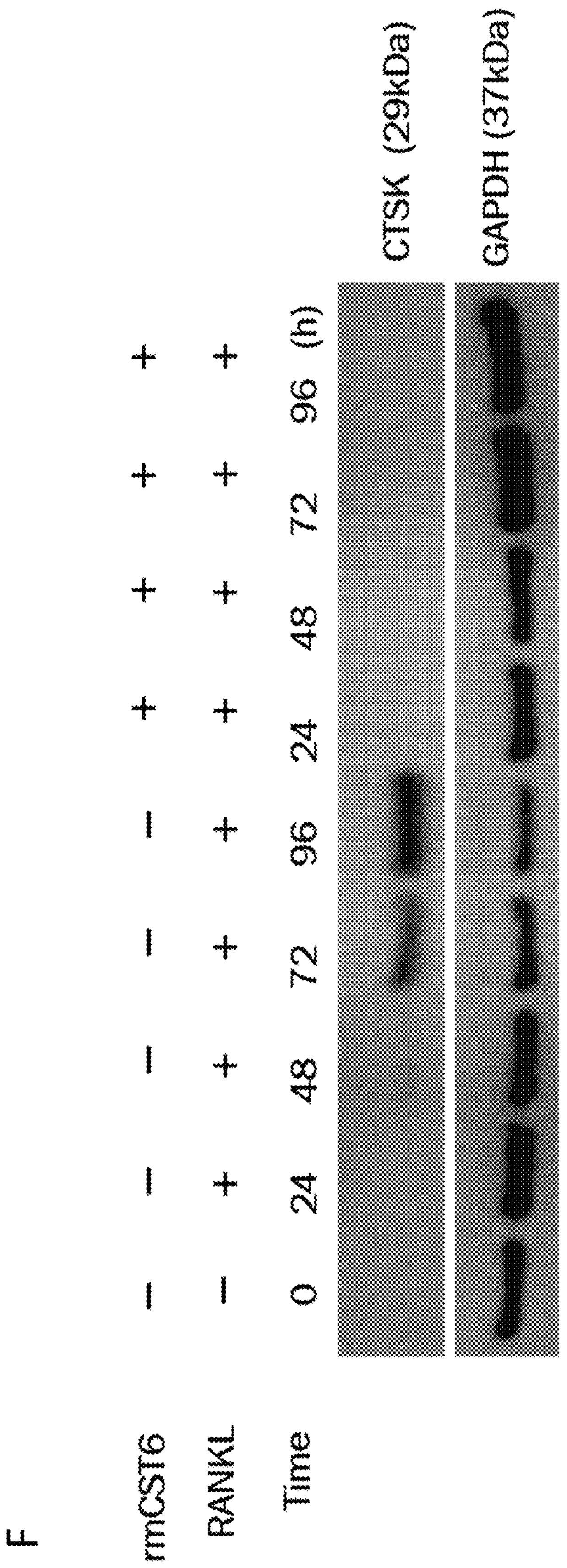

We next evaluated whether BM serum from MM patients with high CST6 expression could also prevent osteoclastogenesis. As shown in FIG. 12C-D, BM serum that contained 200 ng/ml CST6 protein in the culture media significantly blocked osteoclast differentiation and function from human osteoclast precursor cells, and this effect was reversed using anti-CST6 antibody but not by nonspecific mouse IgG. In contrast, BM serum from MM patients with low CST6 expression and healthy donors didn't influence osteoclast differentiation and bone resorption (FIG. 12C-D).

Cystatins are inhibitors of lysosomal cysteine proteases, such as CTSB, CTSL, CTSV and legumain[12]. Thus, we next tested whether CST6 inhibits the activity of cathepsin K (CTSK), an osteoclast-specific cysteine protease involved in bone catabolism[13]. An in vitro fluorimetric assay clearly showed that CST6 was able to inhibit cathepsin K in a dose dependent manner with a 90% inhibition rate at dose of 2.5 nM (FIG. 12E). Further, rmCST6 suppressed the CTSK protein expression induced by RANKL in mouse osteoclast cells differentiation process (FIG. 12F). Together, these data demonstrate that CST6/cystatin M/E can inhibit RANKL-M-CSF-induced osteoclast differentiation and block the function of the osteoclast-specific bone resorbing protease, cathepsin K.

CST6 Protein Inhibits MM Cell-Induced Bone Resorption in an Ex Vivo Model

Figure 13:
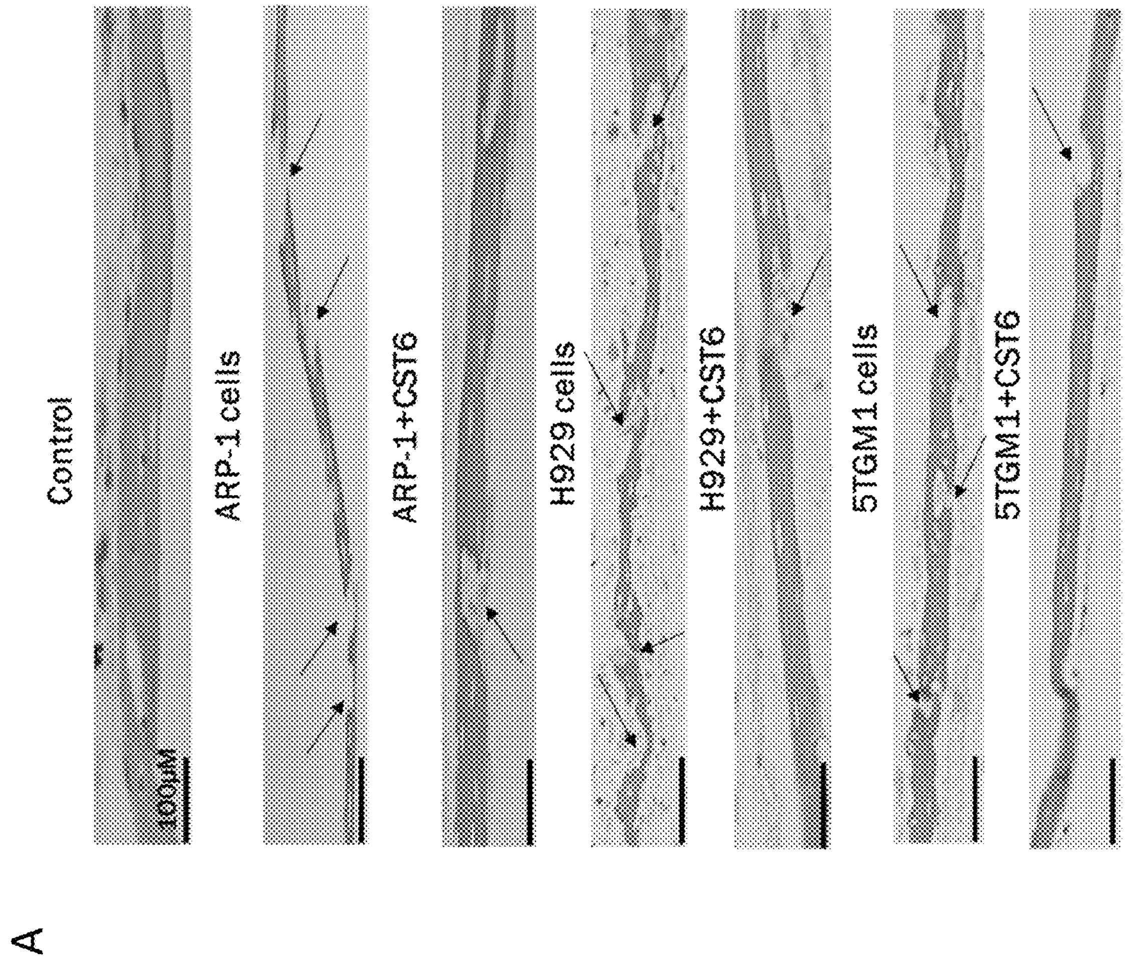
FIG. 13 shows that CST6 suppresses MM-induced bone resorption on calvarial bone ex vivo. (A) H&E sections of the parietal bone region showing osteoclastic bone resorption areas (black arrows). (B) Silver nitrate staining of calvariae show areas with light transparency, which represent bone resorption areas. Scale Bar=100 μm. (C) Bar graphs showing the measured number of bone lytic lesions to bone surface (BS) (left panel) and percentage of resorption area to bone surface (right panel) for each group. Each bar represents the mean (±SD) of triplicate experiments. *p<0.05, p<0.01, *p<0.001, ****p<0.0001. ns, not significant. Statistical analysis was performed using unpaired, 2-sided, independent Student's t test.
Figure 13:
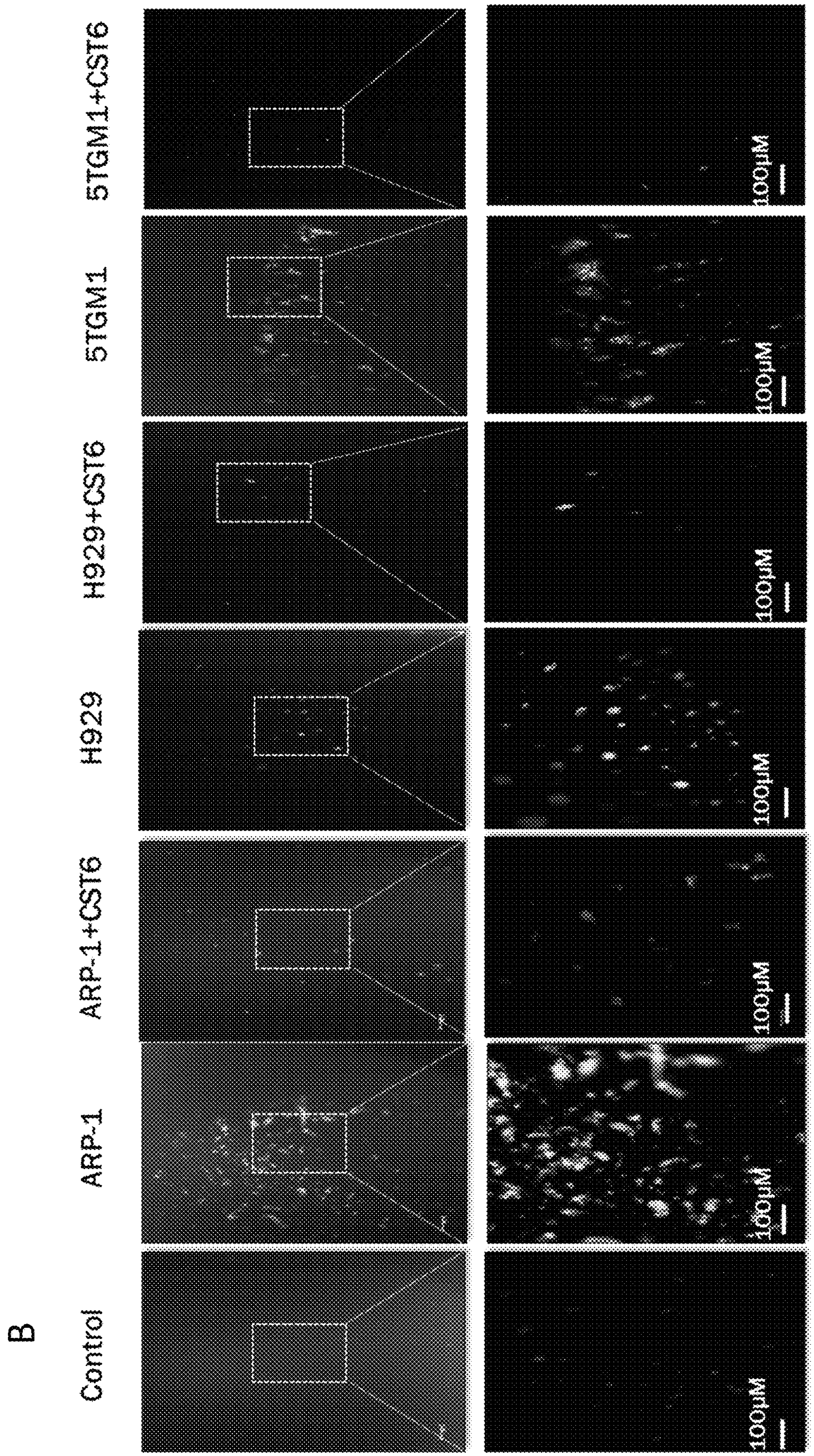
Figure 13:
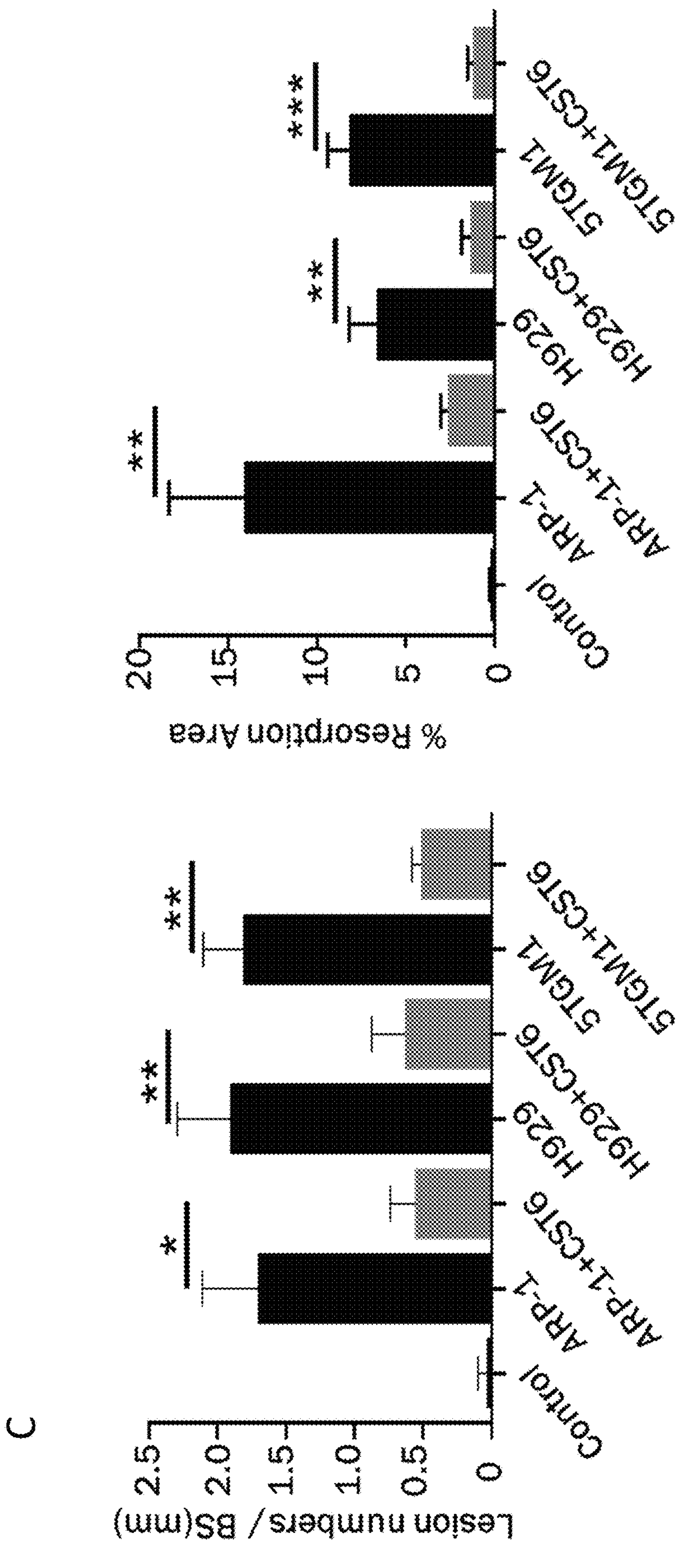

To further determine the potential role of CST6 in bone biology, we employed an ex-vivo organ culture system[14,15]. MM cells co-cultured with calvarial bone will lead to bone resorption. Human MM cell lines ARP1 and H929, as well as the mouse MM cell line, 5TGM1, that do not express CST6, were co-cultured with calvarial bone derived from 10-day-old C57/B6 mice for 10 days with or without rmCST6, after which both H&E and nitrate silver staining were utilized to evaluate the number of bone lesions and bone resorption areas (FIG. 13A-B). Quantification of the mean resorption numbers and transparent bone resorption areas showed that co-culturing CST6 with MM cells significantly decreased calvarial bone lytic lesion numbers and resorption areas (FIG. 13C). These data demonstrate that CST6 can inhibit MM-induced bone resorption in on calvarial bone slices.

CST6 Protein Inhibits MM Cell-Induced Bone Resorption In Vivo

Figure 14:
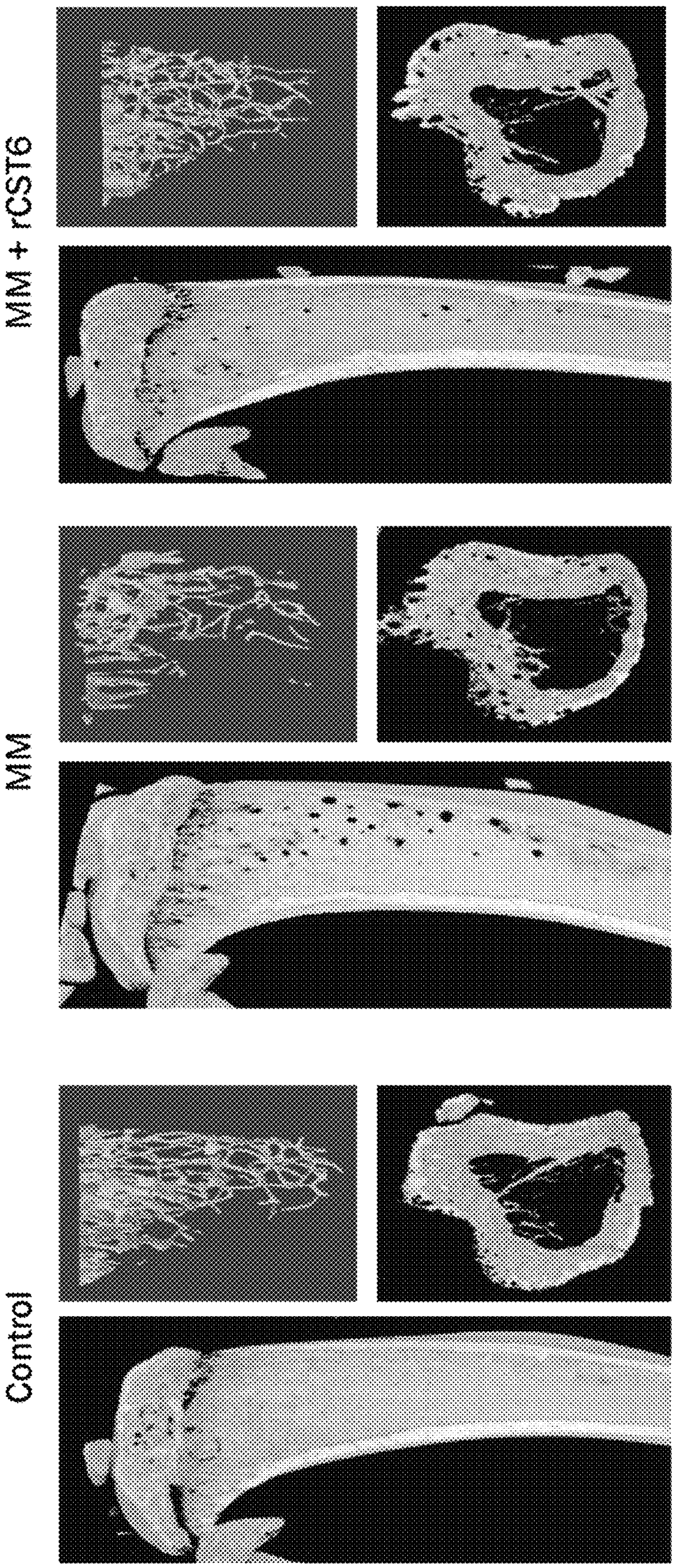
FIG. 14 shows that CST6 inhibits bone destruction in 5TGM1-C57BL/KaLwRij MM mice. 5TGM1 murine MM cells were injected into 8-week-old C57BL/KaLwRij female mice via tail vein. Recombinant mouse CST6 protein was administered on day 5 post tumor inoculation. (A) Reconstructed μCT images of tibia sagittal sections show bone lytic lesions and trabecular architecture. (B) Bar graphs showing the number of bone lytic lesions on the right medial tibia surface and the trabecular bone parameters: bone surface over total volume (BS/TV), bone volume over total volume (BV/TV), trabecular number (Tb.N), trabecular thickness (Tb.Th), trabecular separation (Tb.Sp), and bone mineral density (BMD). (C) TRAP staining shows OCLs (black arrows) in tibia derived from control C57BL/KaLwRij mice without injection of MM cells and C57BL/KaLwRij mice injected 5TGM1 MM cells with or without CST6 treatment. (D) Bar graph showing the results of a histomorphometric analyses of TRAP-stained number of OCLs per bone perimeter (N.Oc/B.Pm) and OCL surface per bone surface (Oc S/BS) in control C57BL/KaLwRij mice and C57BL/KaLwRij mice injected 5TGM1 MM cells with or without CST6 treatment. (E-F) Bar graphs showing the serum levels of the bone resorption marker CTX-1 (E) and bone formation marker PINP (F) detected by ELISA from control C57BL/KaLwRij mice and C57BL/KaLwRij mice injected 5TGM1 MM cells with or without CST6 treatment. (G) Tumor burden was assessed by measuring serum levels of IgG2b (mg/ml) by ELISA from control C57BL/KaLwRij mice and C57BL/KaLwRij mice injected 5TGM1 MM cells with or without CST6 treatment. Data shown as mean±SD (n=6 mice/group). *P<0.05, P<0.01, *P<0.001, ****P<0.0001; ns, not significant. Statistical analysis was performed using unpaired, 2-sided, independent student's t test.
Figure 14:
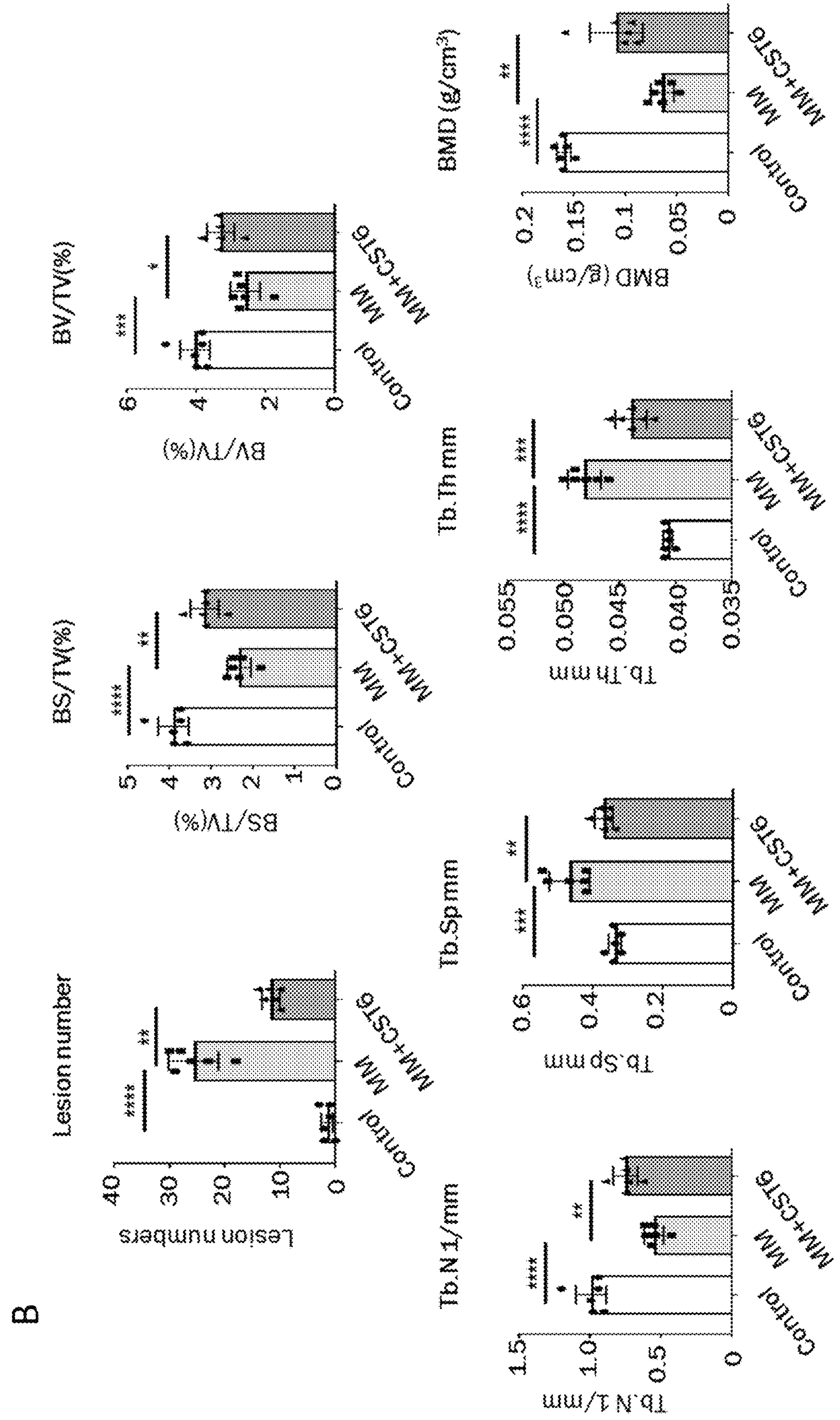
Figure 14:
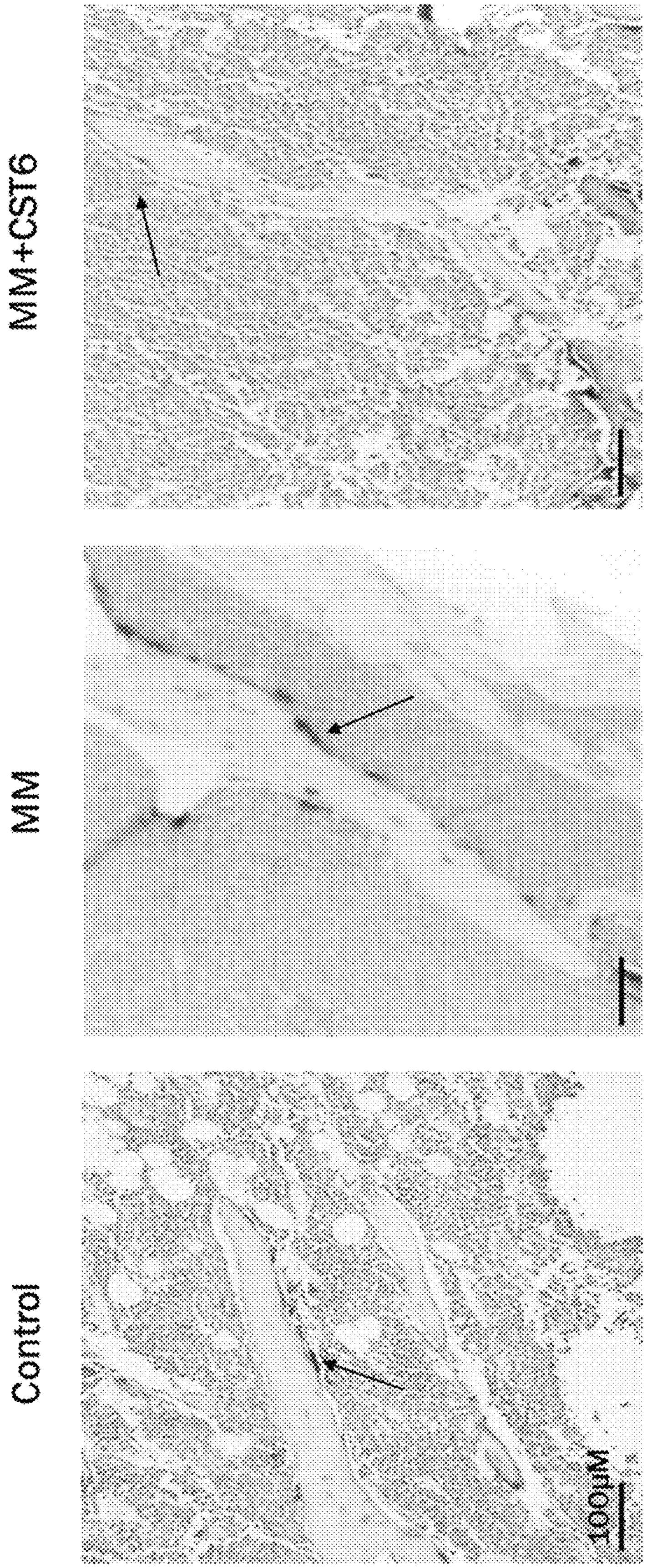
Figure 14:
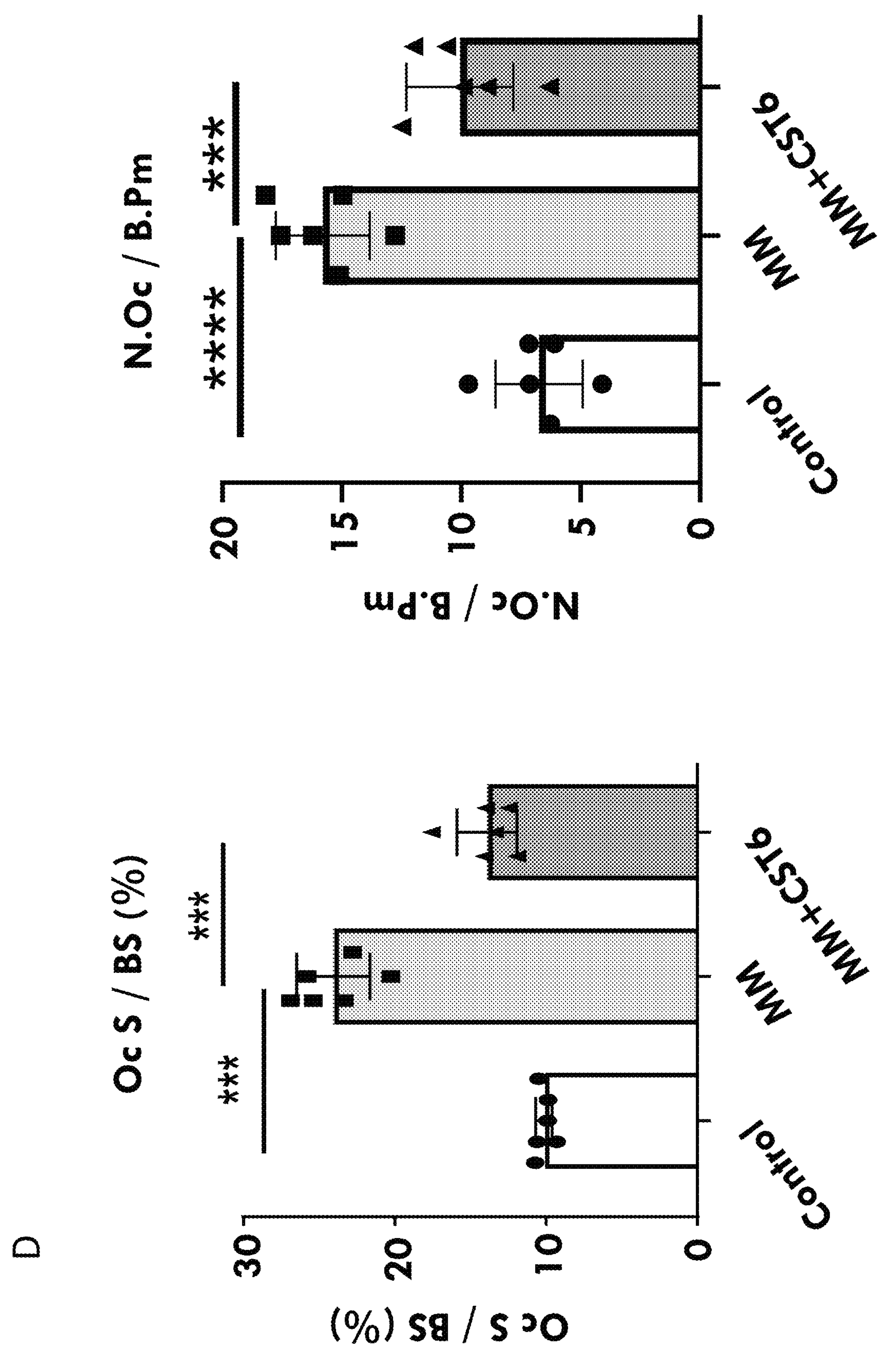
Figure 14:
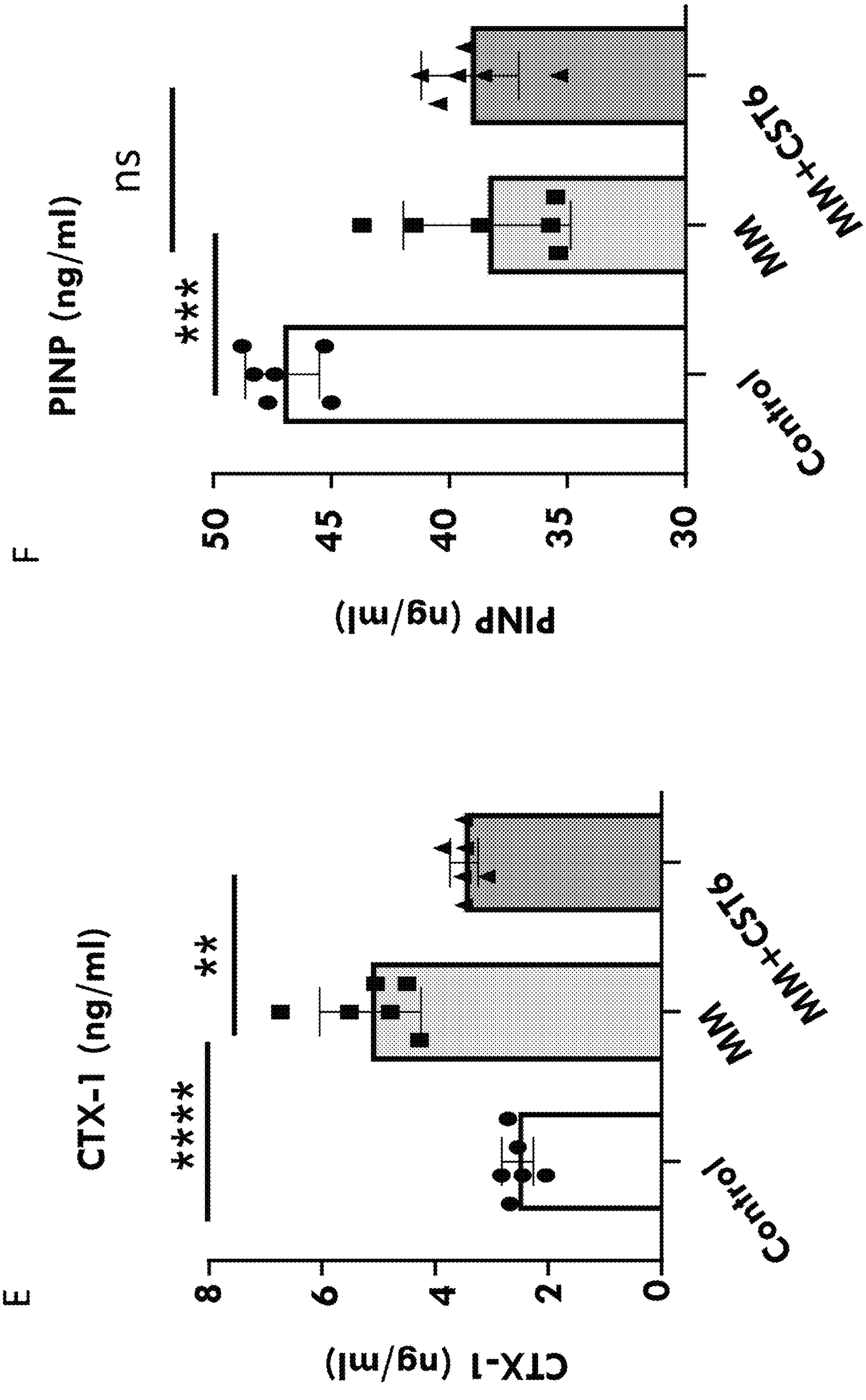
Figure 14:
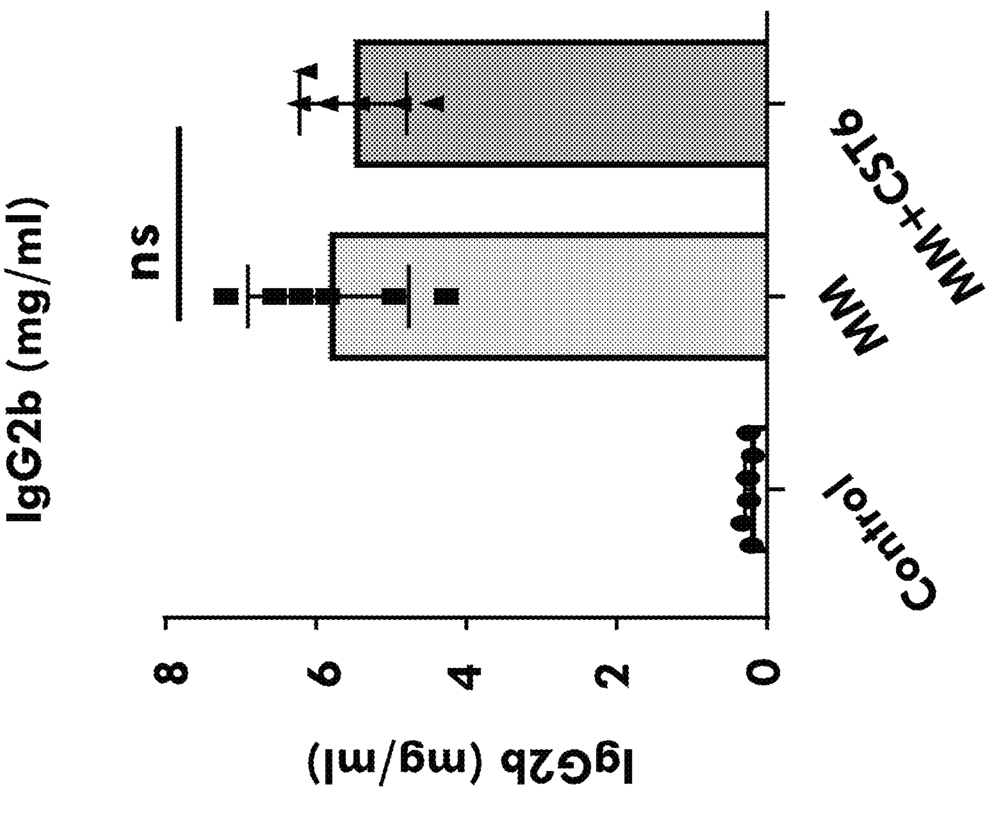
Figure 15:
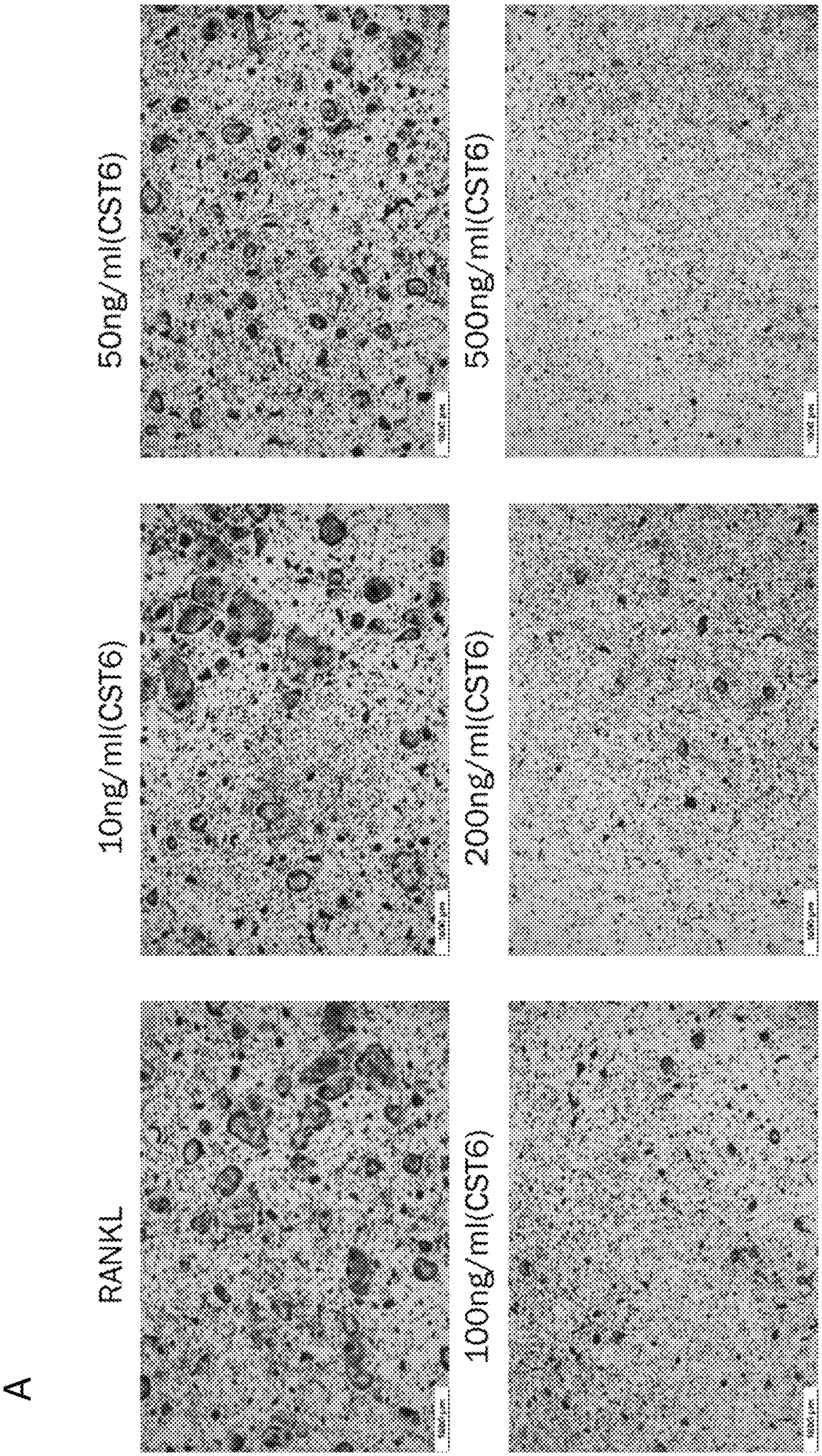
FIG. 15 shows that CST6 inhibits RANKL-induced OCL differentiation and bone resorption. (A) Mouse bone marrow monocytes (BMMs) were seeded into 96 wells at a density of $4\times10^4$ cells/well and cultured with different concentrations of recombinant mouse CST6 protein for 4 days, TRAP staining allowed identification of OCL containing multiple nuclei. (B) Bar graph showing the quantification of TRAP$^+$ OCL cells. (C) Mouse BMMs ($4\times10^4$ cells/well) were seeded into 96 well plate and Corning® Osteo Assay plate. TRAP staining and bone resorption was measured in mouse OCL precursors after culture in the presence of RANKL, +/− rmCST6, +/− anti-CST6 antibody, or +/− non-specific rat IgG for 4 days. (D) Bar graphs showing the quantification of TRAP$^+$ OCL and the bone resorption area. Scale Bar=1000 μm. Each bar represents the mean (±SD) of triplicate experiments. *P<0.05, P<0.01, *P<0.001, ****P<0.0001, ns, not significant. Statistical analysis was performed using unpaired, 2-sided, independent student's t test.
Figure 15:
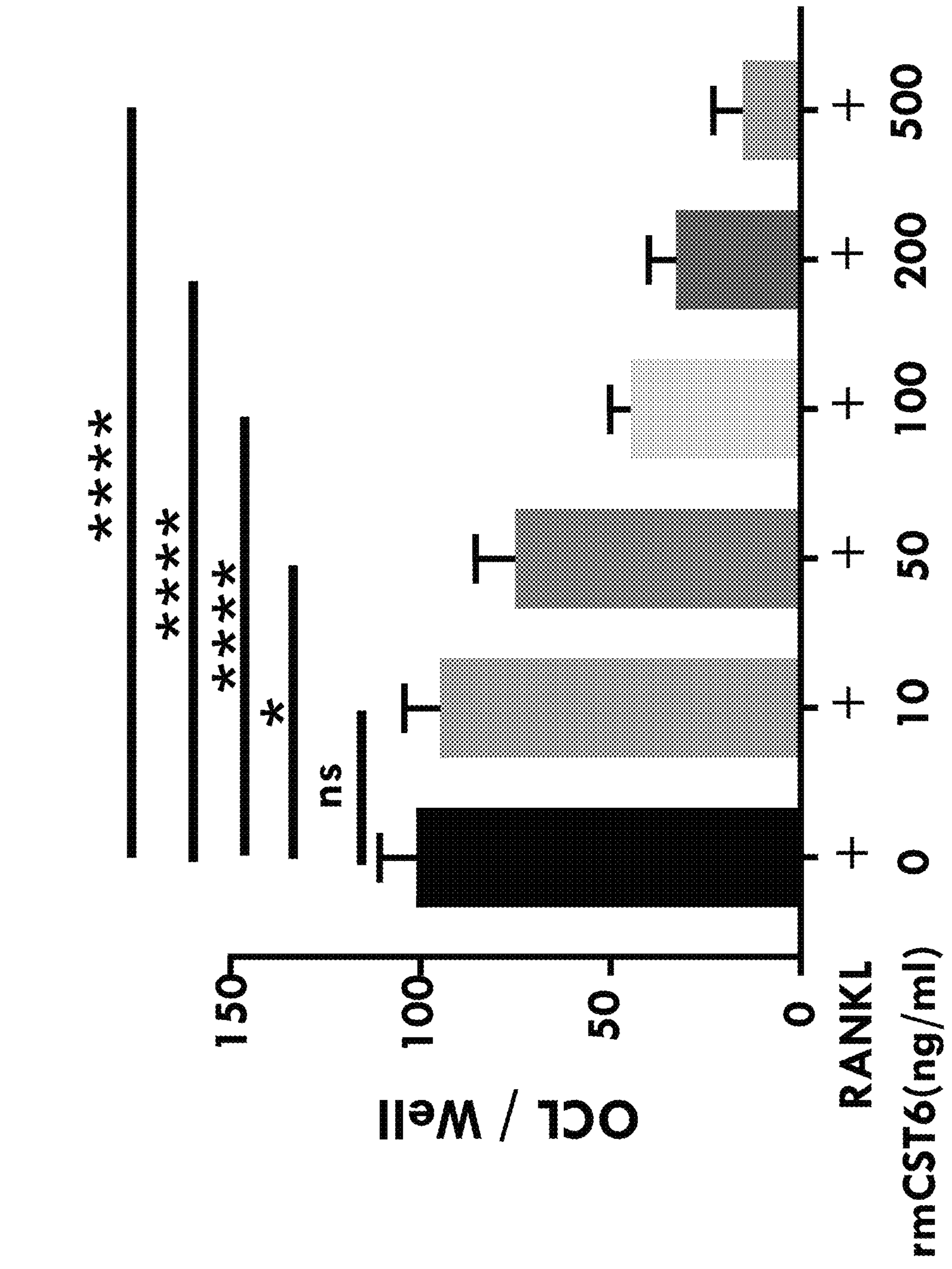
Figure 15:
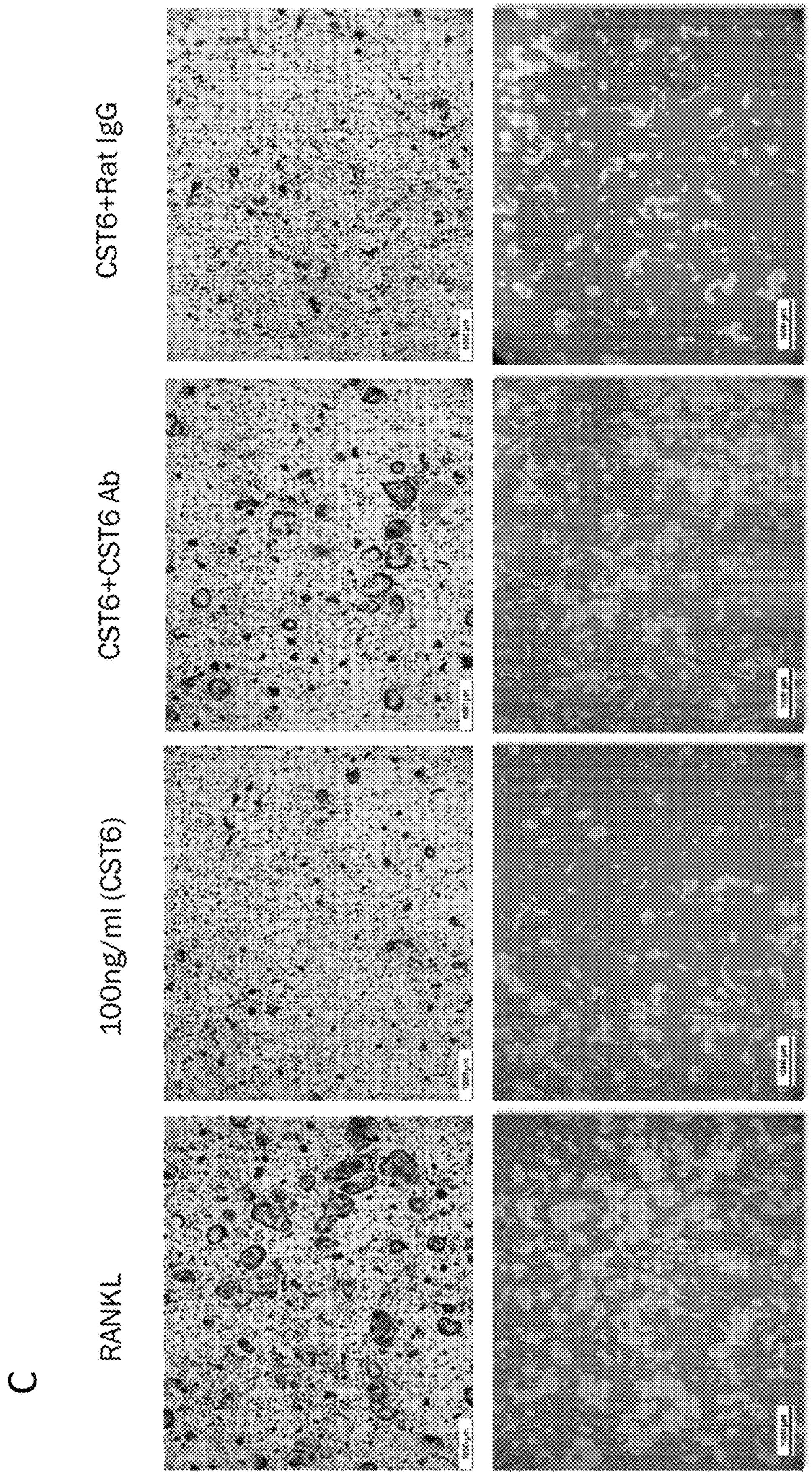
Figure 15:
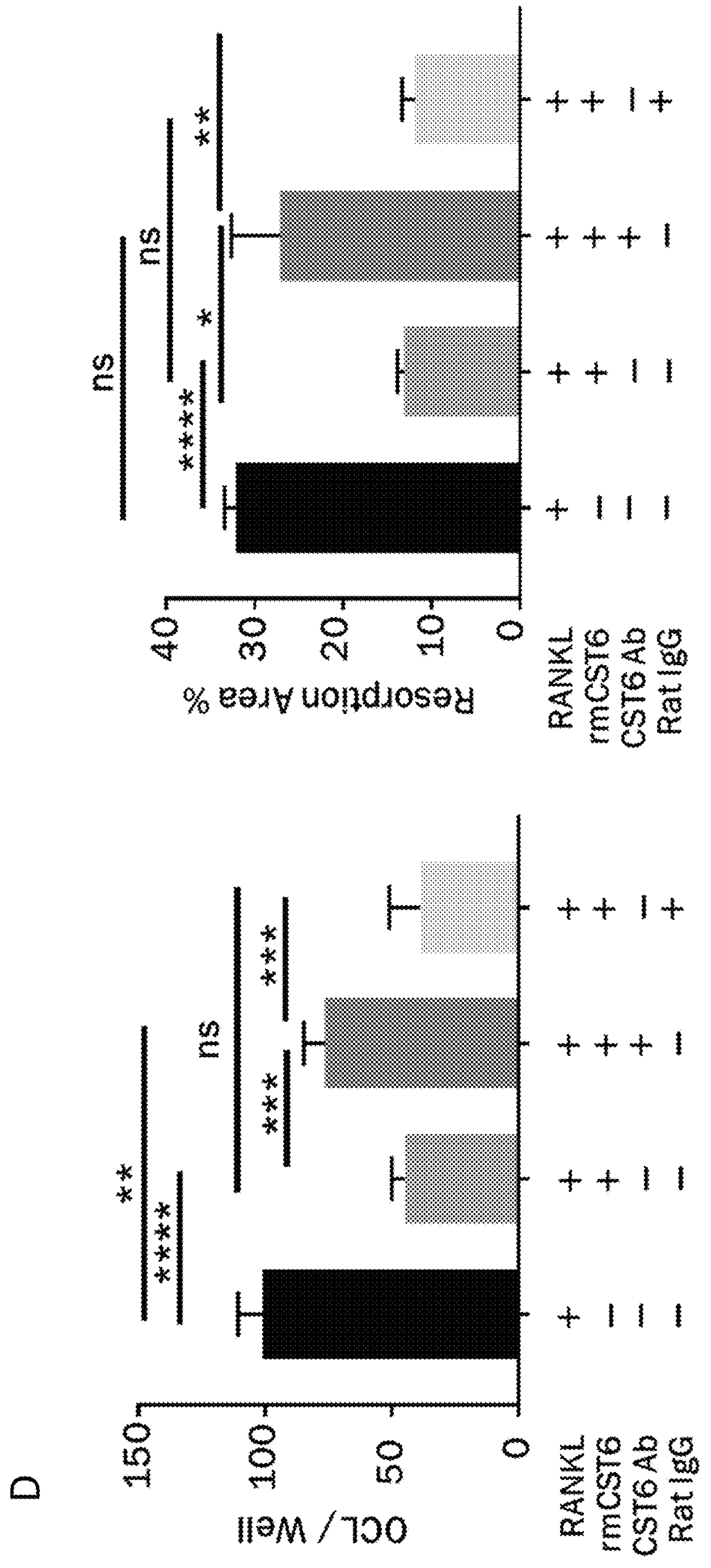

We next utilized the 5TGM1-KaLwRij murine MM model[16] to investigate if CST6 could inhibit bone disease in vivo. One million 5TGM1 cells were inoculated into the C57BL/KaLwRij mice via the tail vein, and mice were treated with purified recombinant mouse CST6 protein (rmCST6). Intraperitoneal injection of CST6 protein (50 μg/kg, once per day) significantly decreased osteolytic lesions in MM-bearing mice (FIG. 14A-B). Micro-CT reconstruction of mouse tibia showed that CST6 protein increased trabecular bone surface over total volume (BS/TV), increased bone volume over total volume (BV/TV), increased trabecular number (Tb.N), increased bone mineral density (BMD), and decreased trabecular separation (Tb.Sp) (FIG. 14A-B). Histomorphometric analyses demonstrated that CST6 administration significantly reduced osteoclast number as well as the proportion of bone surface occupied by osteoclasts in MM-bearing mice (FIG. 14C-D). Consistently, ELISA analysis showed that the collagen type 1 (CTX-1), which is a marker of osteoclast activity, was significantly reduced in mice treated with rmCST6 protein (FIG. 14E). Serum procollagen type I propeptides (PINP), a marker of bone formation, did not show any difference (FIG. 14F), suggesting that CST6 may not alter osteoblast function.

Figure 16:
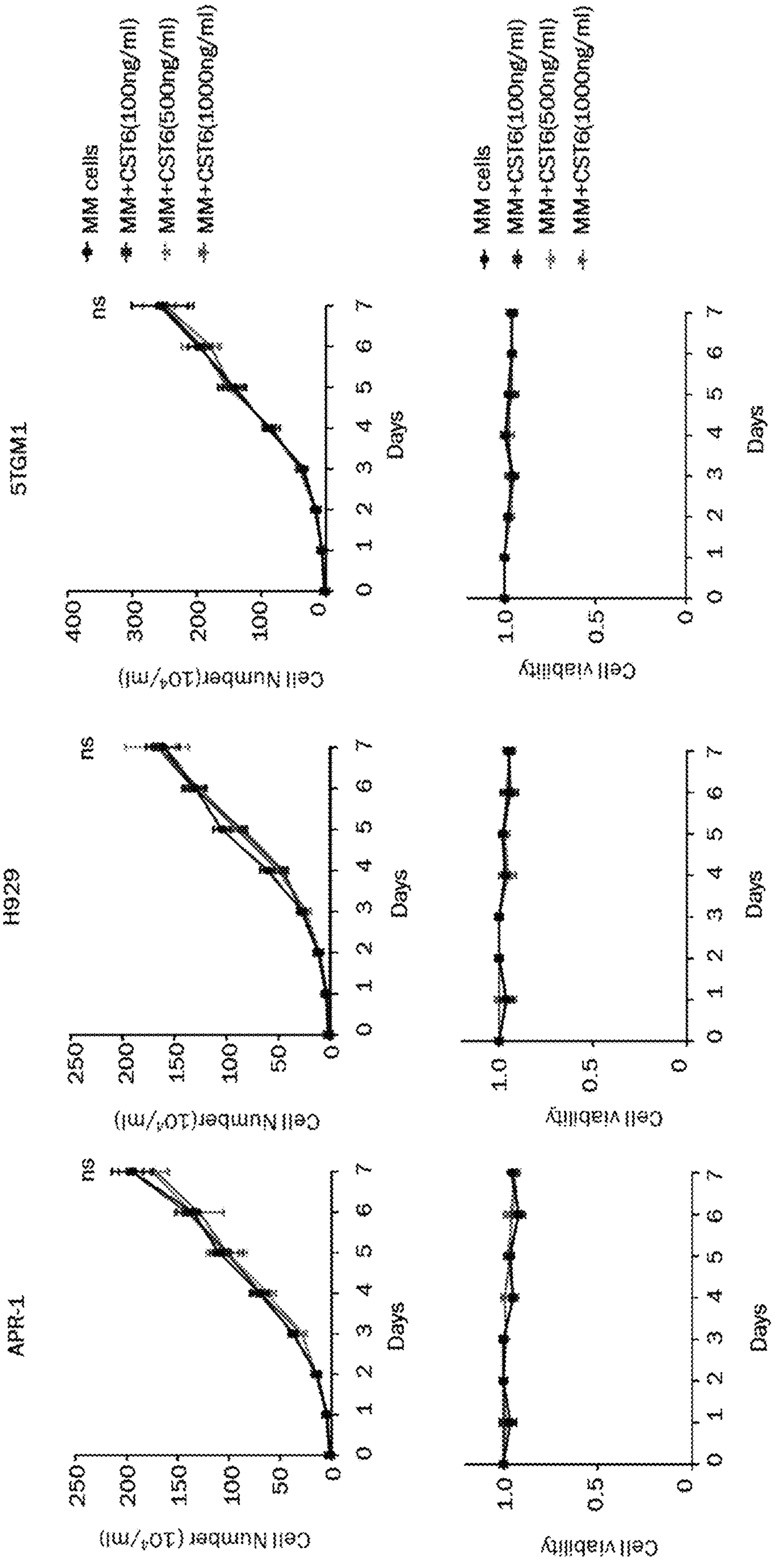
FIG. 16 shows that CST6 does not influence MM cell viability or proliferation. ARP-1, H929, and 5TGM1 MM cells were cultured with different doses of CST6 proteins for 7 days, and cell growth and viability were assessed by trypan blue. Results were expressed as means±SD of three independent experiments. Statistical analysis was performed using unpaired, 2-sided, independent student's t test, ns, not significant.

To elucidate whether CST6 prevents MM cells-induced bone destruction via direct inhibition of tumor cell growth, we measured the M protein IgG2b by ELISA in mouse serum collected from MM-bearing mice, with or without CST6 treatment, that were sacrificed at day 25. No difference was observed between control and CST6-treated groups (FIG. 14G). Further, we did not find any evidence that CST6 influenced MM cell proliferation or survival in vitro (FIG. 16). These data strongly suggest that CST6 has a direct role in the prevention of bone resorption by acting directly on osteoclasts.

Discussion:

Osteolytic bone disease is associated with cancer metastases and is a diagnostic criterion for MM. However, a significant fraction of MM patients will never develop bone disease. The molecular basis for this dramatic difference in disease manifestations is unclear. In a search for bone-disease-modifying genes whose protein products are secreted by MM, we correlated the presence or absence of PET-CT-defined bone lesions in 526 NDMM patients with global gene expression data derived from CD138-selected tumor cells collected from the bone marrow at diagnosis. These data showed that the absence of bone disease was significantly associated with markedly elevated expression of CST6, a cysteine protease inhibitor. Consistent with previous studies, CST6 was inversely correlated with DKK1 in the current cohort of MM. CST6 is expressed at low to undetectable levels in PC from healthy donors. This differs from reports in other cancers that have shown a reduction in CST6 expression in developing gliomas, breast, prostate, and gastric cancers that is often due to hypermethylation of the CST6 promoter[17-22].

We have demonstrated that BM serum from patients with high levels of CST6 expression or recombinant CST6 protein inhibited osteoclast differentiation and bone resorption in vitro, and found that recombinant CST6 suppressed bone loss induced by MM cells using an in vivo mouse model. Based on the strong clinical data suggesting that MM patients with high CST6 expression are much less likely to develop osteolytic lytic lesions along with our experimental confirmation, we conclude that CST6 might represent a potential new anti-resorptive agent. This conclusion is further supported by additional evidence that recombinant CST6 prevents bone loss in ovariectomized mice that mimic post-menopausal osteoporosis (data not shown). As an anti-resorptive agent, CST6 would compete with the therapeutics denosumab and bisphosphonates. Denosumab is expensive to produce and leads to a transient reduction in bone formation. Both agents are linked to osteonecrosis of the jaw. Serum levels of CST6 in MM can be remarkably high. As a comparator, the highest levels of DKK1 we observed in previous studies was 400 ng/ml. In the case of CST6, the majority of cases have greater than 400 ng/ml with the highest being 6913 ng/ml. Yet, in our experience, patients with MM and high levels of serum CST6 do not exhibit an increased incidence of bone manifestations including osteonecrosis of the jaw or other co-morbidities, such as skin and hair dysplasia.

Osteolytic bone metastases are a hallmark of several solid tumors, including lung and breast cancers, and are a direct cause of morbidity and mortality[23]. CST6 has been shown to be downregulated in metastatic breast cancers and ectopic expression of CST6 prevents bone metastases[12]. Taken together with data presented here, these data suggest that downregulation of CST6 in solid tumors may be a key factor in unmasking their osteolytic metastatic phenotypes.

Other class II cystatins, i.e., cystatin B and C, have previously been shown to inhibit bone resorption. Furthermore, cystatin C has been shown to enhance osteoblast differentiation, highlighting the role of endogenous protease inhibitors can play in the regulation of bone metabolism[24-26]. Cystatin C prevents bone resorption mainly by inhibiting the bone matrix degradation[10,27] by interfering with RANKL signal pathway in osteoclast[11] and negatively regulating cathepsin K activity, which is necessary for bone resorption[28]. We found that cystatin C mRNA is highly expressed in PC derived from healthy donors, MGUS, and MM patients (data not shown). High levels of cystatin C are also found in BM serum derived from healthy donors and MM patients (data not shown), suggesting that high cystatin C may not be associated with MM bone disease. In an in vitro assay, CST6 exhibited a 100-fold higher potency in inhibiting osteoclast differentiation and bone resorption compared to cystatin C[10,11] Our study also showed that the anti-CST6 antibody, but not an anti-cystatin C antibody, reversed the effects of High CST6-High cystatin C MM BM serum in inhibiting osteoclast differentiation and activity (data not shown).

CST6 is a cysteine protease inhibitor that regulates lysosomal cysteine proteases and the asparaginyl endopeptidase legumain (LGMN). It is known that CST6 controls the activity of the cysteine proteases cathepsin B (CTSB), cathepsin L (CTSL), cathepsin V (CTSV), and transglutaminase-3 (TGM3)[29-33] The interaction of cystatin M/E with osteoclast-specific cathepsin K (CTSK), has never been studied. Our in vitro assay showed that CST6 protein inhibits 90% of cathepsin K activity at 2.5 nM, strongly suggesting that CST6 prevents bone resorption by inhibiting cathepsin K activity within the ruffled border of the osteoclast. Cathepsin K inhibitors have recently emerged as a new class of anti-resorptive agents, although enthusiasm has been tempered by their lack of specificity[34]. CST6 is normally primarily expressed in the mammary epithelium, the stratum *granulosum* of skin epidermis, sweat glands, hair follicle, and nail[12]. CST6 can be expressed at low levels in normal PC[35]. Whether there is a physiological role for CST6 in normal PC biology is unknown. It is also currently unclear how the CST6 gene is super-activated in MM and if there is a pro-tumor function for CST6. One possibility is that CST6 prevents non-caspase-induced cell death mediated by lysosomal proteases[36]. Another possibility is that CST6 might be promote tumor escape from immune surveillance by preventing the presentation of MHC Class II molecules on the cell surface[37] or preventing T-cell lysosomal protease-mediated cell death[36,38].

Histologically, MM grows in sheets and/or nodules. Osteolytic lesions only develop adjacent to the focal nodules. Thus, the nodular growth of MM, reflected in the presence or absence of PET-CT-defined focal lesions, may be regulated in part by the expression of DKK1 and CST6. DKK1 promotes nodular growth, while CST6 suppresses nodular growth.

Not all MM with osteolytic bone disease express high levels of DKK1 in cells isolated from the iliac crest. Likewise, elevated CST6 is not seen in all cases lacking BD. This could reflect heterogeneity in tumor cell gene expression in a systemic disease and/or point to the existence of multiple mechanisms underlying the development or suppression of osteolytic disease in MM. Nevertheless, the experimentally validated results of correlative studies integrating imaging and genomics strongly suggests that both DKK1 and CST6 represent potent regulators of bone biology.

Materials and Methods:

Patients

We analyzed 526 NDMM patients who had Affymetrix U133Plus2 Chip and PET-CT data taken at diagnosis. The institutional review board of the University of Arkansas for Medical Sciences approved these research studies, and all subjects provided informed consent approving use of their samples for research purposes. Tables 1 shows the characteristics of the patients with MM, and table 2 shows the molecular subgroup designations of these patients.

TABLE 1

Patient characteristics of the 526 patients with multiple myeloma

| Characteristic | No. of Patients/ Total No.(%) | 0 Lesions on PET-CT (N = 185) no./total no.(%) | ≥1 Lesions on PET-CT (N = 341) | P Value |
|---|---|---|---|---|
| Age ≥ 65r | 124/526(23.6) | 47/185(25.4) | 77/341(22.5) | 0.52* |
| White race | 471/526(89.5) | 166/185(89.7) | 301/341(88.2) | 0.67* |
| Female | 198/526(37.6) | 60/185(32.4) | 138/341(40.4) | 0.07† |
| Kappa light chains | 332/525(63.2) | 109/184(59.2) | 223/341(65.3) | 0.16† |
| Lambda light chains | 187/525(35.6) | 74/184(40.2) | 113/341(33.1) | 0.11† |
| IgA subtype | 126/526(23.9) | 40/185(21.6) | 86/341(25.2) | 0.11† |
| Albumin < 3.5 g/dl | 180/526(34.2) | 76/185(41.0) | 104/341(30.4) | 0.016* |
| Beta2-microglobulin ≥ 4 mg/liter | 199/525(37.9) | 67/184(36.4) | 132/341(38.7) | 0.6† |
| C-reactive protein ≥ 4 mg/liter | 380/526(72.2) | 127/185(68.6) | 253/341(74.2) | 0.17* |
| Creatinine ≥ 2 mg/dl (177 μmol/liter) | 39/524(7.3) | 11/183(6.0) | 28/341(8.2) | 0.36* |
| Hemoglobin < 10 g/dl | 126/526(23.9) | 43/185(23.2) | 83/341(24.3) | 0.77† |
| Platelets ≤ 150 × $10^9$/L | 50/526(9.5) | 13/185(7.0) | 37/341(10.8) | 0.15† |
| Lactate dehydrogenase ≥ 190 IU/liter | 144/525(27.4) | 48/185(25.9) | 96/341(28.1) | 0.59† |
| ISS III | 111/526(21.1) | 39/185(21.1) | 72/341(21.7) | 0.99† |
| Risk Score > 0.66 | 82/526(15.6) | 18/185(9.7) | 64/341(18.8) | 0.0064† |
| Bone marrow-biopsy plasma cells ≥ 33% | 254/401(62.5) | 97/146(66.4) | 157/255(61.6) | 0.41† |
| Bone marrow-aspirate plasma cells ≥ 33% | 52/515(10.1) | 13/182(7.1) | 39/333(11.7) | 0.1† |
| Chromosome 1p deletion | 139/525(26.5) | 36/185(19.5) | 103/340(30.3) | 0.007† |
| Chromosome 1q gain | 204/525(38.9) | 81/185(43.8) | 123/340(36.2) | 0.09† |
| Chromosome 1q21 gain | 205/525(39) | 84/185(45.4) | 121/340(35.6) | 0.03† |
| Chromosome 3 gain | 208/525(39.6) | 69/185(37.3) | 139/340(40.9) | 0.45† |
| Chromosome 5 gain | 199/525(37.9) | 59/185(31.9) | 140/340(41.2) | 0.036† |
| Chromosome 6q− | 114/525(21.7) | 36/185(19.5) | 78/340(22.9) | 0.36† |
| Chromosome 7+ | 155/525(29.5) | 45/185(24.3) | 110/340(32.4) | 0.054† |
| Chromosome 9+ | 293/525(55.8) | 99/185(53.5) | 194/340(57.1) | 0.43† |
| Chromosome 11+ | 276/525(52.6) | 90/185(48.6) | 186/340(54.4) | 0.18† |
| Chromosome 13q− | 218/524(41.6) | 71/184(38.6) | 147/340(43.2) | 0.30† |
| Chromosome 15+ | 274/525(52.2) | 95/185(51.4) | 179/340(52.6) | 0.83† |
| Chromosome 19+ | 296/525(56.6) | 98/185(52.9) | 198/340(58.2) | 0.25† |
| Chromosome 21+ | 120/525(22.9) | 39/185(21.1) | 81/340(23.8) | 0.47† |

TABLE 2

Molecular subgroup designations of the 526 patients with multiple myeloma

| Characteristic | No. of Patients/ Total No. (%) | 0 Lesions on PET-CT (N = 185) | ≥1 Lesions on PET-CT (N = 341) | P Value |
|---|---|---|---|---|
| | no./total no. (%) | | | |
| CD-1 | 39/526 (7.4) | 11/185 (5.9) | 28/341 (8.2) | 0.34† |
| CD-2 | 81/526 (15.4) | 29/185 (15.7) | 52/341 (15.2) | 0.89† |
| HY | 165/526 (31.4) | 51/185 (27.6) | 114/341 (33.4) | 0.17† |
| LB | 69/526 (13.1) | 47/185 (25.4) | 22/341 (6.4) | <0.0001† |
| MF | 30/526 (5.7) | 15/185 (8.1) | 15/341 (4.3) | 0.08† |
| MS | 72/526 (13.7) | 25/185 (13.5) | 47/341 (13.8) | 0.93† |
| PR | 70/526 (13.3) | 7/185 (3.8) | 63/341 (18.5) | <0.0001† |

*Fisher's exact test was used.
†The chi-square test was used.

Plasma-Cell Isolation and Gene-Expression Profiling

Gene expression profiling (GEP) and sample preparation were performed as previously described (Blood 2011; 118: 3512-24). The results of gene-expression profiling were deposited in Gene Expression Omnibus (www.ncbi.nlm.nih-.gov/geo/) under the accession number GSE2658.

Bone Imaging

Fluorodeoxyglucose-positron emission tomography-computed tomography (FDG-PET/CT) was performed as previously described (Blood 2009; 114:2068-76). All imaging studies were interpreted by a team of experienced radiologists and nuclear medicine physicians well versed in myeloma diagnostics, who had no prior knowledge of the gene-expression data.

CST6 sandwich ELISA

Nunc™ MaxiSorp™ ELISA Plates (Biolegend, San Diego, CA) were coated with 50 μl of a monoclonal CST6 antibody (R&D Systems, Minneapolis, MN) at a concentration of 2 μg/ml in ELISA coating buffer overnight at 4 °C. The plates were washed and blocked with 1% bovine serum albumin (100 μl/well) at room temperature for 1 h. Plates were washed prior to addition of recombinant CST6 protein (R&D, Minneapolis, MN) for establishment of a standard curve (0-100 ng/ml in ELISA dilution buffer), MMCL conditioned media and patient serum (1:100) samples to each well of the plates and incubated at 4 °C overnight. Plates were washed before incubation with biotinylated polyclonal anti-CST6 antibody (50 μl/well, 0.2 μg/ml in PBS, pH 7.2) (R&D, Minneapolis, MN) at room temperature for 2 h. Plates were then washed prior to incubating each well with 50 μl of a 1:10,000 dilution of streptavidin-horseradish peroxidase (ThermoFisher, Waltham, MA) at room temperature for 1 h. Color development was achieved with the substrate (R&D, Minneapolis, MN) according to manufacturer's instructions and the reaction was stopped by treatment of the plates with 2M sulfuric acid (50 μl/well, 0.5 mol/l). The absorbance values were measured at 450 nm. Validation of the specificity of the CST6 sandwich ELISA was tested by ensuring no color development was evident when recombinant cystatin A, B, C, D, F, S, SN and kininogen proteins (R&D, Minneapolis, MN) were used.

CST6 Expression and Purification

Human and mouse CST6 cDNAs were cloned into pcDNA3.1(+)-C-6His by GenScript (Piscataway, NJ). pcDNA3.1(+)-C-6His-CST6 constructs were transfected into HEK293T cells via Lipofectamine2000 (ThermoFisher, Waltham, MA). Conditioned media was collected at 48 h and 72 h after transfection. The pH of the medium was adjusted to pH7.5-pH8.0 with 0.05M NaOH, then loaded into the HisTrapTMHP column (GE Healthcare, Chicago, IL) using a peristaltic pump at 4 °C. The His-tagged protein was washed with 50 ml of 50 mM Na-Phosphate, 300 mM NaCl, 10% glycerol, 5 mM Imidazole pH 7.5, and eluted with 50 mL 0-100% to 50 mM Na-Phosphate, 300 mM NaCl, 10% glycerol, 300 mM Imidazole pH 7.5 using the NGC column Chromatography System (Bio-Rad, Hercules, CA). After concentration by ultrafiltration, 5 ml sample were loaded onto a Superdex 75 100/300 GL column (GE Healthcare, Chicago, IL) pre-equilibrated with 50 mM Na-Phosphate pH 7.5, 150 mM NaCl, at a flowrate of 0.75 ml/min. The protein purity was determined by silver stain according to the Pierce Silver Stain Kit (ThermoFisher, Waltham, MA) protocol. The concentration of the purified protein was determined at 280 nm by NanoDrop™ 2000 (Thermo Scientific, Waltham, MA). The purified protein was tested for functionality prior to use in in the in vivo tests.

5TGM1 Mouse Model 6-8 week old female C57BL/KaLwRij mice were randomized into groups (n=6/group) and either 100 μL PBS or 1×106 5TGM1-GFP cells were injected intravenously via the tail vein. After 5 days, mice were treated with either PBS or CST6 (50 μg/kg) via intraperitoneal (ip) injection every day. At 25 days post-tumor cell inoculation, when most mice had started to develop paraplegia, the experiment was terminated and the mice were sacrificed. Blood samples were collected every week. All animal procedures adhered to a protocol approved by the local Institutional Animal Care and Use Committee.

Assessment of Tumor Burden and Bone Turnover Markers

Mice were bled every week to harvest serum for detecting IgG2b by ELISA according to the manufacturer's instructions (Bethyl Laboratories, Montgomery, TX). The serum levels of collagen type 1 (CTX-1) and procollagen type I propeptides (PINP) were examined by ELISA using a CTX-1 ELISA kit and PINP ELISA kit (MyBioSource, San Diego, CA) according to the manufacturer's instructions.

Micro-Computed Tomography (μCT)

Mice tibiae were dissected 25 days after tumor injection and fixed in 10% neutral-buffered formalin for 2 days. Micro-CT of mouse Tibia was performed by using SkyScan1272 scanner (Bruker, Belgium). Scans were acquired at 60 kV and 166 uA; Al 0.5 mm filter; 10 uM Pixel size. After scanning, tibia images were reconstructed using the Skyscan NRecon program with a beam hardening correction of 40. Trabecular and cortical bone microarchitecture were analyzed using the Skyscan CT Analyzer program. Osteolytic lesions on the curved medial tibial surface that completely penetrated the cortical bone and were >100 μm in diameter were counted (Nature Communications 2019; 10:4533).

Bone Histomorphometry

Following micro-CT, the same tibiae were decalcified in 5% EDTA solution (pH7.0) for 7 days at room temperature and embedded in paraffin. Bone sections (5 μm thickness) were stained with H&E, tartrate-resistant acid phosphatase (TRAP) using a Leukocyte Acid Phosphatase Kit (Sigma-Aldrich, St. Louis, MO). Histomorphometric analyses were performed using the OsteoMeasure software (OsteoMetrics, Decatur, GA, USA) with a Zeiss Axioskop2 microscope (Carl Zeiss AG).

Cathepsin K Activity Assay

The ability of CST6 (R&D Systems, Minneapolis, MN) to inhibit cathepsin K protease activity was assessed using the cathepsin K Drug Discovery Kit (Enzo Life Sciences International, Plymouth Meeting, PA). Fluorimetric assays were done in triplicate in 96-well microtitre plates using cathepsin K, the fluorogenic synthetic substrate Z-Phe-Arg-AMC in the presence of the cathepsin K assay buffer. Recombinant CST6 was added to assays at various concentrations and the resultant fluorescence was measured using a Biotek Synergy Plate Reader (BioTec, Winooski, VT) with excitation at 380 nm and emission at 460 nm wavelengths. The initial rates determined from the cathepsin K progress curves in the presence of predetermined concentrations of recombinant CST6 were used in Graphpad software (GraphPad Software, San Diego, CA) to determine the inhibition rate.

Preparation of Osteoclasts and Osteoclast Resorption Assays

Human osteoclast precursor cells (Lonza, Basel, Switzerland) were re-suspended to a final concentration of 50,000 cells/mL, and 100 μL were plated per well in a 96-well tissue culture plate and 96 well Corning® Osteo Assay Surface plate (Corning Inc., Corning, NY) in α-MEM medium including 10% FBS, 25 ng/ml M-CSF(R&D), and 50 ng/ml RANKL(R&D) in the absence or presence of CST6 for 7 days. Half-media changes were carried out every 3 days. The cells were then fixed in formalin and stained for TRAP using a TRAP staining kit (Sigma-Aldrich, St. Louis, MO). $TRAP^{+}$ cells containing 3 or more nuclei were counted as OCLs. To analyze the surface for pit formation, the media was aspirated from the wells on day 7, and 100 μL of 10% bleach solution was added. Cells were incubated with the bleach solution for 5 minutes at room temperature. The wells were washed twice with distilled water and allowed to dry at room temperature for 3 to 5 hours. Resorption pits were photographed and analyzed using Image J software (National Institutes of Health, Bethesda, MD, USA). For mouse cell studies, primary mouse bone marrow macrophages (BMMs) were collected from 6-8 week C57BL/6 mice. $4\times10^{4}$ cells were seeded into a 96-well plate with a-MEM containing 10% FBS and 10 ng/ml M-CSF (R&D Systems, Minneapolis, MN) for 3 days to recruit macrophages and then induce osteoclast differentiation plus 10 ng/ml RANKL (R&D Systems, Minneapolis, MN) with or without CST6 for 3-5 days. Half-media changes were carried out every 2 days. The cells were then evaluated for TRAP staining and pit resorptions as before.

Ex Vivo Organ Culture Assay

Calvariae from 10-day old neonatal C57BL/6 mice were dissected as previously described (Methods Mol Biol 2008; 455:37-50; and Cancer Research 2016; 76:6901-10). Half calvarial pieces were co-cultured with $2\times10^{5}$ MM cells in α-MEM/RPMI1640 (Invitrogen, Carlsbad, CA) 50/50 medium supplemented with 1% Penicillin/Streptomycin (Invitrogen, Carlsbad, CA) for 10 days in a six-well plate and the medium was changed every 3 days. At the end of the experiment, half of the calvariae were fixed in 10% formalin for 24 h, decalcified for 48 h in 10% EDTA pH7.2, embedded in paraffin, sectioned, and stained with H&E. The whole length of the slides were captured by the Olympus BX-61 microscope. The quantitative representation of the ex vivo organ culture assay (EVOCA) was performed by calculating bone lesion numbers to whole bone length. The other half of the calvariae were fixed in 10% formalin overnight and counter stained with 2% silver nitrate (Sigma-Aldrich, St. Louis, MO) for 1 h. The mineral loss and bone resorption areas were clearly apparent under the microscope where resorption regions were transparent to light. The transparent areas were quantified and calculated under 10× magnification.

Western Blot

Cells were treated with CST6 at indicated concentration and durations. Cells were lysed in 150 mM NaCl, 10 mM EDTA, 10 mM Tris pH 7.4, and 1% Triton X-100 supplemented with Protease inhibitor (ThermoFisher, Waltham, MA). Protein lysates were incubated on ice for 30 min and centrifuged at 13500 rpm for 4 °C for 10 min. Proteins were separated with NuPAGE 4% to 12% Bis-Tris Gel (Invitrogen, Carlsbad, CA) at 200 V, then transferred to a nitrocellulose membrane for 1 hour at 400 mA at 4 °C. The membrane was blocked for 60 minutes with 5% milk at room temperature. Antibodies against CST6 (R&D Systems), CTSK (Santa Cruz Biotechnology, Dallas, TX), GAPDH (Cell Signal Technology, Danvers, MA) were incubated overnight at a dilution of 1:1,000. Secondary rabbit antibody (Santa Cruz Biotechnology, goat anti-rabbit IgG [H+L], HRP-conjugated) and secondary mouse antibody (Santa Cruz Biotechnology, goat anti mouse IgG-HRP, sc-2005) were incubated for 1 hour at a concentration of 1:10,000. For exposure, Immobilon Western HRP Substrate Peroxide Solution from GE Healthcare was used. Imaging was done with a Bio-Rad (Hercules, CA) ChemiDoc XRS+ with Image Lab Software.

Statistical Analysis

Results are presented as average ±SD or as average ±SEM, as indicated in the Brief Description of the Drawings. Statistical analysis was done using GraphPad Prism 7.0 (GraphPad Software, San Diego, CA). All other comparisons were analyzed by unpaired, 2-sided, independent Student's t test, unless otherwise indicated in the Brief Description of the Drawings. One-way ANOVA analysis of variance was used to determine the statistically significant difference for multiple group comparisons. A P value of less than 0.05 was considered to indicate statistical significance (J Clin Invest 2018; 128:2877-93).

REFERENCES

1. Roodman G D. Pathogenesis of myeloma bone disease. Leukemia 2009; 23:435-41.
2. Tian E, Zhan F, Walker R, et al. The role of the Wnt-signaling antagonist DKK1 in the development of osteolytic lesions in multiple myeloma. N Engl J Med 2003; 349:2483-94.
3. Spencer G J, Utting J C, Etheridge S L, Arnett T R, Genever P G. Wnt signalling in osteoblasts regulates expression of the receptor activator of NFxB ligand and inhibits osteoclastogenesis in vitro. Journal of Cell Science 2006; 119:1283-96.
4. Qiang Y-W, Chen Y, Stephens 0, et al. Myeloma-derived Dickkopf-1 disrupts Wnt-regulated osteoprotegerin and RANKL production by osteoblasts: a potential mechanism underlying osteolytic bone lesions in multiple myeloma. Blood 2008; 112:196-207.
5. Colditz J, Thiele S, Baschant U, et al. Postnatal Skeletal Deletion of Dickkopf-1 Increases Bone Formation and Bone Volume in Male and Female Mice, Despite Increased Sclerostin Expression. Journal of Bone and Mineral Research 2018; 33:1698-707.
6. Zhan F, Huang Y, Colla S, et al. The molecular classification of multiple myeloma. Blood 2006; 108: 2020-8.
7. Bergsagel P L, Kuehl W M, Zhan F, Sawyer J, Barlogie B, Shaughnessy J, Jr. Cyclin D dysregulation: an early and unifying pathogenic event in multiple myeloma. Blood 2005; 106:296-303.
8. Broyl A, Hose D, Lokhorst H, et al. Gene expression profiling for molecular classification of multiple myeloma in newly diagnosed patients. Blood 2010; 116:2543-53.
9. Rajkumar S V, Dimopoulos M A, Palumbo A, et al. International Myeloma Working Group updated criteria for the diagnosis of multiple myeloma. Lancet Oncol 2014; 15:e538-48.
10. Brage M, Lie A, Ransjo M, et al. Osteoclastogenesis is decreased by cysteine proteinase inhibitors. Bone 2004; 34:412-24.
11. Stralberg F, Henning P, Gjertsson I, et al. Cysteine proteinase inhibitors regulate human and mouse osteoclastogenesis by interfering with RANK signaling. FASEB journal: official publication of the Federation of American Societies for Experimental Biology 2013; 27:2687-701.
12. Jin L, Zhang Y, Li H, et al. Differential secretome analysis reveals CST6 as a suppressor of breast cancer bone metastasis. Cell Research 2012; 22:1356-73.
13. Drake M T, Clarke B L, Oursler M J, Khosla S. Cathepsin K Inhibitors for Osteoporosis: Biology, Potential Clinical Utility, and Lessons Learned. Endocrine reviews 2017; 38:325-50.
14. Mohammad K S, Chirgwin J M, Guise T A. Assessing new bone formation in neonatal calvarial organ cultures. Methods Mol Biol 2008; 455:37-50.
15. Xu L, Mohammad K S, Wu H, et al. Cell Adhesion Molecule CD166 Drives Malignant Progression and Osteolytic Disease in Multiple Myeloma. Cancer Research 2016; 76:6901-10.
16. Gooding S, Olechnowicz S W Z, Morris E V, et al. Transcriptomic profiling of the myeloma bone-lining niche reveals BMP signalling inhibition to improve bone disease. Nature Communications 2019; 10:4533.
17. Benezeder T, Tiran V, Treitler A A N, et al. Multigene methylation analysis of enriched circulating tumor cells associates with poor progression-free survival in metastatic breast cancer patients. Oncotarget 2017; 8:92483-96.
18. Peters I, Dubrowinskaja N, Abbas M, et al. DNA methylation biomarkers predict progression-free and overall survival of metastatic renal cell cancer (mRCC) treated with antiangiogenic therapies. PLoS One 2014; 9:e91440.
19. Morris M R, Ricketts C, Gentle D, et al. Identification of candidate tumour suppressor genes frequently methylated in renal cell carcinoma. Oncogene 2010; 29:2104-17.
20. Pulukuri S M, Gorantla B, Knost J A, Rao J S. Frequent loss of cystatin E/M expression implicated in the progression of prostate cancer. Oncogene 2009; 28:2829-38.
21. Qiu J, Ai L, Ramachandran C, et al. Invasion suppressor cystatin E/M (CST6): high-level cell type-specific expression in normal brain and epigenetic silencing in gliomas. Lab Invest 2008; 88:910-25.
22. Veena M S, Lee G, Keppler D, et al. Inactivation of the cystatin E/M tumor suppressor gene in cervical cancer. Genes Chromosomes Cancer 2008; 47:740-54.

23. Coleman R E, Lipton A, Roodman G D, et al. Metastasis and bone loss: advancing treatment and prevention. Cancer Treat Rev 2010; 36:615-20.
24. Laitala-Leinonen T, Rinne R, Saukko P, Vaananen H K, Rinne A. Cystatin B as an intracellular modulator of bone resorption. Matrix Biol 2006; 25:149-57.
25. Suoranta S, Manninen H, Koskenkorva P, et al. Thickened skull, scoliosis and other skeletal findings in Unverricht-Lundborg disease link cystatin B function to bone metabolism. Bone 2012; 51:1016-24.
26. Danjo A, Yamaza T, Kido M A, et al. Cystatin C stimulates the differentiation of mouse osteoblastic cells and bone formation. Biochem Biophys Res Commun 2007; 360:199-204.
27. Lerner U H, Johansson L, Ranjso M, Rosenquist J B, Reinholt F P, Grubb A. Cystatin C, and inhibitor of bone resorption produced by osteoblasts. Acta physiologica *Scandinavica* 1997; 161:81-92.
28. Yamaza T, Tsuji Y, Goto T, et al. Comparison in localization between cystatin C and cathepsin K in osteoclasts and other cells in mouse tibia epiphysis by immunolight and immunoelectron microscopy. Bone 2001; 29:42-53.
29. D'Costa Z C, Higgins C, Ong C W, et al. TBX2 represses CST6 resulting in uncontrolled legumain activity to sustain breast cancer proliferation: a novel cancer-selective target pathway with therapeutic opportunities. Oncotarget 2014; 5:1609-20.
30. Oortveld M A W, van Vlijmen-Willems I, Kersten F F J, et al. Cathepsin B as a potential cystatin M/E target in the mouse hair follicle. FASEB J 2017; 31:4286-94.
31. Zeeuwen P L, van Vlijmen-Willems I M, Cheng T, et al. The cystatin M/E-cathepsin L balance is essential for tissue homeostasis in epidermis, hair follicles, and cornea. FASEB J 2010; 24:3744-55.
32. Cheng T, Hitomi K, van Vlijmen-Willems I M, et al. Cystatin M/E is a high affinity inhibitor of cathepsin V and cathepsin L by a reactive site that is distinct from the legumain-binding site. A novel clue for the role of cystatin M/E in epidermal cornification. J Biol Chem 2006; 281:15893-9.
33. Cheng T, van Vlijmen-Willems I M, Hitomi K, et al. Colocalization of cystatin M/E and its target proteases suggests a role in terminal differentiation of human hair follicle and nail. J Invest Dermatol 2009; 129:1232-42.
34. Mukherjee K, Chattopadhyay N. Pharmacological inhibition of cathepsin K: A promising novel approach for postmenopausal osteoporosis therapy. Biochem Pharmacol 2016; 117:10-9.
35. Hay S B, Ferchen K, Chetal K, Grimes H L, *Salomonis* N. The Human Cell Atlas bone marrow single-cell interactive web portal. Exp Hematol 2018; 68:51-61.
36. Bird P I, Trapani J A, Villadangos J A. Endolysosomal proteases and their inhibitors in immunity. Nat Rev Immunol 2009; 9:871-82.
37. Hartmann S, Lucius R. Modulation of host immune responses by nematode cystatins. Int J Parasitol 2003; 33:1291-302.
38. Schonemeyer A, Lucius R, Sonnenburg B, et al. Modulation of human T cell responses and macrophage functions by onchocystatin, a secreted protein of the filarial nematode *Onchocerca volvulus*. J Immunol 2001; 167:3207-15.

Example 3

In the following Example, the inventors demonstrate that recombinant CST6 protein prevents bone resorption in osteoporosis.

Results:

CST6 Ameliorates Bone Loss in Ovariectomized Mice

Figure 17:
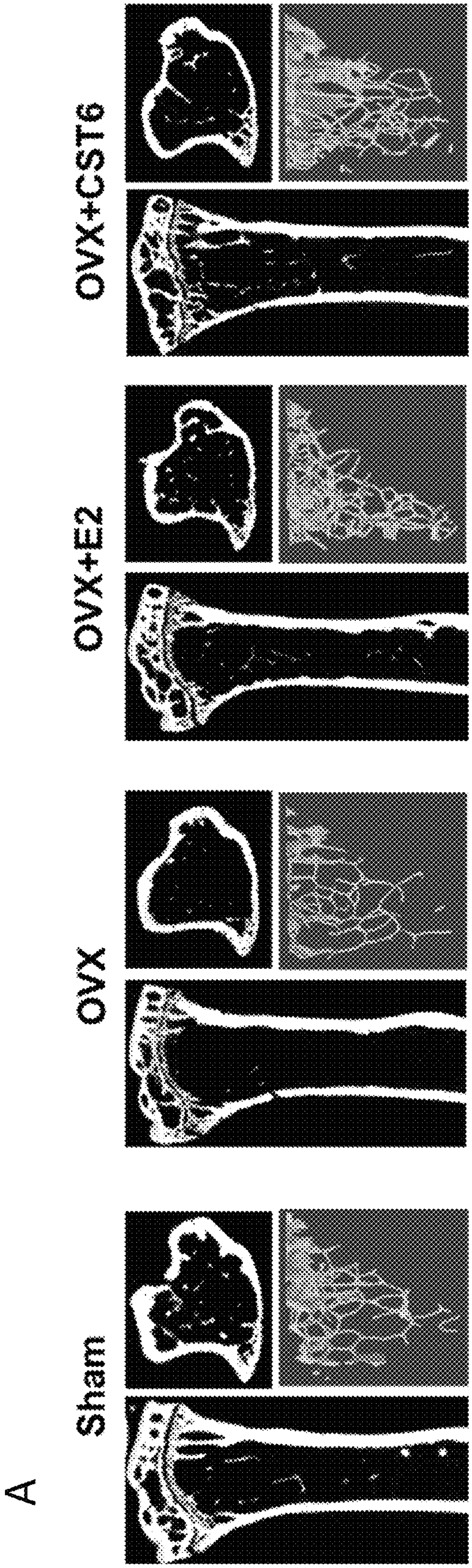
FIG. 17 shows that CST6 suppresses estrogen deficiency-induced bone loss. Ovariectomized (OVX) mice were administered recombinant mouse CST6 protein or 17β-estradiol (E2) for 6 weeks by intraperitoneal (ip) injection every day. (A) Reconstructed μCT images of tibia representing the trabecular architecture. (B) Bar graphs showing measurements of the trabecular bone parameters: bone volume over total volume (BV/TV), trabecular number (Tb.N), trabecular thickness (Tb.Th), trabecular separation (Tb.Sp), and bone mineral density (BMD). (C) Representative TRAP staining showing osteoclasts (red color) (D) Bar graphs showing measurements of the number of osteoclasts per bone perimeter (N.Oc/B.Pm) and osteoclast surface per bone surface (Oc.S/BS). (E-F) ELISA was performed on mouse serum to detect the bone turnover markers CTX-1 (E) and PINP (F). The values are the mean (±SD) of 8-10 mice per group. *P<0.05, P<0.01, *P<0.001, ****P<0.0001; ns, not significant. Statistical analysis was performed using unpaired, 2-sided, independent student's t test.
Figure 17:
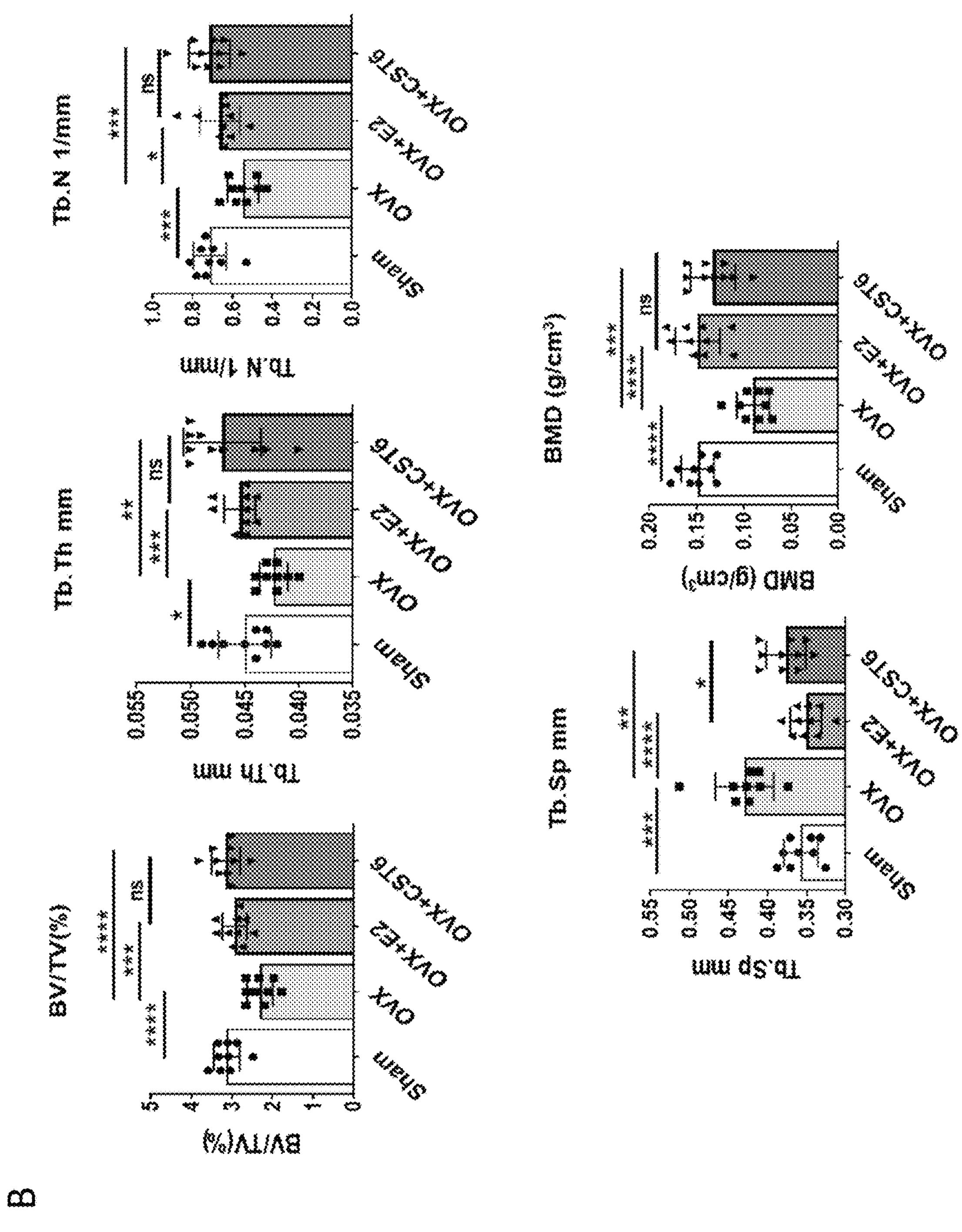
Figure 17:
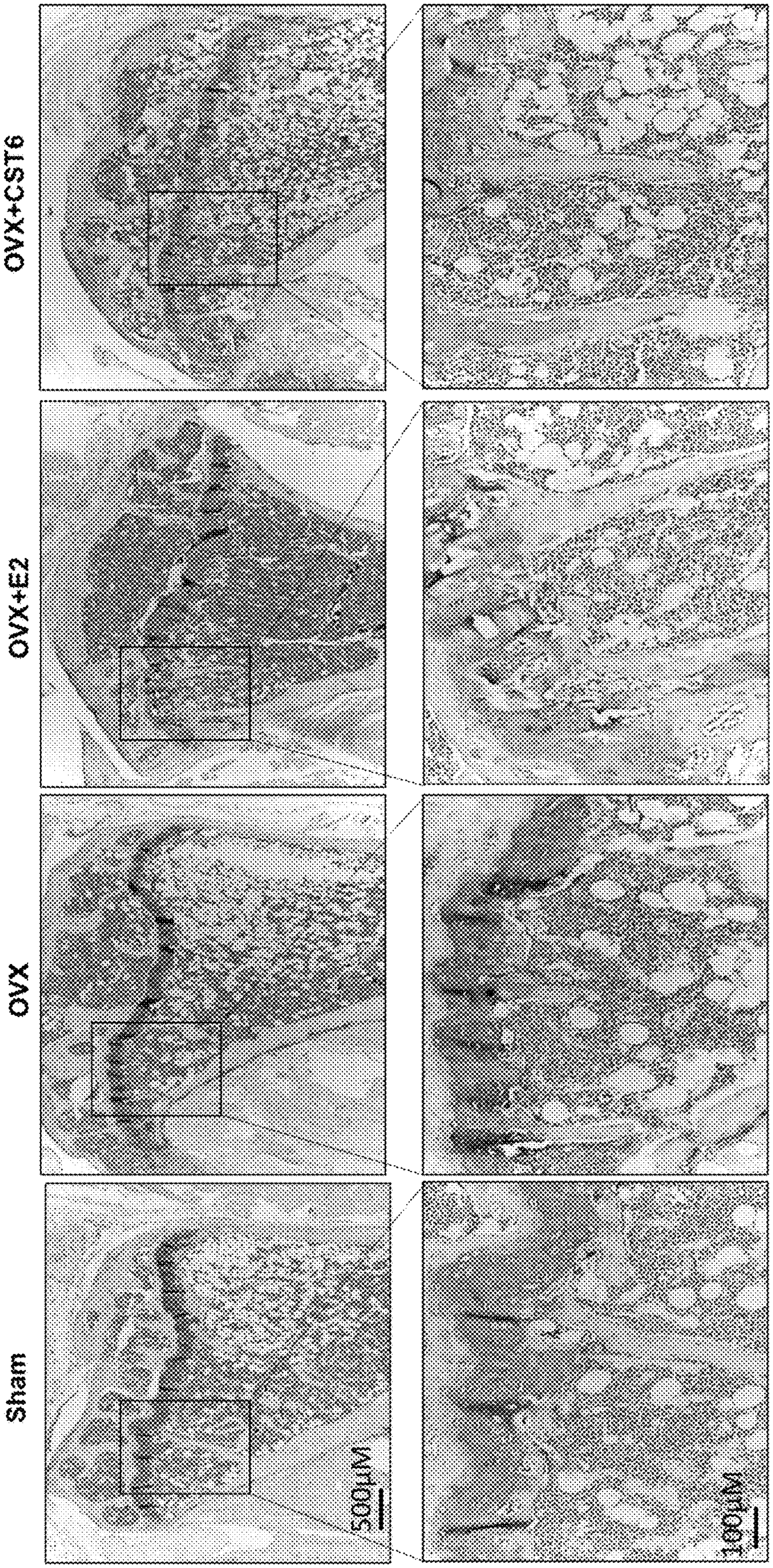
Figure 17:
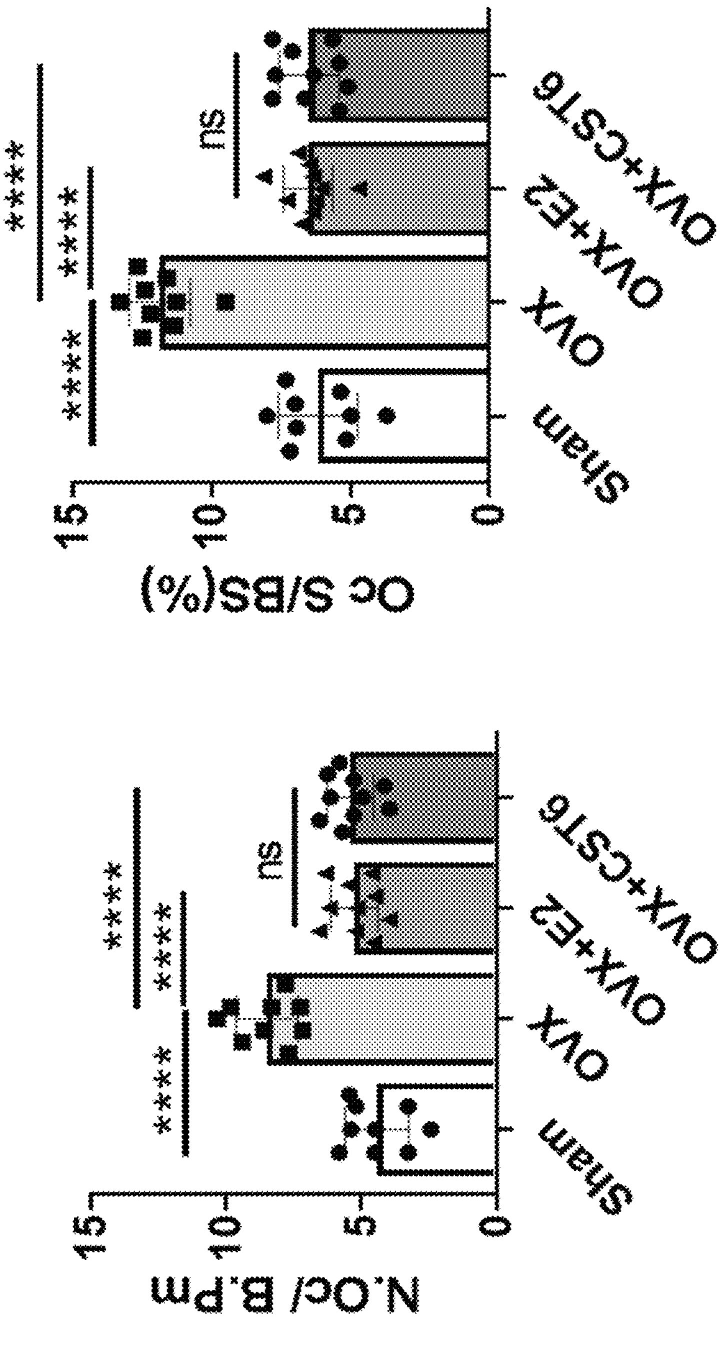
Figure 17:
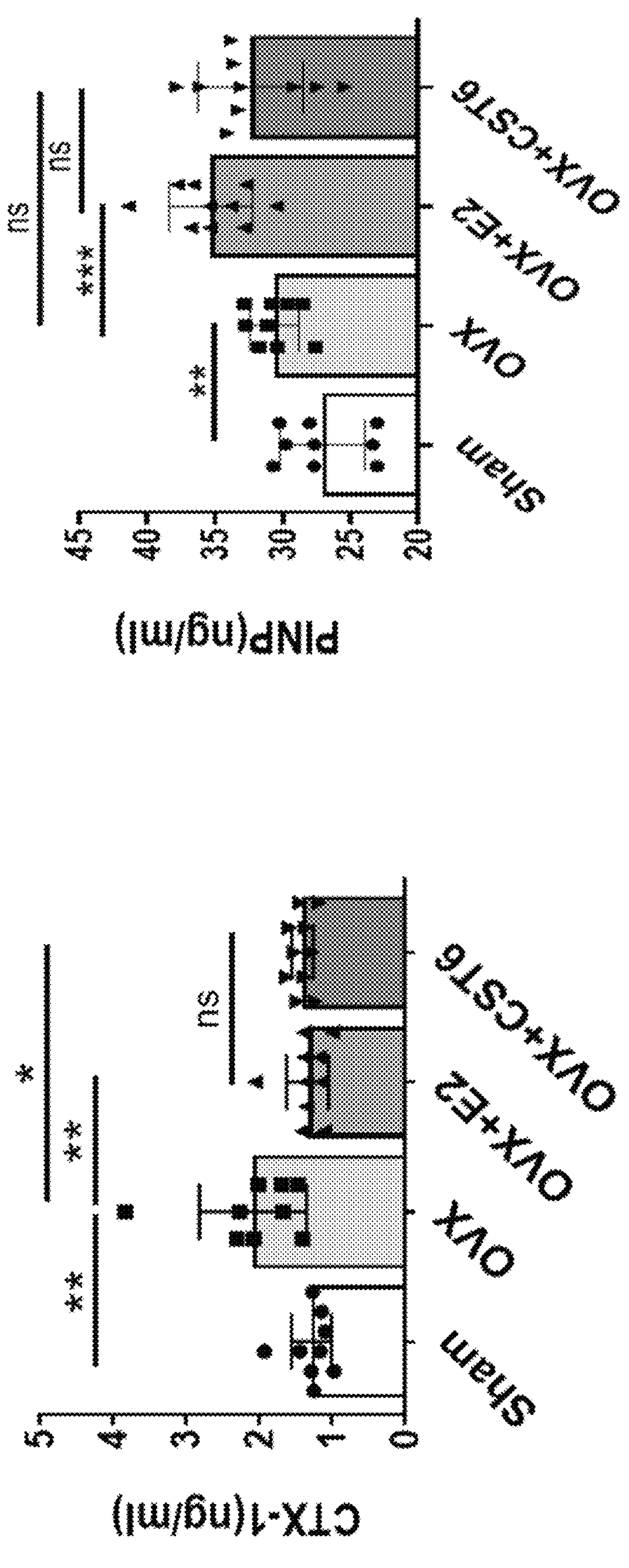
Figure 18:
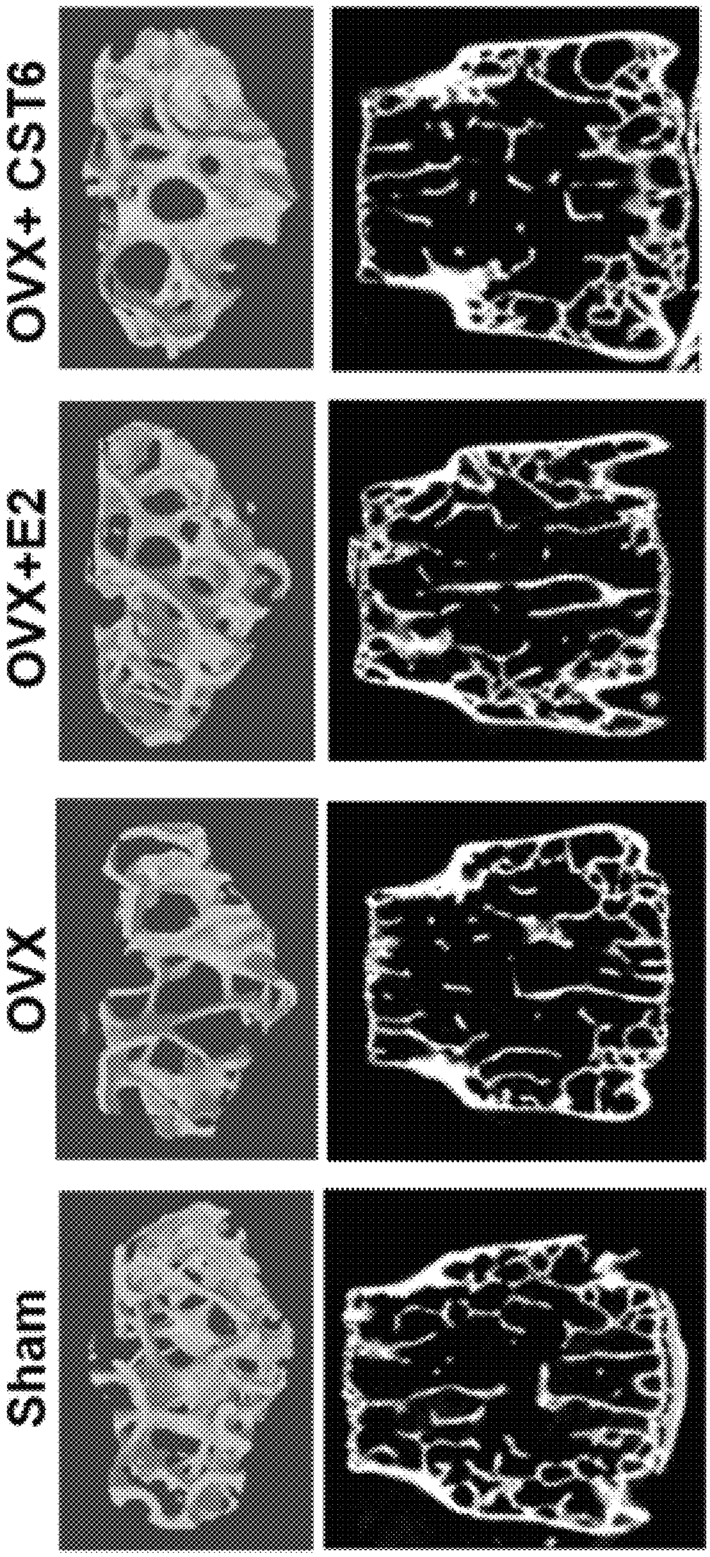
FIG. 18 shows that CST6 treatment prevents ovariectomy-induced bone loss in vertebrae. (A) Reconstructed μCT images of vertebrae (L5). (B) Bar graphs showing that both E2 and CST6 protein significantly improved bone parameters, including bone volume over total volume (BV/TV), trabecular thickness (Tb.Th), trabecular number (Tb.N), bone surface over total volume (BS/TV), bone mineral density (BMD), and trabecular separation (Tb.Sp).
Figure 18:
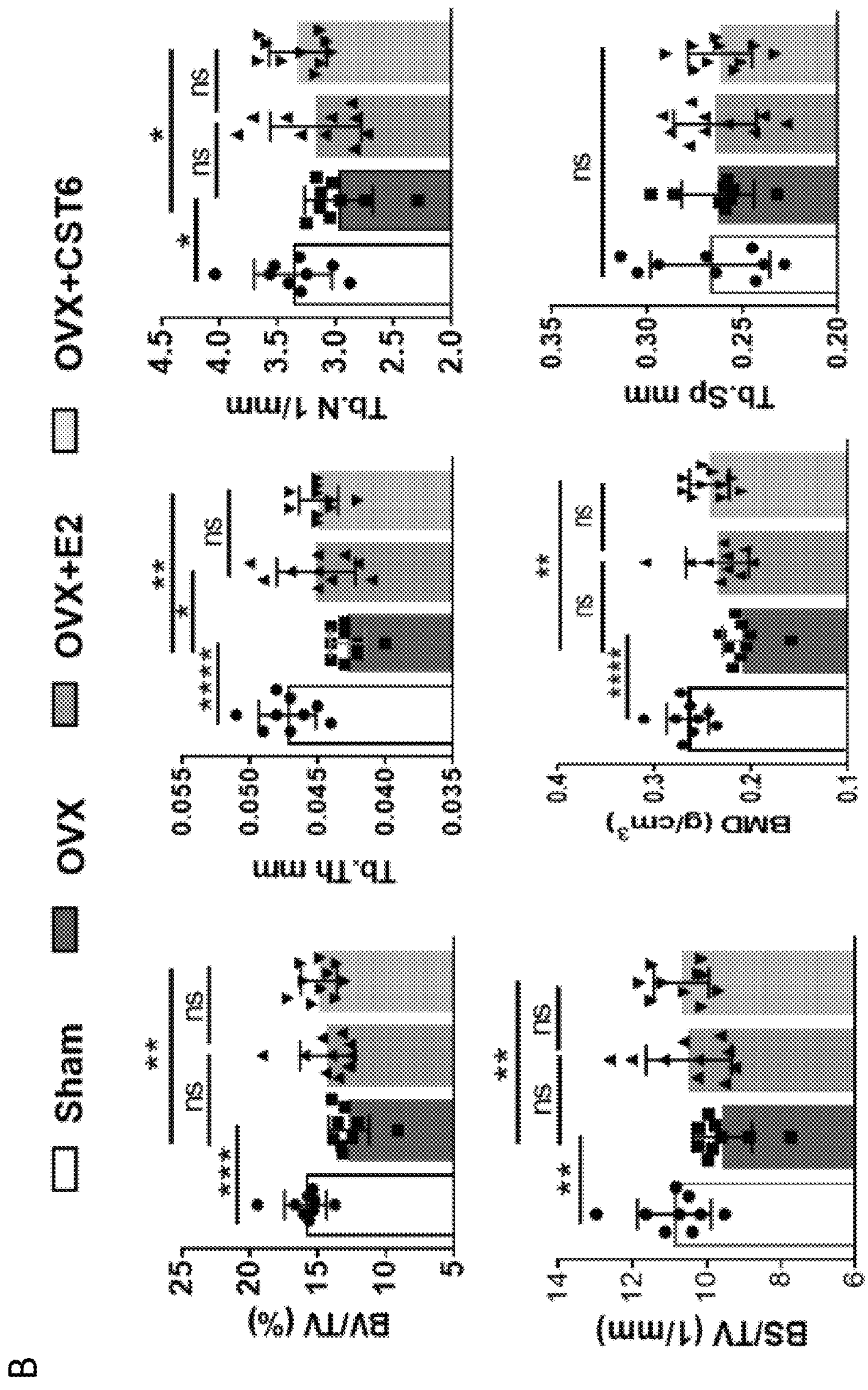

We next sought to determine whether CST6 plays a role in preventing bone resorption in other bone disease beyond MM. Ovariectomized (OVX) mice were used as a model of postmenopausal osteoporosis in this study. Two days after surgery, six-month-old C57/BL6 OVX mice were treated with PBS, 17β-estradiol (E2) as a positive control or CST6 (50 g/kg) for 6 weeks. Mouse tibia were analyzed by CT and histology. Compared with the sham group, the tibia from the OVX mice exhibited significant bone loss (FIG. 17A). Like E2 hormone, CST6 protein significantly prevented OVX-induced bone loss. Quantitative analysis confirmed that bone parameters, including BV/TV, Tb.N, Tb.Th, Tb.Sp and BMD, were improved in the E2 and CST6 treatment groups (FIG. 17A-B). CT was also performed on vertebrae (L5), both E2 and CST6 protein significantly antagonized bone loss and improved those bone parameters, including bone volume over total volume (BV/TV), trabecular thickness (Tb.Th), trabecular number (Tb.N), bone surface over total volume (BS/TV), bone mineral density (BMD), and trabecular separation (Tb.Sp) (FIG. 18A-B). Bone histomorphometry analysis demonstrated that CST6 protein significantly reduced the osteoclast number and the proportion of bone surface occupied by osteoclasts in OVX mice (FIG. 17C-D).

ELISA analyses showed that the collagen type 1 (CTX-1), which is a marker of osteoclast activity, was significantly reduced in mice treated with rmCST6 protein (FIG. 17E). Serum PINP, a marker of bone formation, did not show any difference (FIG. 17F), suggesting that CST6 may not alter osteoblast function. These data strongly suggest that CST6 has a direct role in the prevention of bone resorption by acting directly on osteoclasts.

CST6 Inhibits Osteoclastogenesis Through Attenuating RANKL-Induced NF-κB Signaling Pathway To examine the mechanism through which recombinant mouse CST6 (rmCST6) inhibits the osteoclast differentiation, western blot was utilized to detect osteoclastogenesis proteins. NFATc1 is master regulator of RANKL-induced osteoclast differentiation, which regulates a number of osteoclast-specific genes such as TRAP, cathepsin K, calcitonin receptor, and osteoclast-associated receptor (OSCAR) through cooperation with MITF and c-Fos. Western blot showed that RANKL activated the expression of NFATc1, c-Fos, and ctsk mainly after 2 days, whereas expression of these genes was downregulated after treatment with rmCST6 (FIG. 19A). RANKL stimulates osteoclast formation mainly through the canonical and non-canonical NF-κB signaling pathway. RANKL induces the activation of canonical NF-κB signaling pathway by recruiting TRAF6 to the IκB kinase complex, which induces the phosphorylation and degradation of IκBα followed by the nuclear translocation of p65 and p50. In non-canonical NF-κB signaling, RANKL induces the ubiquitination and lysosomal degradation of TRAF3, which results in processing of p100 to p52 and nuclear translocation of p52 and RelB[1].

To further test the mechanism through which CST6 suppresses osteoclastogenesis, osteoclast precursor cells were pretreated with rmCST6 for 30 min before being stimulated with RANKL. Western blot analysis showed that rmCST6 had no significant effect on the degradation of IκBα and phosphorylation of p65 (FIG. 19B), suggesting that rmCST6 does not influence the classical NF-κB signaling pathway. On the other hand, the lysosomal inhibitor chloroquine was shown to suppress osteoclastogenesis by inhibiting p100 processing and stabilizing TRAF3[2,3]. To test the non-canonical signaling pathway, osteoclast precursor cells were treated with RANKL with or without rmCST6 for 8 hours. Western blot analysis showed that RANKL induced the processing of p100 to p52 and the degradation of TRAF3. However, this effect was blocked by rmCST6 treatment, indicating that rmCST6 suppresses osteoclast formation in a TRAF-3 dependent manner (FIG. 19C).

Materials and Methods:

CST6 Expression and Purification

Human and mouse CST6 cDNA were cloned into pcDNA3.1(+)-C-6His by GenScript company. pcDNA3.1 (+)-C-6His-CST6 constructs were transfected into HEK293T cells via Lipofectamine2000 (ThermoFisher, Waltham, MA). Conditional media was collected 48 h and 72 h after transfection. The pH of the medium was adjusted to pH7.5-pH8.0 with 0.05M NaOH, and then the sample was loaded into a HisTrapTMHP column (GE Healthcare, Chicago, IL) with a peristaltic pump at 4 °C. The His-tagged protein was washed with 50 ml 50 mM Na-Phosphate, 300 mM NaCl, 10% glycerol, 5 mM Imidazole pH 7.5, and eluted with 50 mL 0-100% to 50 mM Na-Phosphate, 300 mM NaCl, 10% glycerol, 300 mM Imidazole pH 7.5 on NGC Chromatography System (Bio-Rad, Hercules, CA). After concentration by ultrafiltration, 5 ml samples were loaded onto a Superdex 75 100/300 GL column (GE Healthcare) pre-equilibrated with 50 mM Na-Phosphate pH 7.5, 150 mM NaCl, at a flowrate of 0.75 ml/min. The protein purity was determined by silver stain according to the Pierce Silver Stain Kit (ThermoFisher) protocol. The concentration of the purified protein was determined at 280 nm by NanoDrop™ 2000 (Thermo scientific).

OVX Mouse Model

Female 6-month-old C57BL/6J mice (Jackson Laboratories) were used in this study. Mice were anesthetized with chloral hydrate and subjected to ovariectomy or sham operation. After being ovariectomized (OVX), mice were randomly divided into 4 groups to receive the following treatments: (1) sham group (sham operations+PBS, n=9), (2) vehicle group (OVX+PBS, n=9), (3) 17β-estradiol (E2) group (OVX+17β-estradiol, 0.25 μg/kg, n=10), (4) CST6 group (OVX+CST6, 50 μg/kg, n=10). After 2 days to allow recovery from the surgery, mice were administered various drugs for 6 weeks via intraperitoneal (ip) injection every day. After sacrifice, serum, legs, and vertebras were collected and stored at −80 °C until use.

Micro-Computed Tomography (μCT)

Micro-CT of mouse tibia was performed using a SkyScan1272 scanner (Bruker, Belgium). Scans were acquired at 60 kV and 166 uA; Al 0.5 mm filter; 10 uM Pixel size. After scanning, tibia images were reconstructed using the Skyscan NRecon program with a beam hardening correction of 40. Trabecular and cortical bone microarchitecture were analyzed using the Skyscan CT Analyzer program.

Bone Histomorphometry

Following micro-CT, the same tibiae were decalcified in 5% EDTA solution (pH7.0) for 7 days at room temperature and embedded in paraffin. Bone sections (5 μm thickness) were stained with H&E, tartrate-resistant acid phosphatase (TRAP) using a Leukocyte Acid Phosphatase Kit (Sigma-Aldrich). Histomorphometric analyses were performed using the OsteoMeasure software (OsteoMetrics, Decatur, GA, USA).

Assessment of Tumor Burden and Bone Turnover Markers

Blood was taken by cardiac puncture immediately after the mice were sacrificed. Serum was prepared by centrifugation of clotted blood at 4500 rpm for 15 min. Serum aliquots were frozen immediately at −80 °C. The serum levels of CTX-1 and PINP were examined by ELISA using a CTX-1 ELISA kit and PINP ELISA kit (MyBioSource, San Diego, CA) according to the manufacturer's instructions.

Western Blot

Cells were treated with CST6 at various concentrations and durations. Cells were lysed in 150 mM NaCl, 10 mM EDTA, 10 mM Tris pH 7.4, and 10% Triton X-100 supplemented with Protease inhibitor (ThermoFisher, Waltham, MA). Protein lysates were incubated on ice for 30 min and centrifuged at 13500 rpm for 4 °C for 10 min. Proteins were separated with NuPAGE 4% to 12% Bis-Tris Gel (Invitrogen, Carlsbad, CA) at 200 V, then transferred to a nitrocellulose membrane for 1 hour at 400 mA at 4 °C. The membrane was blocked for 60 minutes with 5% milk at room temperature. The membrane was then incubated overnight with antibodies against CTSK (Santa Cruz Biotechnology, Dallas, TX), TRAF3 (Santa Cruz Biotechnology), p50 (Cell Signal Technology, Danvers, MA), p52 (Cell Signal Technology), ERK (Cell Signal Technology), p-ERK (Cell Signal Technology), c-Fos (Cell Signal Technology) (GAPDH (Cell Signal Technology), IκBα (Cell Signal Technology) at a dilution of 1:1,000. It was then incubated for 1 hour with secondary rabbit antibody (Santa Cruz Biotechnology, goat anti-rabbit IgG [H+L], HRP-conjugated) and secondary mouse antibody (Santa Cruz Biotechnology, goat anti mouse IgG-HRP, sc-2005) at a concentration of 1:10, 000. For exposure, Immobilon Western HRP Substrate Peroxide Solution from GE Healthcare was used. Imaging was done with a Bio-Rad (Hercules, CA) ChemiDoc XRS+ with Image Lab Software.

Statistical Analysis

Results are presented as average ±SD or as average ±SEM, as indicated in the Brief Description of the Drawings. Statistical analysis was done using GraphPad Prism 7.0 (GraphPad Software, San Diego, CA). All other comparisons were analyzed by unpaired, 2-sided, independent student's t test, unless otherwise described in the Brief Description of the Drawings. One-way ANOVA analysis of variance was used to identify statistically significant differences in multiple group comparisons. A P value of less than 0.05 was considered statistically significant.

REFERENCES

1. Boyce B, Li J, Xing L, Yao Z. Bone Remodeling and the Role of TRAF3 in Osteoclastic Bone Resorption. Frontiers in Immunology 2018; 9.
2. Yao Z, Xing L, Boyce BF. NF-kappaB p100 limits TNF-induced bone resorption in mice by a TRAF3-dependent mechanism. The Journal of clinical investigation 2009; 119:3024-34.
3. Xiu Y, Xu H, Zhao C, et al. Chloroquine reduces osteoclastogenesis in murine osteoporosis by preventing TRAF3 degradation. J Clin Invest 2014; 124:297-310.

We claim:

1. A method for inhibiting or reducing bone loss in a subject in need thereof, the method comprising:

administering an effective amount of Cystatin E/M (CST6) to the subject to inhibit or reduce bone loss, wherein the subject has bone loss associated with multiple myeloma.

2. The method of claim 1, wherein the subject has osteoporosis associated with multiple myeloma.

3. The method of claim 1, wherein the multiple myeloma does not express CST6.

4. The method of claim 1, wherein the administration of an effective amount of CST6 comprises administering to the subject a recombinant CST6 protein set forth in SEQ ID NO: 3 or a polynucleotide construct comprising CST6 set forth in SEQ ID NO: 2 and capable of expressing CST6.

5. The method of claim 4, wherein the recombinant CST6 protein is linked to a targeting agent.

6. The method of claim 1, wherein the administration of an effective amount of CST6 comprises administering to the subject an effective amount of an immune cell expressing CST6 set forth in SEQ ID NO: 3.

7. The method of claim 6, wherein:

(a) the immune cell is a T cell, a natural killer T cell, or a macrophage;

(b) the immune cell comprises a chimeric antigen receptor (CAR) specific to the cancer of the subject; and/or (c) the immune cell comprises a polynucleotide construct comprising the polynucleotide sequence of CST6 set forth in SEQ ID NO: 2.

8. The method of claim 7, wherein the CAR specifically binds to B-cell maturation antigen (BCMA).

9. A method for inhibiting cancer cell growth and bone loss in a subject having a Cystatin E/M (CST6)-negative cancer, the method comprising:

administering to the subject an effective amount of a recombinant CST6protein set forth in SEQ ID NO: 3 or an immune cell expressing CST6 set forth in SEQ ID NO: 3 to inhibit cancer cell growth and bone loss, wherein the CST6-negative cancer is multiple myeloma.

10. The method of claim 9, the method further comprising:

obtaining a sample of the cancer from the subject, and detecting the lack of expression of CST6 in the cancer cells prior to administering the CST6.

11. The method of claim 9, wherein the immune cell is a T cell, a natural killer T cell, or macrophage.

12. The method of claim 9, wherein the immune cells comprise a polynucleotide construct comprising the polynucleotide sequence comprising CST6 set forth in SEQ ID NO: 2.

13. The method of claim 9, wherein the immune cell further expresses a targeting agent that binds to a tumor antigen specific to the cancer of the subject.

14. The method of claim 9, wherein the immune cell comprises a chimeric antigen receptor (CAR) specific to the cancer of the subject.

15. The method of claim 14, wherein the CAR is specific to a marker selected from the group consisting of CXCR4, HER2, BCMA, CD19, Kapp light chain, CD44 variant 6, CD56, CD70, CD38, CD138, SLAMF7, GPRC5D, NKG2DL, CD229, and CD24.

16. The method of claim 9, wherein the method further comprises:

resectioning a tumor prior to administration of the immune cells.

17. The method of claim 9, the method further comprising administering an anti-cancer therapy.

* * * * *

SEQUENCE LISTING

<160> NUMBER OF SEQ ID NOS: 12

<210> SEQ ID NO 1
<211> LENGTH: 592
<212> TYPE: DNA
<213> ORGANISM: Homo sapiens
<220> FEATURE:
<221> NAME/KEY: misc_feature
<222> LOCATION: (1)..(592)
<223> OTHER INFORMATION: CST6

<400> SEQUENCE: 1

```
actcacggct ctgagggctc cgacggcact gacggccatg gcgcgttcga acctcccgct     60

ggcgctgggc ctggccctgg tcgcattctg cctcctggcg ctgccacgcg acgcccgggc    120

ccggccgcag gagcgcatgg tcggagaact ccgggacctg tcgcccgacg acccgcaggt    180

gcagaaggcg gcgcaggcgg ccgtggccag ctacaacatg ggcagcaaca gcatctacta    240

cttccgagac acgcacatca tcaaggcgca gagccagctg gtggccggca tcaagtactt    300

cctgacgatg gagatgggga gcacagactg ccgcaagacc agggtcactg gagaccacgt    360

cgacctcacc acttgccccc tggcagcagg ggcgcagcag gagaagctgc gctgtgactt    420

tgaggtcctt gtggttccct ggcagaactc ctctcagctc ctaaagcaca actgtgtgca    480

gatgtgataa gtccccgagg gcgaaggcca ttgggtttgg ggccatggtg gagggcactt    540

caggtccgtg ggccgtatct gtcacaataa atggccagtg ctgcttcttg ca            592
```

<210> SEQ ID NO 2
<211> LENGTH: 450
<212> TYPE: DNA
<213> ORGANISM: Homo sapiens
<220> FEATURE:
<221> NAME/KEY: misc_feature
<222> LOCATION: (1)..(450)
<223> OTHER INFORMATION: CST6 coding sequence (CDS)

<400> SEQUENCE: 2

```
atggcgcgtt cgaacctccc gctggcgctg ggcctggccc tggtcgcatt ctgcctcctg     60

gcgctgccac gcgacgcccg ggcccggccg caggagcgca tggtcggaga actccgggac    120

ctgtcgcccg acgacccgca ggtgcagaag gcggcgcagg cggccgtggc cagctacaac    180

atgggcagca acagcatcta ctacttccga gacacgcaca tcatcaaggc gcagagccag    240

ctggtggccg gcatcaagta cttcctgacg atggagatgg ggagcacaga ctgccgcaag    300

accagggtca ctggagacca cgtcgacctc accacttgcc ccctggcagc aggggcgcag    360

caggagaagc tgcgctgtga ctttgaggtc cttgtggttc cctggcagaa ctcctctcag    420

ctcctaaagc acaactgtgt gcagatgtga                                     450
```

<210> SEQ ID NO 3
<211> LENGTH: 149
<212> TYPE: PRT
<213> ORGANISM: Homo sapiens
<220> FEATURE:
<221> NAME/KEY: MISC_FEATURE
<222> LOCATION: (1)..(149)
<223> OTHER INFORMATION: CST6

<400> SEQUENCE: 3

```
Met Ala Arg Ser Asn Leu Pro Leu Ala Leu Gly Leu Ala Leu Val Ala
1               5                   10                  15

Phe Cys Leu Leu Ala Leu Pro Arg Asp Ala Arg Ala Arg Pro Gln Glu
            20                  25                  30
```

```
Arg Met Val Gly Glu Leu Arg Asp Leu Ser Pro Asp Asp Pro Gln Val
        35                  40                  45

Gln Lys Ala Ala Gln Ala Ala Val Ala Ser Tyr Asn Met Gly Ser Asn
    50                  55                  60

Ser Ile Tyr Tyr Phe Arg Asp Thr His Ile Ile Lys Ala Gln Ser Gln
65                  70                  75                  80

Leu Val Ala Gly Ile Lys Tyr Phe Leu Thr Met Glu Met Gly Ser Thr
                85                  90                  95

Asp Cys Arg Lys Thr Arg Val Thr Gly Asp His Val Asp Leu Thr Thr
            100                 105                 110

Cys Pro Leu Ala Ala Gly Ala Gln Gln Glu Lys Leu Arg Cys Asp Phe
        115                 120                 125

Glu Val Leu Val Val Pro Trp Gln Asn Ser Ser Gln Leu Leu Lys His
    130                 135                 140

Asn Cys Val Gln Met
145


<210> SEQ ID NO 4
<211> LENGTH: 149
<212> TYPE: PRT
<213> ORGANISM: Mus musculus
<220> FEATURE:
<221> NAME/KEY: MISC_FEATURE
<222> LOCATION: (1)..(149)
<223> OTHER INFORMATION: CST6

<400> SEQUENCE: 4

Met Glu Arg Pro His Phe Pro Leu Ala Met Gly Leu Gly Leu Leu Ala
1               5                   10                  15

Phe Cys Leu Leu Thr Leu Ser Pro Asp Ala Arg Ala Glu Leu Arg Ser
            20                  25                  30

Arg Arg Thr Gly Glu Arg Gln Asn Leu Ser Pro Thr Asp Pro Arg Val
        35                  40                  45

Gln Lys Ala Ala Gln Ala Ala Val Ala Ser Tyr Asn Met Gly Ser Asp
    50                  55                  60

Ser Leu Tyr Tyr Phe Arg Asp Thr Lys Val Ile Asp Ala Lys Tyr Gln
65                  70                  75                  80

Leu Val Ala Gly Ile Lys Tyr Tyr Leu Thr Leu Asp Ile Glu Ser Thr
                85                  90                  95

Glu Cys Arg Lys Thr Arg Val Ser Gly Glu His Met Asp Leu Thr Thr
            100                 105                 110

Cys Pro Leu Ala Ala Gly Gly Gln Gln Glu Lys Leu Arg Cys Asn Phe
        115                 120                 125

Glu Leu Leu Glu Val Pro Trp Lys Asn Thr Thr Gln Leu Leu Lys His
    130                 135                 140

Asp Cys Val Gln Val
145


<210> SEQ ID NO 5
<211> LENGTH: 21
<212> TYPE: DNA
<213> ORGANISM: Artificial Sequence
<220> FEATURE:
<223> OTHER INFORMATION: Synthetic - Primer for real-time PCR

<400> SEQUENCE: 5

agcaggctgg aggactaagg t                                                21
```

<210> SEQ ID NO 6
<211> LENGTH: 24
<212> TYPE: DNA
<213> ORGANISM: Artificial Sequence
<220> FEATURE:
<223> OTHER INFORMATION: Synthetic - Primer for real-time PCR

<400> SEQUENCE: 6
gatttgtgca tctcagtgga agac 24

<210> SEQ ID NO 7
<211> LENGTH: 25
<212> TYPE: DNA
<213> ORGANISM: Artificial Sequence
<220> FEATURE:
<223> OTHER INFORMATION: Synthetic - Primer for real-time PCR

<400> SEQUENCE: 7
ccttatgtgg ctcaggtctt acttc 25

<210> SEQ ID NO 8
<211> LENGTH: 19
<212> TYPE: DNA
<213> ORGANISM: Artificial Sequence
<220> FEATURE:
<223> OTHER INFORMATION: Synthetic - Primer for real-time PCR

<400> SEQUENCE: 8
tggtccccga gaccacaat 19

<210> SEQ ID NO 9
<211> LENGTH: 23
<212> TYPE: DNA
<213> ORGANISM: Artificial Sequence
<220> FEATURE:
<223> OTHER INFORMATION: Synthetic - Primer for real-time PCR

<400> SEQUENCE: 9
aagtatgccc acaccaactg atc 23

<210> SEQ ID NO 10
<211> LENGTH: 20
<212> TYPE: DNA
<213> ORGANISM: Artificial Sequence
<220> FEATURE:
<223> OTHER INFORMATION: Synthetic - Primer for real-time PCR

<400> SEQUENCE: 10
gaaagcccgt tcccaagaaa 20

<210> SEQ ID NO 11
<211> LENGTH: 20
<212> TYPE: DNA
<213> ORGANISM: Artificial Sequence
<220> FEATURE:
<223> OTHER INFORMATION: Synthetic - Primer for real-time PCR

<400> SEQUENCE: 11
gccactgccg catcctcttc 20

-continued

```
<210> SEQ ID NO 12
<211> LENGTH: 20
<212> TYPE: DNA
<213> ORGANISM: Artificial Sequence
<220> FEATURE:
<223> OTHER INFORMATION: Synthetic - Primer for real-time PCR

<400> SEQUENCE: 12

agcctcaggg catcggaacc                                          20
```